US012502170B2

(12) United States Patent
Carpenter et al.

(10) Patent No.: US 12,502,170 B2
(45) Date of Patent: Dec. 23, 2025

(54) TRIGGER-BASED TISSUE ANCHOR DEPLOYMENT

(71) Applicant: EDWARDS LIFESCIENCES CORPORATION, Irvine, CA (US)

(72) Inventors: John Richard Carpenter, Santa Ana, CA (US); Bryan A. Janish, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 272 days.

(21) Appl. No.: 18/340,447

(22) Filed: Jun. 23, 2023

(65) Prior Publication Data

US 2023/0414215 A1 Dec. 28, 2023

Related U.S. Application Data

(60) Provisional application No. 63/366,898, filed on Jun. 23, 2022.

(51) Int. Cl.

*A61B 17/04* (2006.01)
*A61B 17/00* (2006.01)

(52) U.S. Cl.

CPC .................... *A61B 17/0487* (2013.01); *A61B 2017/00367* (2013.01); *A61B 2017/0488* (2013.01)

(58) Field of Classification Search

CPC ...... A61B 17/0487; A61B 2017/00367; A61B 2017/0488; A61B 17/0483; A61B 2017/0409; A61B 17/0401; A61B 2017/00243; A61B 2017/00783; A61B 2017/0474; A61B 17/0469; A61F 2/2466; A61F 2/2457

See application file for complete search history.

(56) References Cited

U.S. PATENT DOCUMENTS 3,131,957 A 5/1964 Musto
3,752,516 A 8/1973 Mumma
4,403,797 A 9/1983 Ragland, Jr.
4,662,376 A 5/1987 Belanger
4,807,625 A 2/1989 Singleton
5,144,961 A 9/1992 Chen et al.
(Continued)

FOREIGN PATENT DOCUMENTS

EP 0791330 A3 11/1997
EP 3505077 A1 7/2019
(Continued)

OTHER PUBLICATIONS

Alfieri, O. el al., "The double-orifice technique in mitral valve repair: a +A198:A225simple solution for complex problems," (2001) J. Thorne. Cardiovasc. Surg., 122(4):674-681.
(Continued)

*Primary Examiner* — Julian W Woo
(74) *Attorney, Agent, or Firm* — Chang and Hale LLP

(57) ABSTRACT

A medical instrument includes a handle, a suture lock associated with the handle, the suture lock being configured to fix a position of a portion of a suture line relative to a portion of the handle when the suture lock is in a locked configuration, and a manually-actuatable actuator associated with the handle and configured to cause the suture lock to transition from the locked position to an unlocked position.

19 Claims, 19 Drawing Sheets

(56) References Cited

U.S. PATENT DOCUMENTS 5,147,316 A 9/1992 Castillenti
5,312,423 A 5/1994 Rosenbluth et al.
5,391,176 A 2/1995 de la Torre
5,405,352 A 4/1995 Weston
5,454,821 A 10/1995 Harm et al.
5,472,446 A 12/1995 de la Torre
5,507,754 A 4/1996 Green et al.
5,527,323 A 6/1996 Jervis et al.
5,554,184 A 9/1996 Machiraju
5,626,614 A 5/1997 Hart
5,643,293 A 7/1997 Kogasaka et al.
5,681,331 A 10/1997 de la Torre et al.
5,716,368 A 2/1998 de la Torre et al.
5,727,569 A 3/1998 Benetti et al.
5,728,109 A 3/1998 Schulze et al.
5,746,752 A 5/1998 Burkhart
5,769,862 A 6/1998 Kammerer et al.
5,797,928 A 8/1998 Kogasaka
5,810,848 A * 9/1998 Hayhurst ............... A61B 17/04 606/232
5,824,065 A 10/1998 Gross
5,931,868 A 8/1999 Gross
5,957,936 A 9/1999 Yoon et al.
5,971,447 A 10/1999 Steck, III
6,010,531 A 1/2000 Donlon et al.
6,074,417 A 6/2000 Peredo
6,269,819 B1 8/2001 Oz et al.
6,332,893 B1 12/2001 Mortier et al.
6,562,051 B1 5/2003 Bolduc et al.
6,626,930 B1 9/2003 Allen et al.
6,629,534 B1 10/2003 St. Goar et al.
6,752,810 B1 6/2004 Gao et al.
6,840,246 B2 1/2005 Downing
6,921,408 B2 7/2005 Sauer
6,940,246 B2 9/2005 Mochizuki et al.
6,978,176 B2 12/2005 Lattouf
6,991,635 B2 1/2006 Takamoto et al.
6,997,950 B2 2/2006 Chawla
7,112,207 B2 9/2006 Allen et al.
7,291,168 B2 11/2007 Macoviak et al.
7,294,148 B2 11/2007 McCarthy
7,309,086 B2 12/2007 Carrier
7,316,706 B2 1/2008 Bloom et al.
7,373,207 B2 5/2008 Lattouf
7,431,692 B2 10/2008 Zollinger et al.
7,513,908 B2 4/2009 Lattouf
7,534,260 B2 5/2009 Lattouf
7,608,091 B2 10/2009 Goldfarb et al.
7,618,449 B2 11/2009 Tremulis et al.
7,632,308 B2 12/2009 Loulmet
7,635,386 B1 12/2009 Gammie
7,666,196 B1 2/2010 Miles
7,744,609 B2 6/2010 Allen et al.
7,837,727 B2 11/2010 Goetz et al.
7,871,368 B2 1/2011 Zollinger et al.
7,871,433 B2 1/2011 Lattouf
7,909,836 B2 * 3/2011 McLean ................. A61P 21/00 606/139
7,959,650 B2 6/2011 Kaiser et al.
8,029,518 B2 10/2011 Goldfarb et al.
8,029,565 B2 10/2011 Lattouf
8,043,368 B2 10/2011 Crabtree
8,147,542 B2 4/2012 Maisano et al.
8,187,323 B2 5/2012 Mortier et al.
8,226,711 B2 7/2012 Mortier et al.
8,241,304 B2 8/2012 Bachman
8,252,050 B2 8/2012 Maisano et al.
8,292,884 B2 10/2012 Levine et al.
8,303,622 B2 11/2012 Alkhatib
8,333,788 B2 12/2012 Maiorino
8,382,829 B1 2/2013 Call et al.
8,439,969 B2 5/2013 Gillinov et al.
8,454,656 B2 6/2013 Tuval
8,465,500 B2 6/2013 Speziali
8,475,525 B2 7/2013 Maisano et al.
8,500,800 B2 8/2013 Maisano et al.
8,608,758 B2 12/2013 Singhatat et al.
8,663,278 B2 3/2014 Mabuchi et al.
8,771,296 B2 7/2014 Nobles et al.
8,828,053 B2 9/2014 Sengun et al.
8,852,213 B2 10/2014 Gammie et al.
8,888,791 B2 11/2014 Jaramillo et al.
8,940,008 B2 1/2015 Kunis
9,131,884 B2 9/2015 Holmes et al.
9,192,287 B2 11/2015 Saadat et al.
2002/0013571 A1 1/2002 Goldfarb et al.
2003/0023254 A1 1/2003 Chiu
2003/0094180 A1 5/2003 Benetti
2003/0105519 A1 6/2003 Fasol et al.
2003/0120264 A1 6/2003 Lattouf
2003/0120341 A1 6/2003 Shennib et al.
2004/0044365 A1 3/2004 Bachman
2004/0093023 A1 5/2004 Allen et al.
2004/0199183 A1 10/2004 Oz et al.
2005/0004667 A1 1/2005 Swinford et al.
2005/0019735 A1 1/2005 Demas
2005/0075654 A1 4/2005 Kelleher
2005/0119735 A1 6/2005 Spence et al.
2005/0149067 A1 7/2005 Takemoto et al.
2005/0149093 A1 7/2005 Pokorney
2005/0154402 A1 7/2005 Sauer et al.
2005/0216036 A1 9/2005 Nakao
2005/0216077 A1 9/2005 Mathis et al.
2005/0261710 A1 11/2005 Sakamoto et al.
2005/0267493 A1 12/2005 Schreck et al.
2006/0030866 A1 2/2006 Schreck
2006/0100698 A1 5/2006 Lattouf
2006/0111739 A1 5/2006 Staufer et al.
2006/0167541 A1 7/2006 Lattouf
2006/0190030 A1 8/2006 To et al.
2006/0282088 A1 12/2006 Ryan
2007/0001857 A1 1/2007 Hartmann et al.
2007/0049952 A1 3/2007 Weiss
2007/0055292 A1 3/2007 Ortiz et al.
2007/0112422 A1 5/2007 Dehdashtian
2007/0112425 A1 5/2007 Schaller et al.
2007/0118151 A1 5/2007 Davidson
2007/0118154 A1 5/2007 Crabtree
2007/0149995 A1 6/2007 Quinn et al.
2007/0197858 A1 8/2007 Goldfarb et al.
2007/0213582 A1 9/2007 Zollinger et al.
2007/0270793 A1 11/2007 Lattouf
2008/0004597 A1 1/2008 Lattouf et al.
2008/0009888 A1 1/2008 Ewers et al.
2008/0065203 A1 3/2008 Khalapyan
2008/0140093 A1 6/2008 Stone et al.
2008/0167714 A1 7/2008 St. Goar et al.
2008/0188893 A1 8/2008 Selvitelli et al.
2008/0195126 A1 8/2008 Solem
2008/0228223 A1 9/2008 Alkhatib
2008/0249504 A1 10/2008 Lattouf et al.
2008/0269781 A1 10/2008 Funamura et al.
2009/0005863 A1 1/2009 Goetz et al.
2009/0043153 A1 2/2009 Zollinger et al.
2009/0105729 A1 4/2009 Zentgraf
2009/0105751 A1 4/2009 Zentgraf
2009/0276038 A1 11/2009 Tremulis et al.
2010/0023056 A1 1/2010 Johansson et al.
2010/0023117 A1 1/2010 Yoganathan et al.
2010/0023118 A1 1/2010 Medlock et al.
2010/0042147 A1 2/2010 Janovsky et al.
2010/0174297 A1 7/2010 Speziali
2010/0179574 A1 7/2010 Longoria et al.
2010/0210899 A1 8/2010 Schankereli
2010/0298930 A1 11/2010 Orlov
2011/0015476 A1 1/2011 Franco
2011/0022083 A1 1/2011 DiMatteo et al.
2011/0022084 A1 1/2011 Sengun et al.
2011/0028995 A1 2/2011 Miraki et al.
2011/0029071 A1 2/2011 Zlotnick et al.
2011/0060407 A1 3/2011 Ketai et al.
2011/0106106 A1 5/2011 Meier et al.
2011/0144743 A1 6/2011 Lattouf
2011/0264208 A1 10/2011 Duffy et al.

(56) References Cited

U.S. PATENT DOCUMENTS

| | | | |
|---|---|---|---|
| 2011/0270278 | A1 | 11/2011 | Overes et al. |
| 2011/0288637 | A1 | 11/2011 | De Marchena |
| 2011/0307055 | A1 | 12/2011 | Goldfarb et al. |
| 2012/0004669 | A1 | 1/2012 | Overes et al. |
| 2012/0143215 | A1 | 6/2012 | Corrao et al. |
| 2012/0150223 | A1 | 6/2012 | Manos et al. |
| 2012/0179184 | A1 | 7/2012 | Orlov |
| 2012/0184971 | A1 | 7/2012 | Zentgraf et al. |
| 2012/0203072 | A1 | 8/2012 | Lattouf et al. |
| 2012/0226294 | A1 | 9/2012 | Tuval |
| 2012/0226349 | A1 | 9/2012 | Tuval et al. |
| 2013/0018459 | A1 | 1/2013 | Maisano et al. |
| 2013/0035757 | A1 | 2/2013 | Zentgraf et al. |
| 2013/0253641 | A1 | 9/2013 | Lattouf |
| 2013/0282059 | A1 | 10/2013 | Ketai et al. |
| 2013/0345749 | A1 | 12/2013 | Sullivan et al. |
| 2014/0031926 | A1 | 1/2014 | Kudlik et al. |
| 2014/0039607 | A1 | 2/2014 | Kovach |
| 2014/0067052 | A1 | 3/2014 | Chau et al. |
| 2014/0114404 | A1 | 4/2014 | Gammie et al. |
| 2014/0214152 | A1 | 7/2014 | Bielefeld |
| 2014/0243968 | A1 | 8/2014 | Padala |
| 2014/0364938 | A1 | 12/2014 | Longoria et al. |
| 2015/0032127 | A1 | 1/2015 | Gammie et al. |
| 2015/0045879 | A1 | 2/2015 | Longoria et al. |
| 2019/0175346 | A1 | 6/2019 | Schaffner et al. |
| 2020/0155315 | A1 | 5/2020 | Zhang et al. |

FOREIGN PATENT DOCUMENTS

| | | | |
|---|---|---|---|
| JP | 2013517110 | A | 5/2013 |
| WO | 2004037463 | A1 | 5/2004 |
| WO | 2006127509 | A2 | 11/2006 |
| WO | 2007100268 | A2 | 9/2007 |
| WO | 2007119057 | A1 | 10/2007 |
| WO | 2008013869 | A2 | 1/2008 |
| WO | 2008124110 | A3 | 12/2008 |
| WO | 2008143740 | A3 | 2/2009 |
| WO | 2006078694 | A3 | 4/2009 |
| WO | 2009081396 | A2 | 7/2009 |
| WO | 2010070649 | A1 | 6/2010 |
| WO | 2010105046 | A1 | 9/2010 |
| WO | 2012137208 | A1 | 10/2012 |
| WO | 2013003228 | A1 | 1/2013 |
| WO | 2014093861 | A1 | 6/2014 |
| WO | 2015020816 | A1 | 2/2015 |
| WO | 2016192481 | A1 | 12/2016 |

OTHER PUBLICATIONS

Barbero-Marcial, M. et al., "Transxiphoid Approach Without Median Sternotomy for the Repair of Atrial Septa! Defects," (1998) Ann. Thorne. Surg., 65(3):771-774.

Braunberger, E. et al., "Very long-term results (more than 20 years) of valve repair with Carpentier's echniques in nonheumatic mitral valve insufficiency," (2001) Circulation, I 04:1-8-1-11.

Carpentier, Alain, "Cardiac valve surgery—the 'French coffec-tion'," The Journal of Thoracic and Cardiovascular Surgery, vol. 86, No. 3, Sep. 1983, 15 pages.

David, T. E. et al., "Mitra! valve repair by replacement of chordae tendineae with polytetrafluoroethylene sutures," ( 1991) J. Thorne. Cardiovasc. Surg., 101 (3 ):495-50.

David, T. E. et al., "Replacement of chordae tendineae with Gore-Tex sutures: a ten-year experience," ( 1996) J. Heart Valve Dis., 5( 4 ):352-355.

Doty, D. B. et al., "Full-Spectrum Cardiac Surgery Through a Minimal Incision: Mini-Sternotomy (Lower Half) Technique," ( 1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitral valve prolapse," (1997) J. Heal1 Valve Dis., 6(6):594-598.

Frater, R. W. M. ct al., "Chordal replacement in mitral valve repair," ( 1990) Circulation, 82(suppl. IV):IV-125-IV-130.

Frater, R. W. M., "Anatomical rules for the plastic repair of a diseased mitral valve," ( 1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricu-lar Dysfunction and Functional Mitral Regurgitation," (2003) Ann. Thorne. Surg., 75:809-811.

Kasegawa, H. ct al., "Simple method for detennining proper length of allificial chordae in mitral valve repair," ( 1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylcnc suture: a finite element study," (1996) J. Card. Surg., 11(2):136-145.

Langer, F. et al., "RING plus STRING: Papillary muscle reposi-tioning as an adjunctive repair technique for ischemic mitral regur-gitation," (2007) J. Thorne. Cardiovasc. Surg., 133( I): 247-249.

Maisano, F. et al., "The double-orifice technique as a standardized approach to treat mitral regurgitation due to severe rnyxomatous disease: surgical technique," (2000) European Journal of Cardio-thorncic Surgery, 17(3):201-205.

Merendino, K. A. et al., "The open con-ection of rheumatic mitral regurgitation and/or stenosis with special reference to regurgitation treated by posterornedial annuloplasty utilizing a pump-oxygenator," (1959) Annals of Surgery, 150(1 ):5-22.

Minatoya, K. et al., "Pathologic aspects of polytetrafluoroethylene sutures in human heart," ( 1996) Ann. Thorac. Surg., 61 (3 ):883-887.

Mohty, D. ct al., "Very long-term survival and durability ofmitral valve repair for mitral valve prolapse," (2001) Circulation, 104:1-1-1-7.

*Neochord, Inc.* v. *University of Maryland, Bal tim ore,* Case No. JPR2016-00208, Decision on Institution of Inter Faries Review, 37 CFR §42. I 08, Paper 6, Entered May 24, 2016, 28 pages.

*Neochord, Inc.* v. *University of Maryland, Baltimore,* Case No. IPR2016-00208, Declaration of Dr. Lishan Aklog, dated Nov. 17, 2015, 91 pages.

*Neochord, Inc.* v. *University of Maryland, Baltimore,* Case No. IPR2016-00208, Petition for inter ParlesReview of U.S. Pat. No. 7,635,386, dated Nov. 18, 2015, 65 pages.

Nigro, J. J. et al., "Neochordal repair of the posterior mitral leaflet," (2004) J. Thorne. Cardiovasc. Surg., 127 (2):440-447.

Phillips, M. R. et al., "Repair of anterior leaflet mitral valve prolapse: chordal replacement versus chordal shrntening," (2000) Ann. Thorac. Surg., 69(1 ):25-29.

Russo, M. J. ct al. •Transapical Approach for Mitral Valve Repair during Insertion of a Left Ventricular Assist Device, Hindawi Publishing Corporation, The Scientific World Journal, vol. 2013, Article ID 925310, [ online], Retrieved from the internet: <URL: http://dx.doi.org/J 0.1155/2013/92531 O> Apr. 11, 2013, 4 pages.

Sarsam, M.A. I., "Simplified technique for determining the length of artificial cllordae in milral valve repair," (2002) Ann. Thorac. Surg., 73(5): 1659-1660.

Savage, E. B. et al., Use of mitral valve repair: analysis of contemporary United States experience reported to the society of thoracic surgeons national cardiac database, . . . (2003) Ann. Thorne. Surg., 75:820-825.

Speziali, G. et al., "Coll'ection of Mitra! Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heaii surgery without cardiopulmonary bypass: Atrial septa! defect clo-sure in a swine model," (2005) J. Thorne. Cardiovasc. Surg., 130: 1348-1357.

(56) References Cited

OTHER PUBLICATIONS

Von Oppell, U. O. et al., “Chordal replacement for both minimally invasive and conventional mitral valve surgery using prcrncasurcd Gore-Tex loops,” (2000) Ann. Thorne. Surg., 70(6):2166-2168.
Zussa, C. et al., Artificial mitral valve chordae: experimental and clinical experience;• ( 1990) Ann. Thorne. Surg., 50 (3):367-373.
Zussa, C. et al., “Seven-year experience with chordal replacement with expanded polytetrafluoroethylene in floppyrnitral valve,” (1994)1. Thorac. Cardiovasc. Surg., 108(1):37-41.
Zussa, C. et al., “Surgical technique for artificial rnitral chordae implantation,” ( 1991) Journal of Cardiac Surgery, 6 (4):432-438.
Zussa, C., “Artificial chordae,” (1995) J. Heart Valve Dis., 4(2):S249-S256.

* cited by examiner

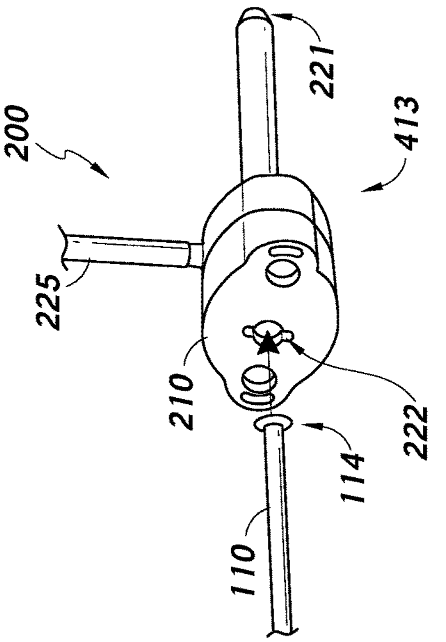
FIG. 4-3
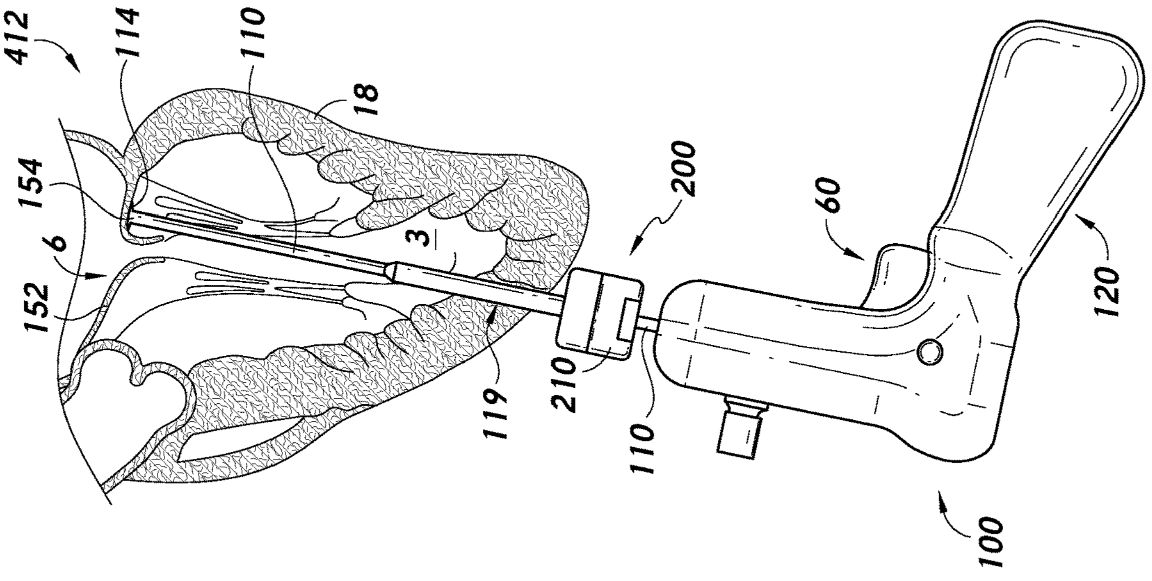
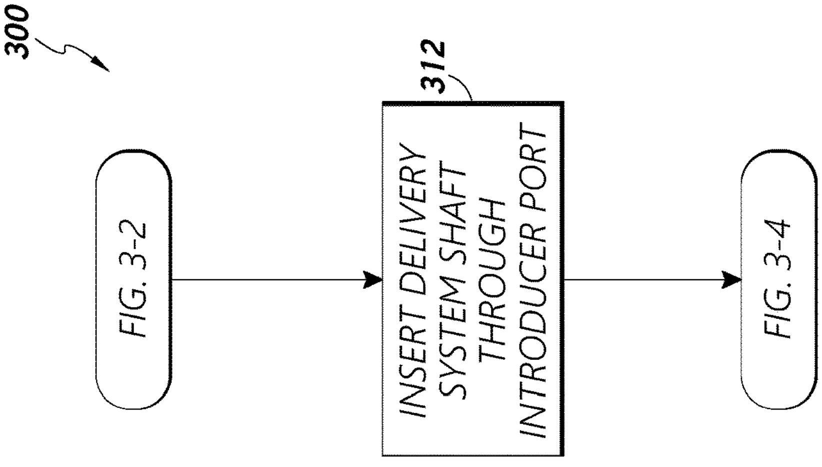
FIG. 3-3

DISTAL
PROXIMAL
120
127
1101
121
93
85
33
32
81a
42
43
84
77
75
88
79
78
80
87
62
67
70
71
55
60
100
110
114
40
91
30
111

TRIGGER-BASED TISSUE ANCHOR DEPLOYMENT

RELATED APPLICATION(S)

This application claims the benefit of U.S. Patent Application No. 63/366,898, filed on Jun. 23, 2022, the entire disclosure which is incorporated by for all purposes.

BACKGROUND

Field

The present disclosure generally relates to the field of medical procedures and devices.

Description of Related Art

Various medical procedures involve deploying tissue anchors in internal anatomy of a patient. Tissue anchors can be delivered/deployed using certain devices and systems, the design of which can have an impact on the efficacy and/or user experience associated with related medical procedures.

SUMMARY

Described herein are methods, systems, and devices to facilitate tissue anchor deployment. In some implementations, the present disclosure relates to a tissue anchor deployment device/system comprising an elongate shaft, a handle, and a trigger-type actuator configured to cause actuation of various components of the device/system to facilitate tissue anchor deployment, including suture tension management and/or other functions.

Methods and structures disclosed herein for treating a patient also encompass analogous methods and structures performed on or placed on a simulated patient, which is useful, for example, for training; for demonstration; for procedure and/or device development; and the like. The simulated patient can be physical, virtual, or a combination of physical and virtual. A simulation can include a simulation of all or a portion of a patient, for example, an entire body, a portion of a body (e.g., thorax), a system (e.g., cardiovascular system), an organ (e.g., heart), or any combination thereof. Physical elements can be natural, including human or animal cadavers, or portions thereof; synthetic; or any combination of natural and synthetic. Virtual elements can be entirely in silico, or overlaid on one or more of the physical components. Virtual elements can be presented on any combination of screens, headsets, holographically, projected, loud speakers, headphones, pressure transducers, temperature transducers, or using any combination of suitable technologies.

Any of the various systems, devices, apparatuses, etc. in this disclosure can be sterilized (e.g., with heat, radiation, ethylene oxide, hydrogen peroxide, etc.) to ensure they are safe for use with patients, and the methods herein can comprise sterilization of the associated system, device, apparatus, etc. (e.g., with heat, radiation, ethylene oxide, hydrogen peroxide, etc.).

For purposes of summarizing the disclosure, certain aspects, advantages and novel features have been described. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

BRIEF DESCRIPTION OF THE DRAWINGS

Various examples are depicted in the accompanying drawings for illustrative purposes and should in no way be interpreted as limiting the scope of this disclosure. In addition, various features of different disclosed examples can be combined to form additional examples, which are part of this disclosure. Throughout the drawings, reference numbers may be reused to indicate correspondence between reference elements.

FIGS. 3-1, 3-2, 3-3, 3-4, and 3-5 provide a flow diagram illustrating a process for implanting a leaflet anchor in accordance with one or more examples.

FIGS. 4-1, 4-2, 4-3, 4-4, and 4-5 provide images of cardiac anatomy and certain devices/systems corresponding to operations of the process of FIGS. 3-1, 3-2, 3-3, 3-4, and 3-5 in accordance with one or more examples.

FIG. 5-1 illustrates a view of an atrial/distal side of a valve having two tissue anchors deployed therein in accordance with one or more examples.

FIG. 5-2 illustrates a view of an atrial/distal side of a valve having six tissue anchors deployed therein in accordance with one or more examples.

FIGS. 7-1B and 7-2B show detailed images of the trigger lock associated with FIGS. 7-1A and 7-2A in locked and unlocked configurations, respectively, in accordance with one or more examples.

DETAILED DESCRIPTION

Figure 1:
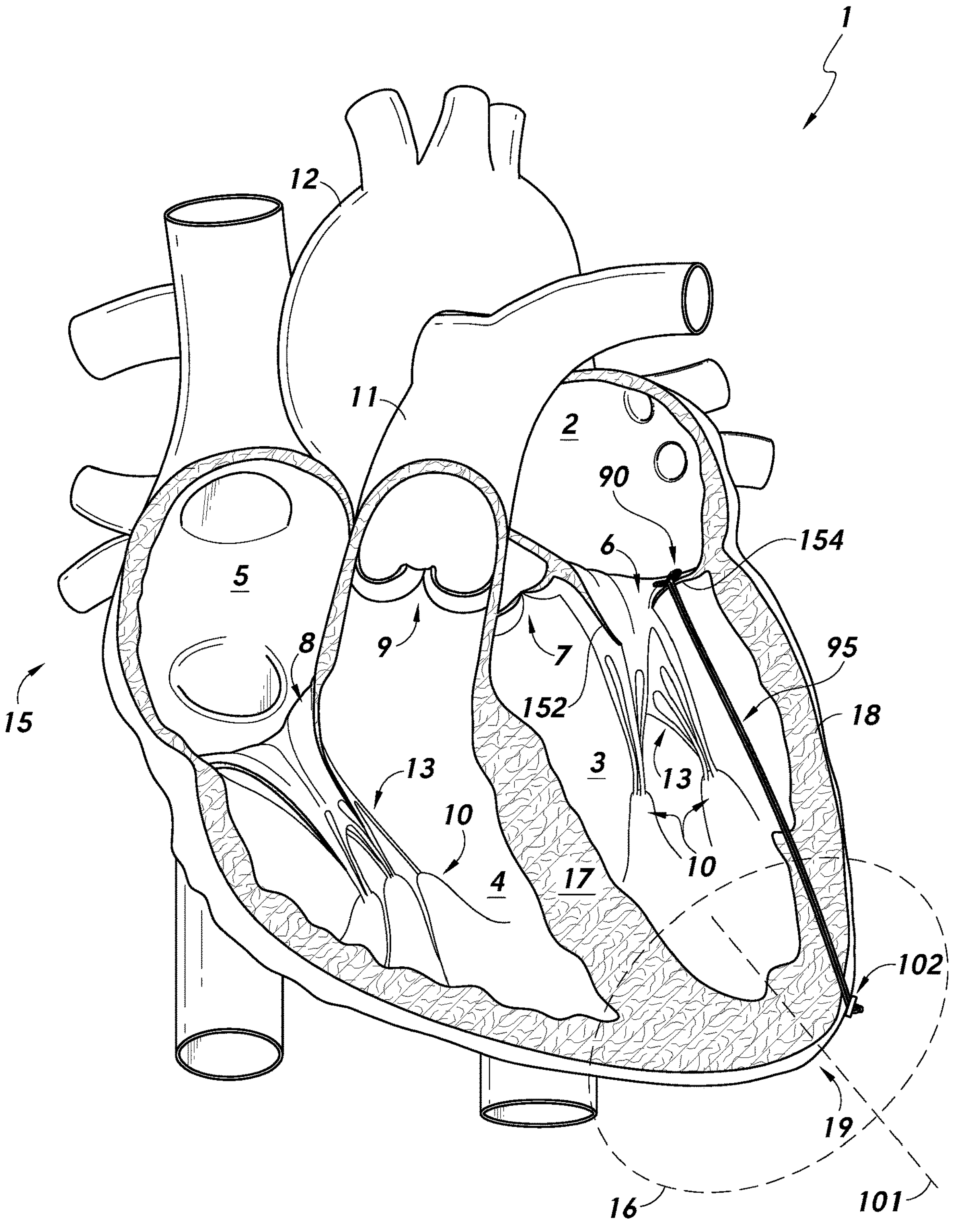
FIG. 1 illustrates an example representation of a human heart having a suture-tethered tissue anchor deployed therein in accordance with one or more examples.

The headings provided herein are for convenience only and do not necessarily affect the scope or meaning of the claims.

Although certain preferred examples and examples are disclosed below, inventive subject matter extends beyond the specifically disclosed examples to other alternative examples and/or uses and to modifications and equivalents thereof. Thus, the scope of the claims that may arise herefrom is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain examples; however, the order of description should not be construed to imply that these operations are order dependent. Additionally, the structures, systems, and/or devices described herein may be embodied as integrated components or as separate components. For purposes of comparing various examples, certain aspects and advantages of these examples are described. Not necessarily all such aspects or advantages are achieved by any particular example. Thus, for example, various examples may be carried out in a manner that achieves or optimizes one advantage or group of advantages as taught herein without necessarily achieving other aspects or advantages as may also be taught or suggested herein.

Certain reference numbers are re-used across different figures of the figure set of the present disclosure as a matter of convenience for devices, components, systems, features, and/or modules having features that may be similar in one or more respects. However, with respect to any of the examples disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics, to be identical, or to be entirely independent of one another.

Where an alphanumeric reference identifier is used that comprises a numeric portion and an alphabetic portion (e.g., '10a,' where '10' is the numeric portion and 'a' is the alphabetic portion), references in the written description to only the numeric portion (e.g., '10') may refer to any feature identified in the figures using such numeric portion (e.g., '10a,' '10b,' '10c,' etc.), even where such features are identified with reference identifiers that concatenate the numeric portion thereof with one or more alphabetic characters (e.g., 'a,' 'b,' 'c,' etc.). That is, a reference in the present written description to a feature '10' may be understood to refer to either an identified feature '10a' in a particular figure of the present disclosure or to an identifier '10' or '10b' in the same figure or another figure, as an example.

Certain standard anatomical terms of location are used herein to refer to certain device components/features and to the anatomy of animals, and namely humans, with respect to the preferred examples. Although certain spatially relative terms, such as "proximal," "distal," "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element (s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

The present disclosure relates to systems, devices, and methods for delivering tissue anchors using a device/system comprising an elongate shaft coupled to a handle, wherein the handle is associated with a trigger-type actuator for deploying tissue anchors from a distal end of the shaft. The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly. With respect to instrument handles disclosed herein, a feature or component that is "associated with" a handle may be understood to be disposed on, within, or mechanically contacting or coupled to, the handle in any way.

Trigger-based tissue anchor deployment can be implemented, for example, for deploying tissue/leaflet anchors in heart valve leaflets to tether the same to a heart wall for valve repair. Such tethers may be left implanted in the patient anatomy to serve as artificial chordae tendineae. Although trigger-based actuators are disclosed in detail herein, it should be understood that other types of actuators may be implemented in accordance with features of the examples of the present disclosure, wherein such actuators are configured to produce linear actuation of needle and/or pusher components of the tissue anchor delivery system/device. For example, any type of rack-and-pinion actuation system/assembly may be implemented in connection with systems, devices, and processes disclosed herein.

Devices and processes disclosed herein may be implemented in patients suffering from mitral regurgitation caused by, for example, mid-segment leaflet prolapse as a result of degenerative mitral valve disease. As referenced above, devices disclosed herein may be suited for use in connection with procedures for delivering and anchoring artificial chordae and/or associated tissue anchor devices/components (e.g., ePTFE cords/sutures) to a prolapsed mitral valve leaflet in a minimally-invasive, beating-heart procedure. Trigger-type actuators (referred to herein as "trigger actuators," or simply "triggers," in some contexts) can be implemented in a manner as described herein such that a single (e.g., continuous) stroke/pull of the trigger causes linear actuation (e.g., in a dimension parallel with a shaft of the relevant tissue anchor delivery device/system) of a plurality of components of the associated tissue anchor delivery device/system to cause a needle puncture of the target tissue and subsequent deployment of a tissue anchor, such as a suture-knot-type tissue anchor, from the needle (e.g., from off of or within the needle), and to further cause formation of the tissue anchor into an anchoring retention form (e.g., bulky-knot form). For example, the trigger actuator may cause instrument hub(s), drive rod(s), and/or other mechanical components associated with needle and pusher instruments/components to advance in a manner as to achieve the needle puncture, tissue anchor deployment, and/or tissue anchor formation functionality/aspects referenced above. The trigger actuator may further be configured to cause actuation of components that modify the tension and/or locking/unlocking of suture tails associated with the tissue anchor(s), such as with respect to suture tail(s) disposed at least partially within a handle of the tissue anchor deployment device/system.

Certain examples are disclosed herein in the context of cardiac implants and procedures. However, although certain principles disclosed herein are particularly applicable to the anatomy of the heart, it should be understood that tissue anchor delivery devices and trigger-based tissue anchor deployment/formation procedures in accordance with aspects of the present disclosure may be implemented in connection with any suitable or desirable anatomy, or in non-biological applications.

The following includes a general description of human cardiac anatomy that is relevant to certain inventive features and examples disclosed herein and is included to provide context for certain aspects of the present disclosure. In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

FIG. 1 illustrates an example representation of a heart 1 having a tissue anchor 90 implanted therein, the tissue anchor 90 being tethered to a heart wall 18 via suture tail(s) 95 coupled to and/or integrated with the tissue anchor 90. The heart 1 includes four chambers, namely the left ventricle 3, the left atrium 2, the right ventricle 4, and the right atrium 5. A wall of muscle 17, referred to as the septum, separates the left 2 and right 5 atria and the left 3 and right 4 ventricles. The inferior tip 19 of the heart 1 is referred to as the apex and is generally located on the midclavicular line, in the fifth intercostal space. The apex 19 can be considered part of the greater apical region 16 of the heart.

The left ventricle 3 is the primary pumping chamber of the heart 1. A healthy left ventricle is generally conical or apical in shape in that it is longer (along a longitudinal axis extending in a direction from the aortic valve 7 to the apex 19) than it is wide (along a transverse axis extending between opposing walls at the widest point of the left ventricle 3) and descends from a base 15 of the heart 1 with a decreasing cross-sectional circumference to the point or apex 19. Generally, the apical region 16 of the heart is a bottom region of the heart that is within the left or right ventricular region but is distal to the mitral 6 and tricuspid 8 valves and toward the tip 19 of the heart. More specifically, the apical region 16 may be considered to be within about 20 cm to the right or to the left of the median axis 101 of the heart 1.

The pumping of blood from the left ventricle 3 is accomplished by a squeezing motion and a twisting or torsional motion. The squeezing motion occurs between the lateral wall 18 of the left ventricle 3 and the septum 17. The twisting motion is a result of heart muscle fibers that extend in a circular or spiral direction around the heart. When these fibers contract, they produce a gradient of angular displacements of the myocardium from the apex 19 to the base 15 about the longitudinal axis of the heart. The resultant force vectors extend at angles from about 30-60 degrees to the flow of blood through the aortic valve 7. The contraction of the heart is manifested as a counterclockwise rotation of the apex 19 relative to the base 15, when viewed from the apex 19. A healthy heart can pump blood from the left ventricle in a very efficient manner due to the spiral contractility of the heart.

The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (e.g., systole) and open during ventricular expansion (e.g., diastole). The valves of the heart 1 further include the pulmonary valve 9, which separates the right ventricle 4 from the pulmonary artery ii and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets (anterior and posterior) and separates the left atrium 2 from the left ventricle 3. Generally, the anterior leaflet of the mitral valve 6 may cover approximately two-thirds of the valve annulus. Although the anterior leaflet covers a greater portion of the annulus, the posterior leaflet may comprise a larger surface area in certain anatomies. The mitral valve 6 may generally be configured to open during diastole so that blood in the left atrium 2 can flow into the left ventricle 3, and close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The atrioventricular (e.g., mitral and tricuspid) heart valves may comprise a collection of chordae tendineae 13 and papillary muscles 10 for securing the leaflets of the respective valves to promote and/or facilitate proper coaptation of the valve leaflets and prevent prolapse thereof. The papillary muscles 10, for example, may generally comprise finger-like projections from the respective ventricle walls. With respect to the tricuspid valve 8, the normal tricuspid valve may comprise three leaflets and three corresponding papillary muscles 10. The leaflets of the tricuspid valve 8 may be referred to as the anterior, posterior and septal leaflets, respectively. The valve leaflets of the mitral valve 6 are connected to papillary muscles 10 by chordae tendineae 13 that are disposed in the left ventricle 3 along with the papillary muscles 10. A normal mitral valve may be tethered to two papillary muscles corresponding to the two mitral valve leaflets.

Various disease processes can impair the proper functioning of one or more of the valves of the heart. These disease processes include degenerative processes (e.g., Barlow's disease, fibroelastic deficiency), inflammatory processes (e.g., rheumatic heart disease) and infectious processes (e.g., endocarditis). Additionally, damage to the ventricle from prior heart attacks (e.g., myocardial infarction secondary to coronary artery disease) or other heart diseases (e.g., cardiomyopathy) can distort the valve's geometry causing it to dysfunction. However, the vast majority of patients undergoing valve surgery, such as mitral valve surgery, suffer from a degenerative disease that causes a malfunction in one or more leaflets of the valve which results in prolapse and regurgitation.

The mitral valve 6 and tricuspid valve 8 can be divided into three parts: an annulus, leaflets, and a sub-valvular apparatus. The sub-valvular apparatus can be considered to include the papillary muscles 10 and the chordae tendineae 13, which can elongate and/or rupture. If a valve is functioning properly, when closed, the free margins or edges of the leaflets come together and form a tight junction, the arc of which, in the mitral valve, is known as the line, plane or area of coaptation. Normal mitral and tricuspid valves open when the ventricles relax allowing blood from the atrium to fill the decompressed ventricle. When the ventricle contracts, the chordae tendineae advantageously properly tether or position the valve leaflets such that the increase in pressure within the ventricle causes the valve to close, thereby preventing blood from leaking into the atrium and assuring that substantially all of the blood leaving the ventricle is ejected through the aortic valve 7 or pulmonic valve 9 and into the arteries of the body. Accordingly, proper function of the valves depends on a complex interplay between the annulus, leaflets, and sub-valvular apparatus. Lesions in any of these components can cause the valve to dysfunction and thereby lead to valve regurgitation.

Generally, there are three mechanisms by which a heart valve becomes regurgitant or incompetent; they include Carpentier's type I, type II and type III malfunctions. A Carpentier type I malfunction involves the dilation of the annulus such that normally functioning leaflets are distracted from each other and fail to form a tight seal (e.g., do not coapt properly). Included in a type I mechanism malfunction are perforations of the valve leaflets, as in endocarditis. A Carpentier's type II malfunction involves prolapse of one or both leaflets above the plane of coaptation. This is the most common cause of mitral regurgitation and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic disease (IIIa) or dilation of the ventricle (IIIb).

One or more chambers in the heart 1 may be accessed in accordance with certain heart valve-repair procedures and/or other interventions. Access into a chamber in the heart may be made at any suitable site of entry. In some implementations, access is made to a chamber of the heart, such as a target ventricle (e.g., left ventricle) associated with a diseased heart valve, through the apical region 16. For example, access into the left ventricle 3 (e.g., to perform a mitral valve repair) may be gained by making a relatively small incision at the apical region 16, close to (or slightly skewed toward the left of) the median axis 101 of the heart. Access into the right ventricle 4 (e.g., to perform a tricuspid valve repair) may be gained by making a small incision into the apical region 16, close to or slightly skewed toward the right of the median axis 101 of the heart. Accordingly, the ventricle can be accessed directly via the apex 19, or via an off-apex location that is in the apical region 16 but slightly removed from the tip/apex, such as via lateral ventricular wall, a region between the apex and the base of a papillary muscle, or even directly at the base of a papillary muscle. In some implementations, the incision made to access the appropriate ventricle of the heart is no longer than about 1 mm to about 5 cm, from 2.5 mm to about 2.5 cm, or from about 5 mm to about 1 cm in length. When a percutaneous approach is sought, no incision into the apex region of the heart may be made, but rather access into the apical region 16 may be gained by direct needle puncture, for instance by an 18-gauge needle, through which an appropriate repair instrument can be advanced.

Heart Valve Leaflet Tethering

Certain inventive features disclosed herein relate to systems, devices, and/or processes for repairing heart valves or any other type of target organ tissue. In some implementations, a tissue anchor delivery device/system may be employed in repairing a mitral valve in a patient suffering from degenerative mitral regurgitation or other condition. In some implementations, a transapical, off-pump repair procedure is implemented in which at least part (e.g., a shaft portion/assembly) of a valve repair system/device is inserted in the left ventricle and advanced to the surface of the diseased portion of a target mitral valve leaflet and used to deploy/implant one or more tissue anchors in the target leaflet. The tissue anchor(s) (e.g., sutureform formed into a bulky knot retention form) may advantageously be integrated or coupled with one or more artificial/synthetic cords serving a function similar to that of chordae tendineae. Such artificial cord(s) may comprise suture(s) and/or suture tail portion(s) associated with a knot-type tissue anchor and may comprise any suitable or desirable material, such as expanded polytetrafluoroethylene (ePTFE) or the like. The term "suture" is used herein according to its broad and ordinary meaning and may refer to any elongate cord, strip, strand, line, tie, string, ribbon, strap, or portion thereof, or other type of material used in medical procedures. One having ordinary skill in the art will understand that a wire or other similar material may be used in place of a suture. Furthermore, in some contexts herein, the terms "cord," "chord," "chordae," "suture tail," and "suture" may be used substantially interchangeably. In addition, use of the singular form of any of the suture-related terms listed above, including the terms "suture," "suture tail," and "cord," may be used to refer to a single suture/cord, or to a portion thereof, or to a plurality of sutures/cords, such as a pair of suture/cord tails emanating from a single anchor, knot, form, device, or other structure or assembly. Where a suture knot/anchor is deployed on a distal side of a tissue portion, and where two suture portions/tails extend from the knot/anchor on a proximal side of the tissue, either or both of the suture portions/tails may be referred to as a "suture" or a "cord," regardless of whether both portions/tails are part of a unitary suture or cord or are separate.

Processes for repairing a target organ tissue, such as repair of mitral valve leaflets to address mitral valve regurgitation, can include inserting a tissue anchor delivery device/system, such as a delivery device as described in PCT Application No. PCT/US2012/043761, (published as WO 2013/003228, and referred to herein as "the '761 PCT application") and/or in PCT Application No. PCT/US2016/055170 (published as WO 2017/059426 and referred to herein as "the '170 PCT application"), the entire disclosures of which are incorporated herein by reference, into a body and extending a distal end of the delivery device to a proximal side of the target tissue (e.g., leaflet).

The '761 PCT Application and the '170 PCT Application describe in detail methods and devices for performing non-invasive procedures to repair a cardiac valve, such as a mitral valve. Such procedures include procedures to repair regurgitation that occurs when the leaflets of the mitral valve do not coapt properly at peak contraction pressures, resulting in an undesired backflow of blood from the ventricle into the atrium. As described in the '761 PCT Application and the '170 PCT Application, after the malfunctioning cardiac valve has been assessed and the source of the malfunction verified, a corrective procedure can be performed. Various procedures can be performed in accordance with the methods described therein to effectuate a cardiac valve repair, which may depend on the specific abnormality and the tissues involved.

With further reference to FIG. 1, there is shown an example deployed leaflet/tissue anchor 90 deployed in a hear valve leaflet 154 and tethered to a heart/ventricle wall 18 via one or more sutures/suture tails 95 coupled to and/or associated with the anchor 90. The suture tails 95 coupled to the anchor 90 may be secured at the desired tension using a pledget or other suture-fixing/locking device or mechanism 102 on the outside of the heart wall 18 through which the suture tails 95 may run. A knot or other suture fixation mechanism or device may be implemented to hold the sutures at the desired tension and to the pledget 102. With the suture tail(s) 95 fixed to the ventricle wall 18, a portion of the suture tail(s) 95 disposed within the ventricle 3 may advantageously function as replacement leaflet cords (e.g., chordae tendineae) that are configured to tether the target leaflet 14 in a desired manner.

Figure 2:
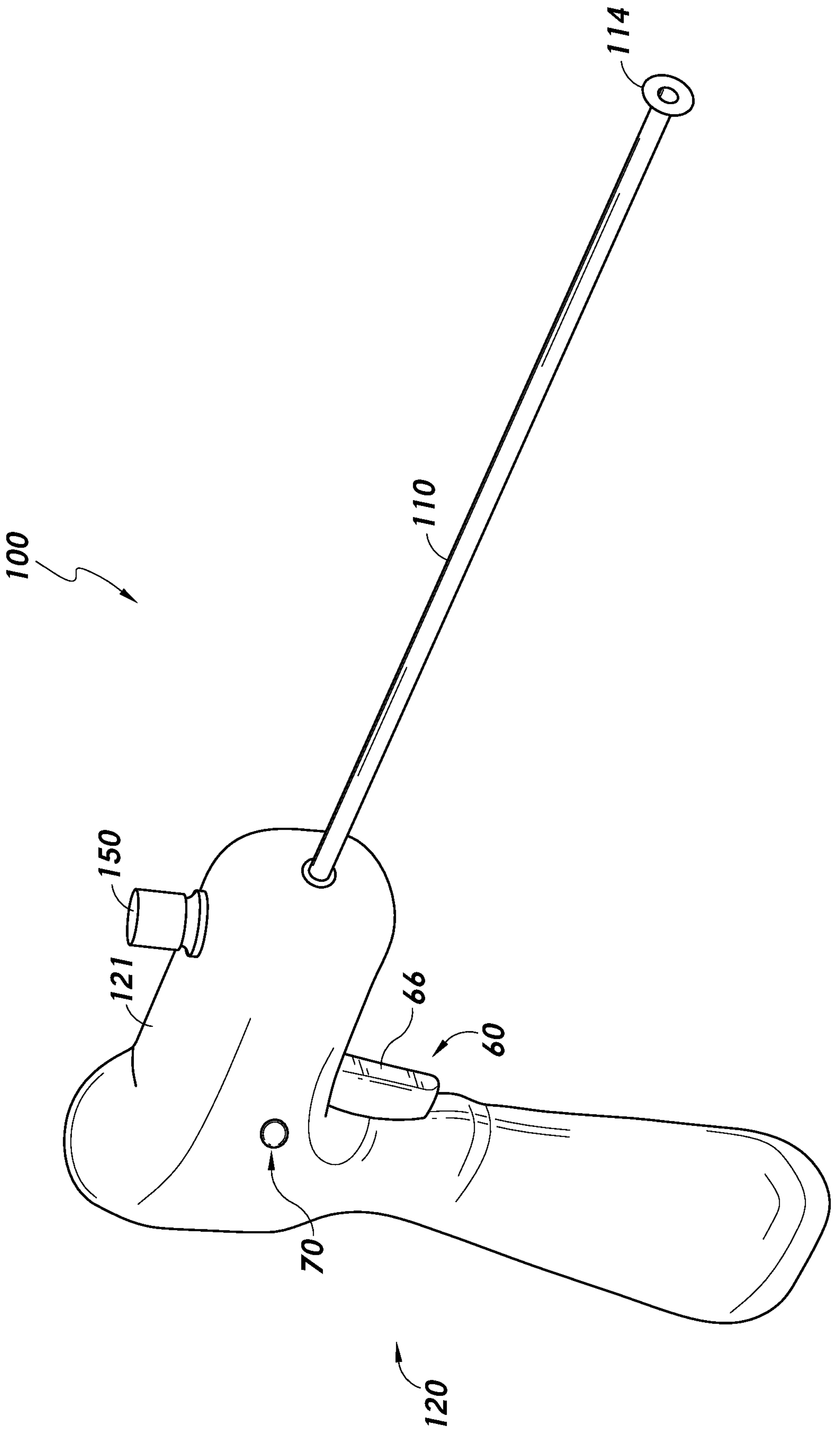
FIG. 2 is a perspective view of a tissue anchor delivery device in accordance with one or more examples.

FIG. 2 is a perspective view of a tissue anchor delivery device/system 100 in accordance with one or more examples. Although described as a tissue anchor delivery 'system' in some contexts, it should be understood that the tissue anchor delivery device 100 may be considered a 'device' or a 'system,' and such terms are used substantially interchangeably herein with respect to tissue anchor delivery solutions presented herein; the tissue anchor delivery system 100, and other tissue anchor delivery devices/systems disclosed herein, may further be considered an 'assembly,' or an 'instrument.' The tissue anchor delivery system 100 may be used to repair a heart valve, such as a mitral valve, and improve functionality thereof. For example, the tissue anchor delivery system 100 may be used to reduce the degree of mitral regurgitation in patients suffering from mitral regurgitation caused by, for example, midsegment prolapse of valve leaflets as a result of degenerative mitral valve disease. In order to repair such a valve, the tissue anchor delivery system 100 may be utilized to deliver and anchor tissue anchors, such as suture-knot-type tissue anchors, in a prolapsed valve leaflet. As described in detail below, such procedure may be implemented on a beating heart.

The delivery system 100 includes a rigid elongate tube 110 forming at least one internal working lumen. Although described in certain examples and/or contexts as comprising a rigid elongate tube, it should be understood that tubes, shafts, lumens, conduits, and the like disclosed herein may be either rigid, at least partially rigid, flexible, and/or at least partially flexible. Therefore, any such component described herein, whether or not referred to as rigid herein should be interpreted as possibly being at least partially flexible. In accordance with the present disclosure, the rigid elongate tube 110 may be referred to as a 'shaft' for simplicity. Implementation of a valve-repair procedure utilizing the delivery system 100 can be performed in conjunction with certain imaging technology designed to provide visibility of the shaft 110 of the delivery system 100 according to a certain imaging modality, such as echo imaging. Generally, when performing a valve-repair procedure utilizing the tissue anchor delivery system 100, the operating physician may advantageously work in concert with an imaging technician, who may coordinate with the physician to facilitate successful execution of the valve-repair procedure.

In addition to the delivery shaft 110, the delivery system 100 may include a handle 120 having a trigger feature 60, or other actuator, which may be used or actuated to manually deploy a pre-formed knot, such as a bulky knot as described in detail below. The tissue anchor delivery system 100 may further include a trigger lock mechanism 70, which may serve as a safety lock that locks the tissue anchor delivery system until ready for use or deployment of a leaflet anchor as described herein. The trigger 60 may have associated therewith a suture-lock/release mechanism, which may be configured to lock and unlock a pair of suture tails/portions associated with a tissue anchor within and/or to a housing 121 of the handle 120 portion of the system 100.

The system 100 may further comprise a flush port 150, which may be used to de-air the lumen of the shaft 110. For example, heparinized saline flush, or the like, may be connected to the flush port 150 using a female Luer fitting to de-air the valve repair system 100. The term "lumen" is used herein according to its broad and ordinary meaning, and may refer to a physical structure forming a cavity, void, pathway, or other channel, such as an at least partially rigid elongate tubular structure, or may refer to a cavity, void, pathway, or other channel, itself, that occupies a space within an elongate structure (e.g., a tubular structure). Therefore, with respect to an elongate tubular structure, such as a shaft, tube, or the like, the term "lumen" may refer to the elongate tubular structure and/or to the channel or space within the elongate tubular structure.

The lumen of the shaft 110 may house a needle (not shown) that is wrapped at least in part with a pre-formed knot sutureform anchor in a pre-deployment state/configuration, as described in detail herein. In some examples, the shaft 110 presents a relatively low profile. For example, the shaft 110 may have a diameter of approximately 3 mm or less (e.g., about 9 Fr). The shaft 110 is associated with an atraumatic tip 114 feature, referred to in some contexts herein as an "end effector." The atraumatic tip 114 can be an echogenic leaflet-positioner component, which may be used for deployment and/or positioning of suture-type tissue anchors. The atraumatic tip 114, disposed at the distal end of the shaft 110, may be configured to have deployed therefrom a wrapped pre-formed suture knot (e.g., sutureform), as described herein.

In addition to a pre-formed knot sutureform and associated needle, the shaft 110 may house an elongated knot pusher tube (not shown; also referred to herein simply as a "pusher"), which may be actuated using the trigger 60 in some examples. As described in further detail below, the tip 114 provides a surface against which the target valve leaflet may be held in connection with deployment of a leaflet anchor.

The delivery device 100 may be used to deliver a "bulky knot" type tissue anchor, as described in greater detail below. For example, the delivery system/device 100 may be utilized to deliver a tissue anchor (e.g., bulky knot) on a distal side of a mitral valve leaflet. The tip 114 (e.g., end effector), can be placed in contact with the ventricular side of a leaflet of a mitral valve. The tip 114 can be coupled to the distal end portion of the shaft 110, wherein the proximal end portion of the shaft 110 may be coupled to the handle portion 120 of the delivery system 100, as shown. Generally, the elongate pusher (not shown) may be movably disposed within a lumen of the shaft 110 and coupled to a pusher hub (not shown) that is movably disposed within the handle 120 and releasably coupled to an internal drive rod (not shown) actuated by the trigger 60. As described herein, a feature, component, mechanism, or the like, which is described herein as being positioned, located, contained, or otherwise disposed "within" an instrument handle or other component of a medical device, instrument, and/or system, may be understood to be contained or encased within the housing or other structure of the handle (or instrument, device, system), or may be disposed at least partially on the handle, or exposed at least in part through an opening therein, or otherwise associated with the handle. That is, the term "within" may be used for convenience to describe features on and/or in a housing or other referenced structure.

A needle (not shown) carrying a pre-formed tissue anchor sutureform can be movably disposed within a lumen of the pusher and coupled to a needle hub (not shown) that is also releasably coupled to the trigger-actuated drive rod. The trigger 60 can be used to actuate or move the needle and the pusher during deployment of a distally-situated tissue anchor and is movably coupled to the handle 120 in a manner as to allow for a user to manually pull the trigger 60 towards the handle, such as by depressing/pressing an engagement surface 66 of the trigger 60, which may be a blade-type trigger or other type of trigger. For example, the handle 120 may define a channel/slot in which the trigger 60 can be moved, wherein the trigger 60 is configured to actuate a pinion of a rack-and-pinion actuation assembly/system of the handle 120 that causes translation and/or other movement of certain internal components of the system 100. The trigger lock 70 can be used to prevent the trigger 60 from moving within the handle 120 during storage and prior to performing a procedure to deploy a tissue anchor.

The needle may have the pre-formed knot disposed about a distal portion thereof while maintained in the shaft 110. For example, the pre-formed knot may be formed of one or more sutures configured in a coiled sutureform (see image 416 of FIG. 4-4) having a plurality of winds/turns around the needle over a portion of the needle that is associated with a longitudinal slot in the needle that runs from the distal end thereof. Although the term "sutureform" is used herein, it should be understood that such components/forms may comprise suture, wire, or any other elongate material wrapped or formed in a desired configuration. The coiled sutureform can be provided or shipped disposed around the needle. In some instances, two suture tails 95 extend from the coiled sutureform. The suture tails 95 may extend through the lumen of the needle and/or through a passageway of the pusher and/or shaft 110. The coiled sutureform may advantageously be configured to be formed into a suture-type tissue anchor (referred to herein as a "bulky knot") in connection with an anchor-deployment procedure, as described in more detail below. The coiled sutureform can be configurable to a knot/deployed configuration by approximating opposite ends of the coiled portion thereof towards each other to form one or more loops.

The delivery device/system 100 can further include a suture catch/lock mechanism (not shown) disposed within the handle 120 and engageable/actuatable in some manner using the trigger 60. The suture catch/lock may be configured to releasably hold or secure suture tails routed at least partially within the handle 120 during delivery of a tissue anchor as described herein. The suture lock can be used to hold the suture tail(s) with a friction fit or with a clamping force and can have a biased locking mechanism that can be released after the tissue anchor has been deployed/formed into a bulky knot, as described herein.

As described herein, the anchor delivery system 100 can be used in beating heart mitral valve repair procedures. In some instances, the shaft 110 of the delivery system 100 can be configured to extend and contract with the beating of the heart. During systolic contraction, the median axis of the heart generally shortens. For example, with reference to FIG. 1, the distance from the apex 19 of the heart to the valve 6 can vary by about 1 cm to about 2 cm with each heartbeat in some patients. In some instances, the length of the shaft no that protrudes from the handle 120 can change with the length of the median axis of the heart. That is, distal end of the shaft 110 can be configured to be floating such that the shaft can extend and retract with the beat of the heart so as to maintain contact with the target mitral valve leaflet.

Advancement of the delivery system 100 may be performed in conjunction with echo imaging, direct visualization (e.g., direct transblood visualization), and/or any other suitable remote visualization technique/modality. With respect to cardiac procedures, for example, the delivery device 100 may be advanced in conjunction with transesophageal (TEE) guidance and/or intracardiac echocardiography (ICE) guidance to facilitate and to direct the movement and proper positioning of the device for contacting the appropriate target cardiac region and/or target cardiac tissue (e.g., a valve leaflet, a valve annulus, or any other suitable cardiac tissue). Typical procedures that can be implemented using echo guidance are set forth in Suematsu, Y., J. Thorac. Cardiovasc. Surg. 2005; 130:1348-56 ("Suematsu"), the entire disclosure of which is incorporated herein by reference.

FIGS. 3-1, 3-2, 3-3, 3-4, and 3-5 provide a flow diagram illustrating a process 300 for implanting a leaflet anchor 90 in accordance with one or more examples. FIGS. 4-1, 4-2, 4-3, 4-4, and 4-5 provide images of cardiac anatomy and certain devices/systems corresponding to operations of the process 300 of FIGS. 3-1, 3-2, 3-3, 3-4, and 3-5 in accordance with one or more examples. The process 300 may be implemented when a minimally invasive approach is determined to be advisable.

The process 300 may initially involve, as shown as block 302, accessing the heart of a patient in some manner. For example, the process 300 may involve making one or more incisions proximate to the thoracic cavity to provide a surgical field of access. The total number and length of the incisions to be made depend on the number and types of the instruments to be used as well as the procedure(s) to be performed. The incision(s) may advantageously be made in such a manner as to be minimally-invasive. The term "minimally-invasive" is used herein according to its broad and ordinary meaning, and may refer to a manner by which an interior organ or tissue may be accessed with relatively little damage being done to the anatomical structure through which entry is sought. For example, a minimally invasive procedure may involve accessing a body cavity by a small incision of, for example, approximately 5 cm or less made in the skin. The incision may be vertical, horizontal, or slightly curved. If the incision is located along one or more ribs, it may advantageously follow the outline of the rib. The opening may advantageously extend deep enough to allow access to the thoracic cavity between the ribs or under the sternum and is preferably set close to the rib cage and/or diaphragm, dependent on the entry point chosen.

In some implementations, the process 300 may involve accessing the heart through one or more openings made by one or more small incision in a portion of the body proximal to the thoracic cavity, such as between one or more of the ribs of the rib cage of a patient, proximate to the xyphoid appendage, or via the abdomen and diaphragm. Access to the thoracic cavity may be sought to allow the insertion and use of one or more thorascopic instruments, while access to the abdomen may be sought to allow the insertion and use of one or more laparoscopic instruments. Insertion of one or more visualizing instruments may then be followed by transdiaphragmatic access to the heart. Additionally, access to the heart may be gained by direct puncture (e.g., via an appropriately sized needle, for instance an 18-gauge needle) of the heart from the xyphoid region. Accordingly, the one or more incisions should be made in such a manner as to provide an appropriate surgical field and access site to the heart in the least invasive manner possible. Access may also be achieved using percutaneous methods, further reducing the invasiveness of the procedure. See, e.g., "Full-Spectrum Cardiac Surgery Through a Minimal Incision Mini-Sternotomy (Lower Half) Technique," Doty et al., *Annals of Thoracic Surgery* 1998; 65(2): 573-7 and "Transxiphoid Approach Without Median Sternotomy for the Repair of Atrial Septal Defects," Barbero-Marcial et al., *Annals of Thoracic Surgery* 1998; 65(3): 771-4, the entire disclosures of each of which are incorporated herein by reference.

Once the target site for puncture of the heart/ventricle wall 18 is identified, a needle, such as an 18-gauge needle 401 (e.g., trocar) or the like, may be inserted into the target site/ventricle, as shown as block 304. For example, the needle shaft 401 may be pressed/advanced through the heart wall 18 to access the ventricle 3. In some examples, the needle 401 may be a hypodermic needle having an internal axial lumen.

At block 306, the process 300 involves advancing a guidewire 402 through a lumen of the needle 401, to thereby access the ventricle 3 through the needle 401. For example, in some implementations, when the needle 401 penetrates the ventricle 3, a 0.035" guidewire is advanced through the needle under imaging (e.g., TEE) guidance.

At block 308, the process 300 involves proximally withdrawing the needle 401 to thereby remove the needle 401 from the heart wall 18 and from around the guide wire 42. The guidewire 402 is thereby left in place in the heart wall 18 and partially within the ventricle 3. It may be advantageous to relatively slowly remove the needle 401 to prevent injury/damage to the patient anatomy.

At block 310, the process 300 involves placing an introducer 200 over the guidewire 402. For example, the introducer 200 may be distally advanced over the guidewire 402 and advanced into the left ventricle 3. As shown in image 411, the introducer 200 may be inserted with a dilator 228 and passed over the guidewire 402 and advanced into the left ventricle 3. The surgeon/practitioner can use one or more sutures to make a series of stiches in one or more concentric circles in the myocardium at the desired location to create a "purse-string" closure. The "Seldinger" technique, as embodied at least in part in the various steps of the process 300 described above, can be used to access the left ventricle in the area surrounded by the purse-string suture by puncturing the myocardium with the needle 401, with the guidewire 402 implemented in the lumen of the needle/trocar 401, and advancing the introducer 200 over the guidewire 402. Once the introducer 200 is properly placed, the purse-string suture(s) can be tightened to reduce bleeding around the lumen 119 of the introducer 200.

Figures 1, 3:
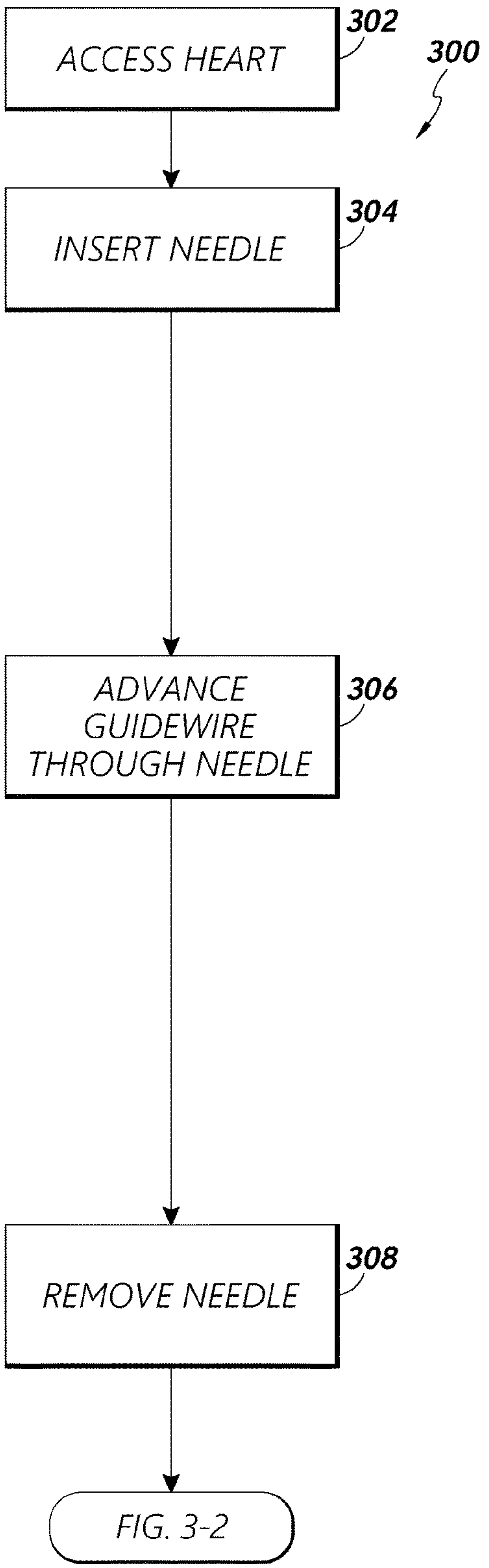
Figures 1, 4:
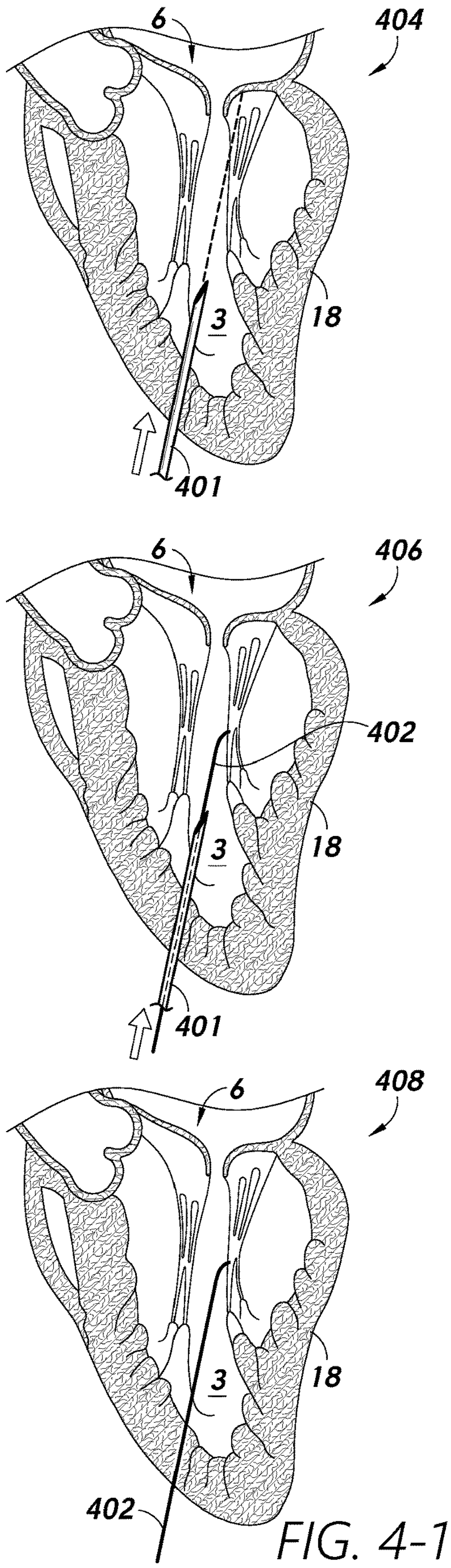
Figures 2, 4:
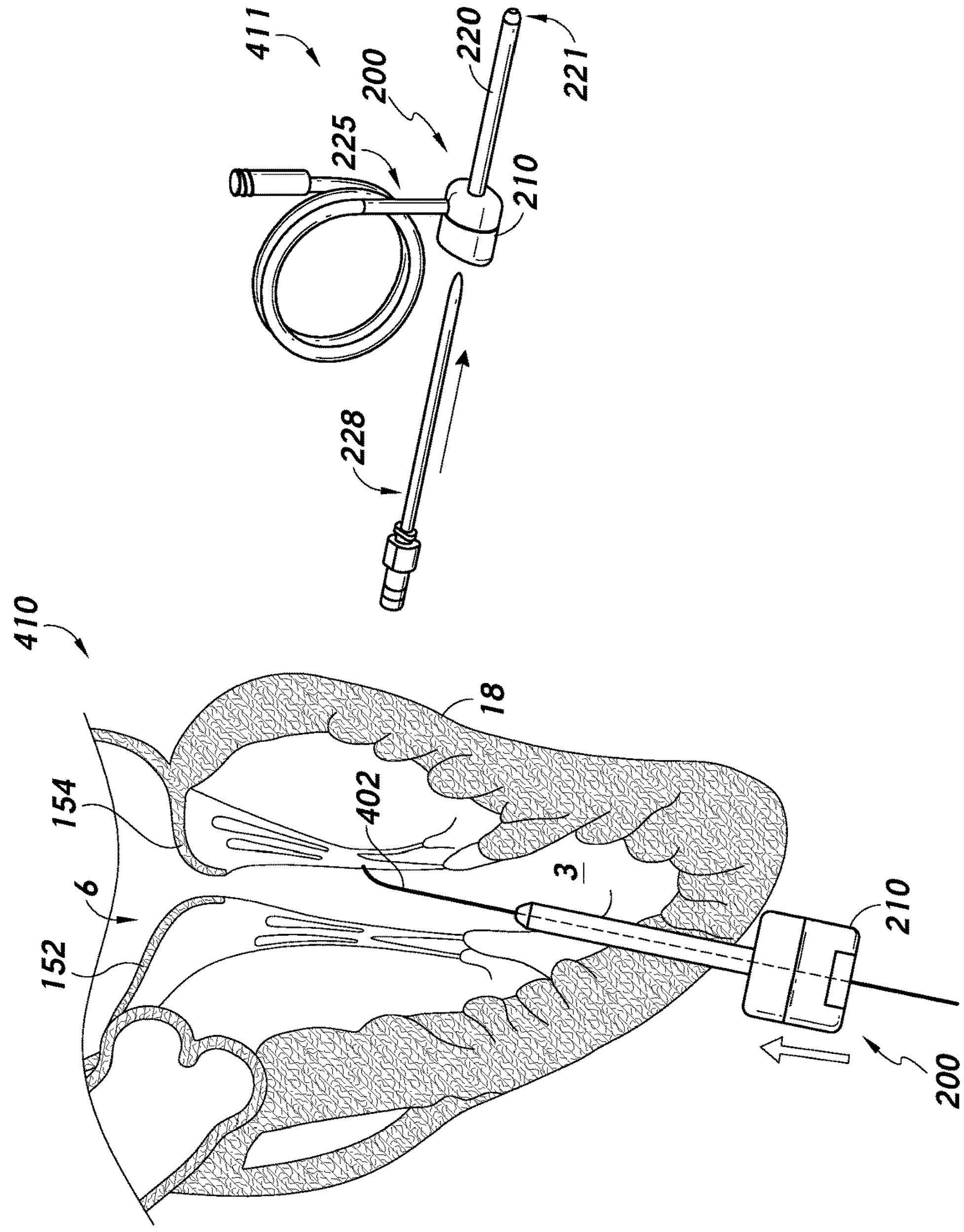
Figure 4:
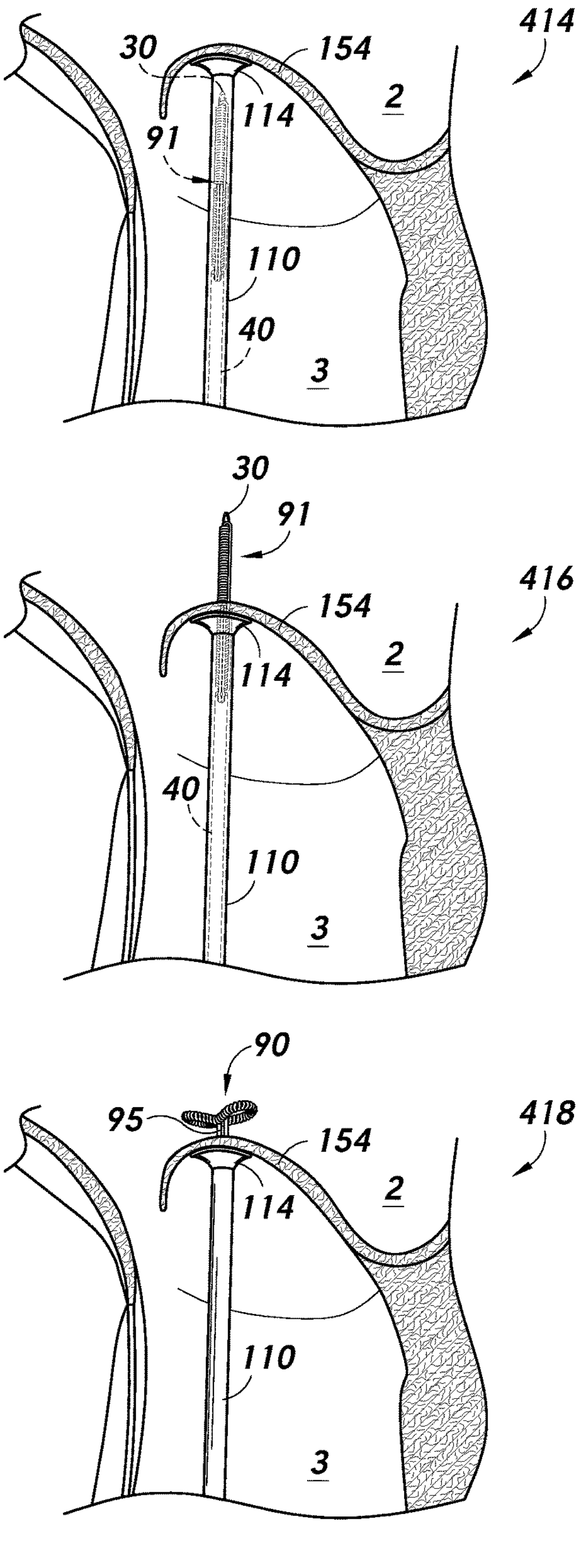

With respect to images 410-413 of FIGS. 4-2 and 4-3, respectively, the introducer/port device 200 may contain one or more fluid-retention valves to prevent blood loss and/or air entry into the ventricle 3. Image 411 shows a perspective view of a dilator 228 and introducer 200 that may be used in the process 300 in accordance with one or more examples. Image 413 shows the introducer device 200 and a tissue anchor delivery device shaft 110 in accordance with one or more examples.

The hemostatic introducer 200 may be inserted into the target ventricle at a tip 221 associated with a lumen 220 of the introducer 200. The lumen 220 of the introducer 200 may be used to guide the shaft 110 of the tissue anchor delivery device/system 100. The body or hub 210 of the introducer 200 may be used to secure the introducer 200 to the pericardium/epicardium of the heart for stable entry of the shaft 110 of the tissue anchor delivery device wo and/or to control the amount of bleed-back during the process 300. In some instances, a female Luer may be used to de-air the introducer 200 through a port 225 prior to use and/or to connect a fluid flush, such as a heparin flush, during the process 300. The dilator 228 may be used to guide the introducer 200 into the target ventricle 3.

The introducer lumen 220 provides a conduit into the target surgical area/chamber 3. In some instances, the introducer 200 comprises one or more hemostasis valves associated with a channel/lumen port 222. Such hemostasis valve(s) may comprise silicone or other flexible material configured to keep blood from flowing out of the channel/lumen port 222. The port 222 may serve as a tissue anchor delivery device lumen insertion port, wherein an inserted delivery device shaft 110 may pass through the lumen 220 of the introducer 200 and out the distal end 221 thereof for access to the target chamber. The port 222 may further be dimensioned to accommodate insertion of the dilator device 228 used to guide the introducer into the target chamber (e.g., left ventricle, off-apex). The distal end 221 of the introducer 200 may have a tapered shape to seal against the delivery system lumen and to reduce trauma from insertion thereof.

Once the introducer 200 is positioned, eyelets (see image 413 of FIG. 4-3) may be sutured to the heart wall 18 and secured to a purse-string tourniquet. At block 312, the process involves inserting a delivery system shaft 110 through a port 222 and lumen 220 of the introducer 200 to access the ventricle 3. In some examples, a sheath may be inserted through the introducer 200, through which the delivery system shaft 110 is advanced. In some implementations, an endoscope may first be advanced through the introducer 200 to visualize the ventricle 3, the valve 6, and/or the sub-valvular apparatus. By use of an appropriate endoscope, a careful analysis of the malfunctioning valve 6 may be performed. Each segment of each leaflet may be carefully assessed to determine its pliability, integrity, and motion. Based on this assessment, the practitioner can determine whether the valve can indeed be repaired or must be replaced. The motion of the target leaflet(s) can be classified as slightly dysfunctional, prolapsed, or restricted and based on this classification, the necessary steps of the repair can be determined.

The shaft 110 may present a relatively low-profile delivery device, which may be dimensioned to fit within the lumen 220 of the introducer 200. For example, the shaft 110 may be a 3 mm (9 Fr) shaft. Furthermore, the tip (e.g., end effector) 114 may advantageously be flexible to allow for insertion into the lumen 220 even where the lumen 220 has a smaller diameter than the extended diameter of the tip 114. The delivery device 100 may be similar to any of the devices/systems described in the '761 PCT Application and/or the '170 PCT Application. The advancement of the device shaft 110 may be performed in conjunction with echo imaging and/or direct visualization (e.g., direct transblood visualization). For example, the delivery device 100 may be advanced in conjunction with transesophageal echocardiogram (TEE) guidance or intracardiac echo (ICE) to facilitate and direct the movement and proper positioning of the device for contacting the appropriate apical region of the heart. Typical procedures for use of echo guidance are set forth in Suematsu.

At block 314, the process 300 involves contacting a target leaflet 154 with the end effector 114 of the delivery system 100. Image 414 of FIG. 4-4 shows the shaft 110 of the tissue anchor delivery device 100 positioned on the target valve leaflet 154 (e.g., mitral valve leaflet). For example, the target site of the valve leaflet 154 may be slowly approached from the ventricle side thereof by advancing the distal end of the shaft 110 along or near to the posterior wall of the ventricle 3 (e.g., left ventricle), without contacting the ventricle wall.

Once the tip 114 is positioned in the desired position, the distal end of the shaft no and the tip 114 may be used to drape, or "tent," the leaflet 154 to better secure the tip 114 in the desired position, as shown in image 414. Draping/tenting may advantageously facilitate contact of the tip 114 with the leaflet 154 throughout one or more cardiac cycles, to thereby provide more secure or proper deployment of leaflet anchor(s). The target location may advantageously be located relatively close to the free edge of the target leaflet 154. Navigation of the tip 114 to the desired location on the underside of the target valve leaflet 154 may be assisted using echo imaging, as described in detail herein. Echo imaging may be relied upon to confirm correct positioning of the tip 114 prior to anchor/knot deployment.

At block 316, the process 300 involves puncturing a needle 30 having a tissue anchor associated therewith through the leaflet 154. For example, with the shaft 110 positioned against the target leaflet 154, the trigger 60 of the tissue anchor delivery device 100 can be actuated to move the needle 30 and a pusher 40 disposed within the shaft 110, such that the coiled sutureform portion 91 of the suture anchor slides off the needle 30. As the trigger 60 is actuated, a distal piercing portion of the needle 30 punctures the leaflet 14 and forms an opening in the leaflet. Image 416 of FIG. 4-4 shows a close-up view of the distal portion of the delivery device shaft 110, showing the needle 30 and tissue anchor sutureform 91 projected at least partially therefrom through the target leaflet 154 in accordance with one or more examples. In some instances, the needle 30 is projected a distance of between about 0.2-0.3 inches (e.g., between about 5-8 mm), or less, distally beyond the distal end of the shaft 110 (e.g., beyond the tip 114). In some instances, the needle 30 is projected a distance of between about 0.15-0.4 inches (e.g., between about 3-10 mm). In some instances, the needle 30 is projected a distance of about 1 inch (e.g., about 2.5 cm), or greater. In some instances, the needle 30 extends until the distal tip of the needle and the entire coiled sutureform 91 extend through the leaflet 14 and/or beyond the distal tip of the shaft 110. Alternatively, the needle extension may be limited to a position in which the coiled sutureform 91 is at least partially disposed within the shaft 110, as shown in image 416. While the needle 30 and sutureform 91 are projected at least partially into the atrial side of the leaflet 154, the shaft 110 and tip 114 advantageously remain entirely on the ventricular side of the leaflet.

As the pusher 40 within the tissue anchor delivery device shaft 110 is moved distally, a distal end of the pusher advantageously moves/pushes the distal coiled sutureform 91 (e.g., pre-deployment coiled configuration of the suture anchor 90) over the distal end of the needle 30 and further within/into the atrium 2 on a distal side of the leaflet 154, such that the sutureform 91 moves distally beyond a distal end of the needle 30. For example, in some instances, at least half a length of the sutureform 91 extends beyond the distal end of the needle 30. In some instances, at least three quarters of the length of the sutureform 91 extends beyond the distal end of the needle 30. In some instances, the entire coiled sutureform 91 extends beyond the distal end of the needle 30.

At block 318, the process 300 involves deploying/forming the pre-deployment sutureform 91 into a retention tissue anchor configuration 90 on the atrial side of the leaflet 154. For example, after the sutureform 91 has been pushed off of the needle 30, pulling one or more of the suture tail(s) 95 (e.g., suture strands extending from the coiled portion of the suture) associated with the tissue anchor sutureform 91 proximally can cause the sutureform 91 to form a bulky knot anchor 90, as shown in image 418, which provides a close-up view of the formed suture anchor 90 on the atrial side of the leaflet 154. For example, the bulky knot suture anchor 90 may be formed by approximating opposite ends of the coils of the sutureform 91 towards each other to form one or more loops.

At block 320, the process 300 involves withdrawing the delivery system 100 and fixing/tying the artificial chordae/sutures associated with the tissue anchor 90 to the heart wall 18, to thereby tether the leaflet 14 to the heart wall 18 for the purpose of reducing or preventing leaflet prolapse. For example, after the sutureform 91 has been formed into the bulky knot 90, the delivery device 100 can be withdrawn proximally, leaving the tissue anchor 90 disposed on the distal atrial side of the leaflet 154. In some instances, two suture tails 95 may extend from the proximal/ventricle side of the leaflet 14 and out of the heart. For example, the delivery device shaft 110 can be slid/withdrawn over the suture tail(s) 95. With the tissue anchor 90 deployed, suture tails 95 coupled to the tissue anchor 90 run through the elongated shaft 110 and into the handle 120 of the device/system 100 prior to withdrawal of the delivery system off of the suture tail(s) 95.

The suture tails 95 may be tied/secured to the heart wall 18 to tether the leaflet 154 to the heart wall. The tissue anchor 90 and suture tails 95 effectively function as replacement chordae tendineae to improve the function/closure of the valve leaflets. The image 420 shows the tissue anchor 90 deployed with the suture tails 95 tethering the leaflet 154 to the heart wall 18, with the delivery system 100 having been withdrawn from over the sutures 95 and out of the heart 1.

The suture tails 95 coupled to the anchor 90 may be secured at the desired tension using a pledget 71 or other suture-fixing/locking device or mechanism on the outside of the heart through which the suture tails 95 may run. Furthermore, one or more knots or other suture fixation mechanisms or devices may be implemented to hold the sutures at the desired tension and to the pledget 71. With the suture tail(s) 95 fixed to the ventricle wall 11, a ventricular portion 95 of the suture tail(s) 95 may advantageously function as replacement leaflet cords (e.g., chordae tendineae) that are configured to tether the target leaflet 14 in a desired manner. In certain implementations, testing of location and/or tension of the anchor and/or suture tail(s) 95 may be performed by gently tensioning the suture tails until leaflet motion is felt and/or observed. Echo imaging technology may be used to view and verify the anchor placement and resulting leaflet function.

Although the procedures described herein are with reference to repairing a cardiac mitral valve or tricuspid valve by the implantation of one or more leaflet anchors and associated cord(s), the methods presented are readily adaptable for various types of tissue, leaflet, and annular repair procedures. The methods described herein, for example, can be performed to selectively approximate two or more portions of tissue to limit a gap between the portions. That is, in general, the methods herein are described with reference to a mitral valve but should not be understood to be limited to procedures involving the mitral valve.

The steps and processes outlined above for placing a suture-knot-type tissue anchor may be repeated as necessary until the desired number of anchors have been implanted on the target valve leaflet(s). For example, a plurality of leaflet anchors can be deployed in each of the mitral valve leaflets. In some implementations, sutures/cords coupled to separate leaflets may be secured together in the heart by tying them together with knots or by another suitable attachment device, creating an edge-to-edge repair to decrease the septal-lateral distance of the mitral valve orifice.

Figures 2, 3:
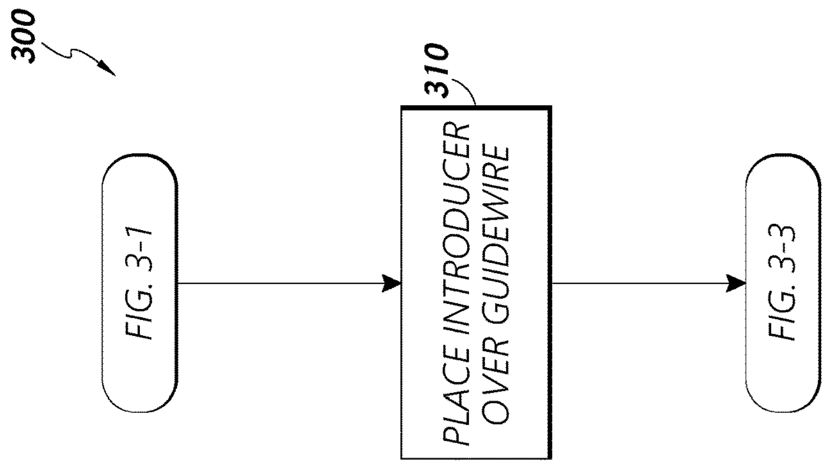
Figures 3, 4:
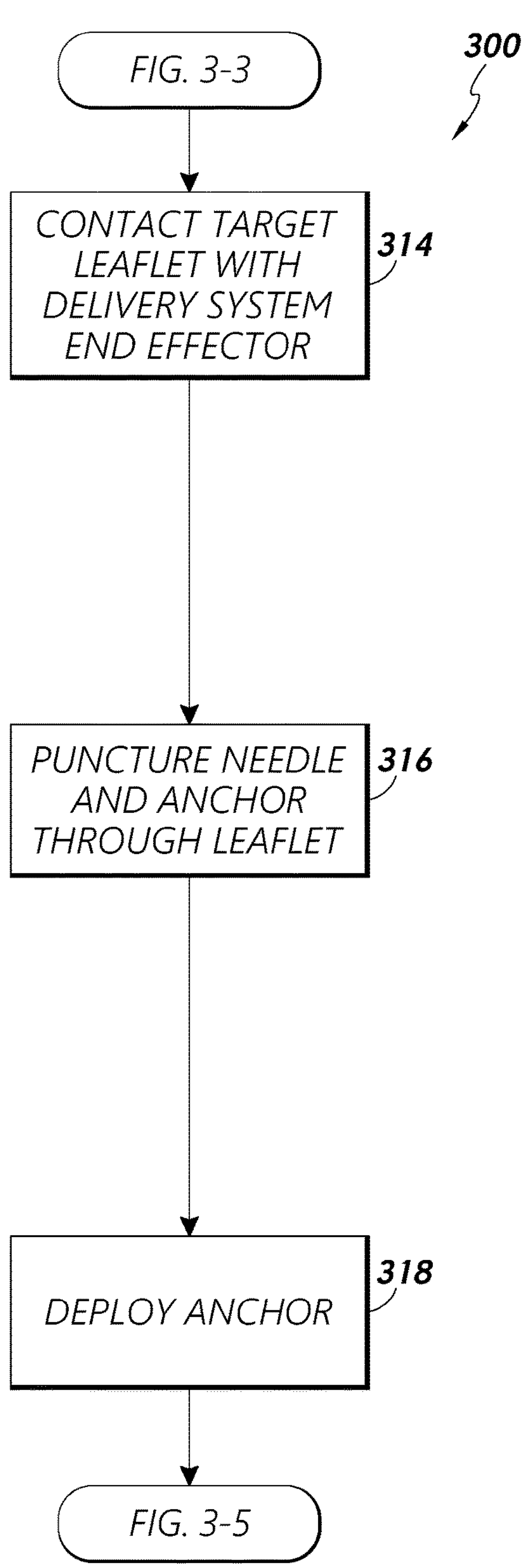
Figures 3, 4, 5:
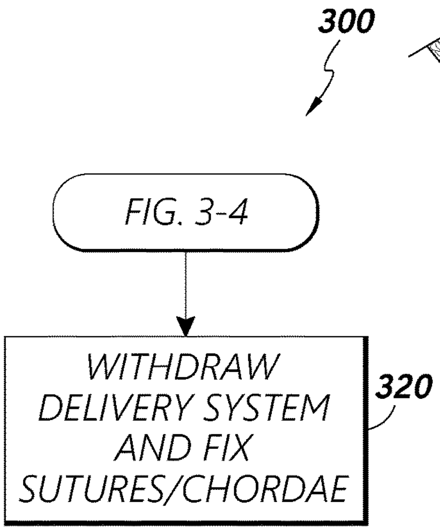
Figures 4, 5:
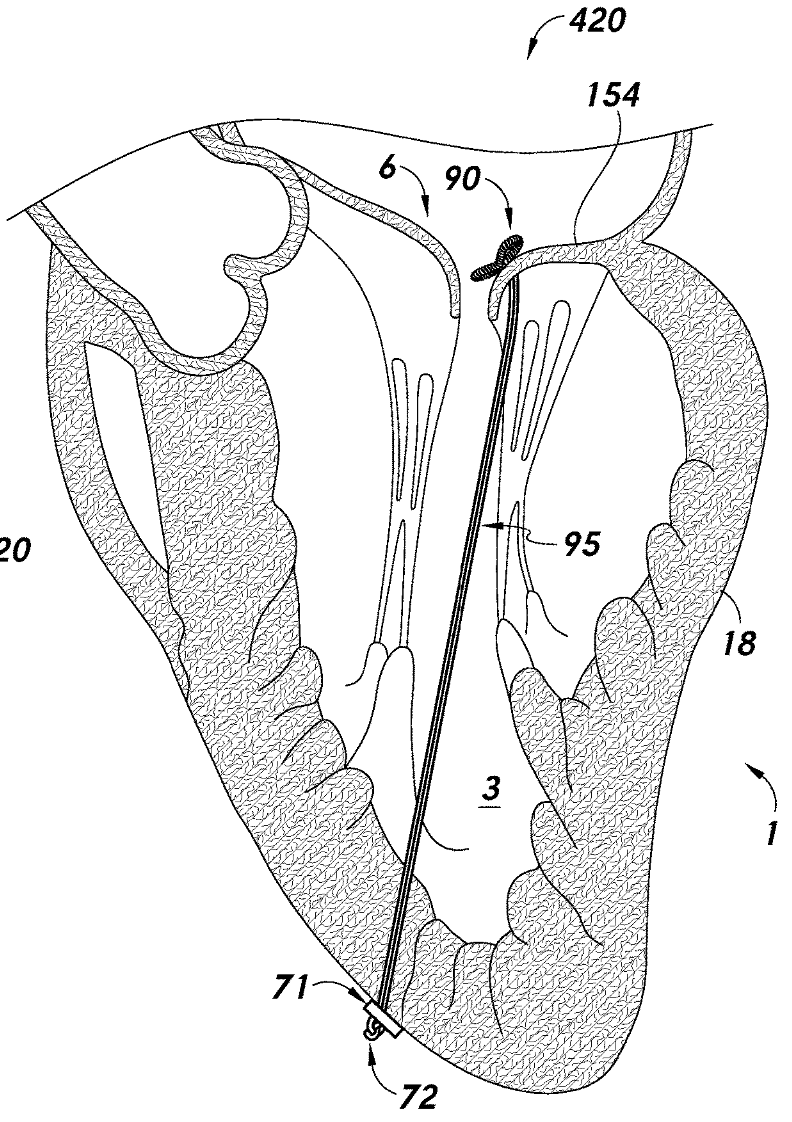
Figures 1, 5:
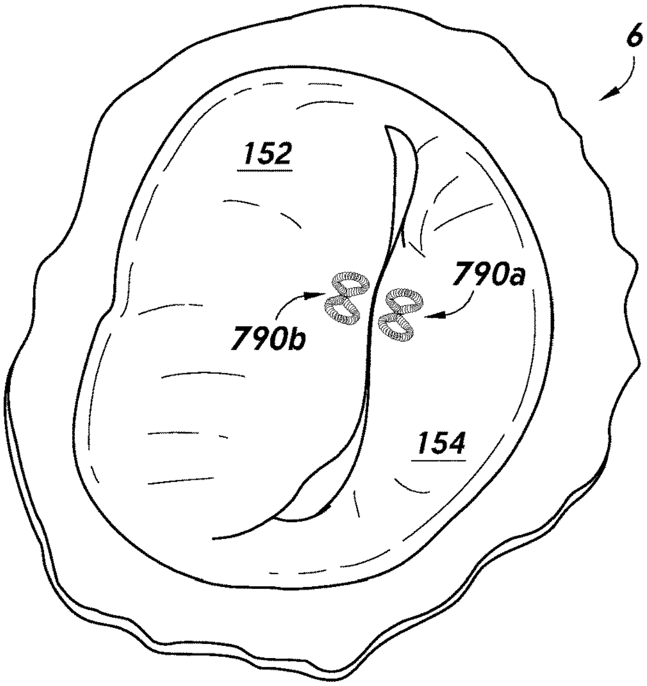
Figures 2, 5:
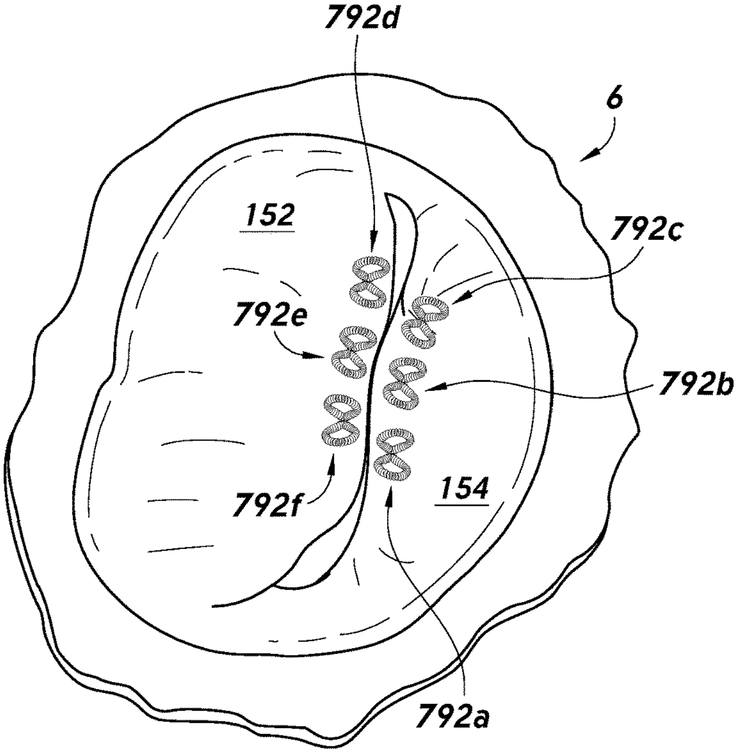

FIG. 5-1 illustrates an atrial/distal side of a valve (e.g., viewing the mitral valve 6 from the left atrium 2) having a plurality of tissue anchors deployed therein according to one or more instances disclosed herein. FIG. 5-1 shows two tissue anchors 790 with a bulky knot form deployed on the atrial/distal side of the valve 6. As shown in FIG. 5-1, a first tissue anchor 790*a* may be deployed on a first leaflet 154 and/or a second tissue anchor 790*b* may be deployed on a second leaflet 152. However, any number of tissue anchors may be deployed on either leaflet. For example, the first tissue anchor 790*a* and second anchoring element 790*b* may alternatively both be delivered to the first leaflet 154 or the second leaflet 152.

FIG. 5-2 illustrates a view of an atrial/distal side of a valve 6 having six tissue anchors 792 deployed therein according to one or more examples. In some instances, the six anchoring elements 792 may be delivered simultaneously via a single delivery device (e.g., a needle) and/or may be deployed sequentially. As shown in FIG. 5-2, a first tissue anchor 792*a*, second tissue anchor 792*b*, and/or third tissue anchor 792*c* may be delivered to a first leaflet 154 and/or a fourth tissue anchor 792*d*, fifth tissue anchor 792*e*, and/or sixth tissue anchor 792*f* may be delivered to a second leaflet 152. However, any number of tissue anchors 792 may be delivered to either leaflet.

The appropriate number of leaflet anchors may advantageously be determined to produce the desired coaptation of the target valve leaflets 154, 152. Some or all deployed leaflet anchors may advantageously be below the surface of coaptation. With respect to posterior mitral valve leaflet repair, the anterior leaflet 152 may advantageously touch the posterior leaflet 154 basal to the leaflet anchor(s). In some implementations, tension adjustment in the suture tail(s)/cord(s) associated with multiple leaflet anchors may be performed simultaneously. For example, a pledget may be drawn against the epicardial surface, and all the suture tails/cords may be inserted through a tourniquet so that all cords can be tension to the desired effective coaptation together.

Trigger-Based Tissue Anchor and Suture Working/Management

Tissue anchor delivery devices/systems as described herein advantageously provide a stable platform for deployment of tissue anchors, such as knot-type tissue anchors as described above, wherein such stability may reduce the instances/risk of device tip (e.g., end effector) movement during a tissue anchor deployment procedure. With respect to tissue anchor deployment devices including handle portions, as described above, position readjustment and/or motion during deployment can result in undesirable movement of the elongate shaft and/or tip thereof. Generally, tip movement during deployment procedures can result in consequential loss of contact of the device tip/end-effector with the mitral valve leaflet or other target tissue and/or can result in the placement of a tissue anchor in an undesired location. Trigger-based devices/systems, as described in detail below, include aspects that mitigate tip movement during tissue anchor deployment formation and device/system withdrawal at least in part by allowing for a single stroke/pull of a trigger actuator to seamlessly actuate needle, pusher, and/or suture-tensioning and/or -locking components in a manner as to implement various stages of the tissue anchor deployment processes disclosed herein (e.g., process 300 described above).

Figure 6A:
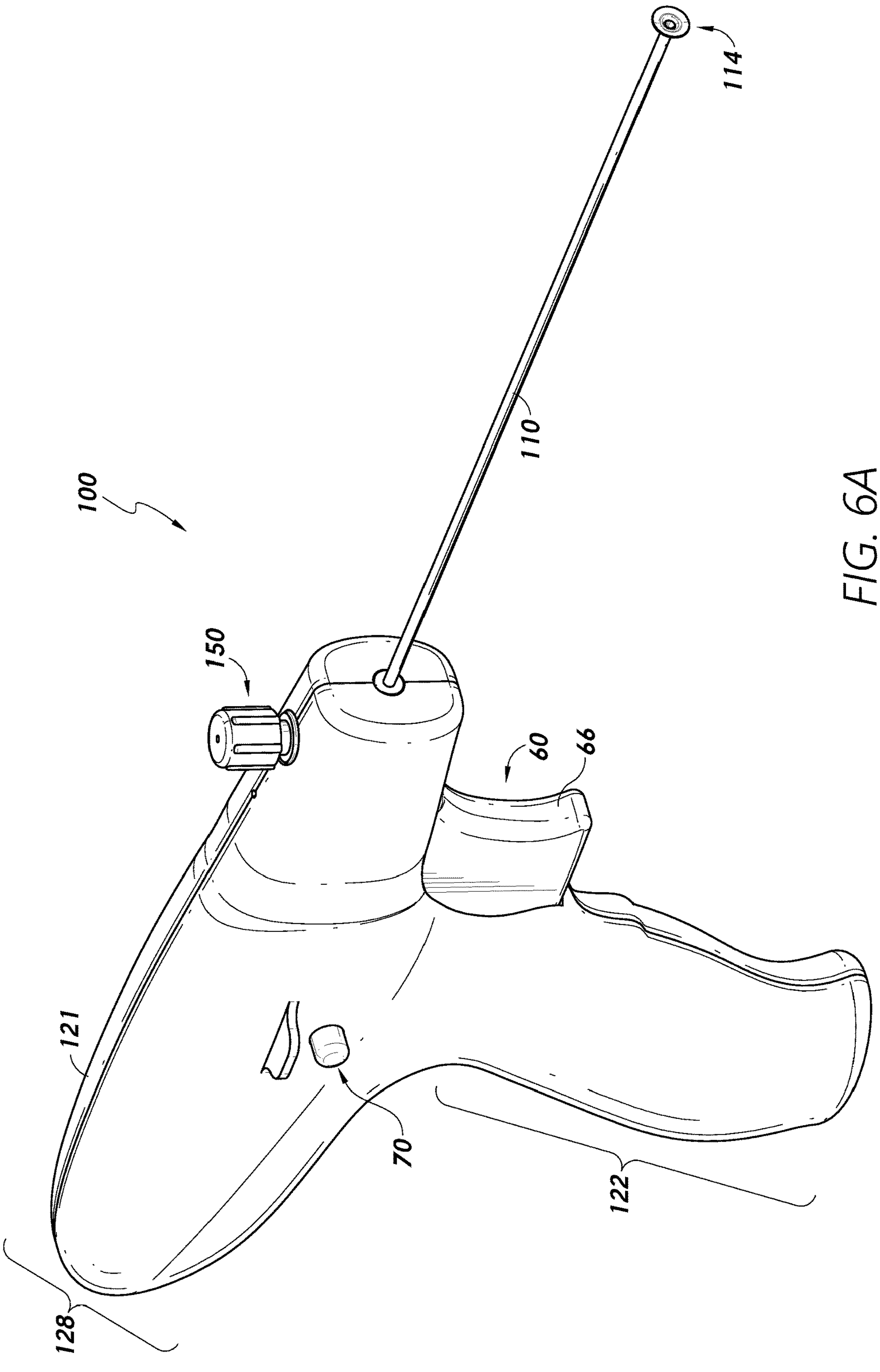
FIGS. 6A and 6B show perspective and side views, respectively, of a tissue anchor delivery device comprising a trigger actuator in accordance with one or more examples.
Figure 6B:
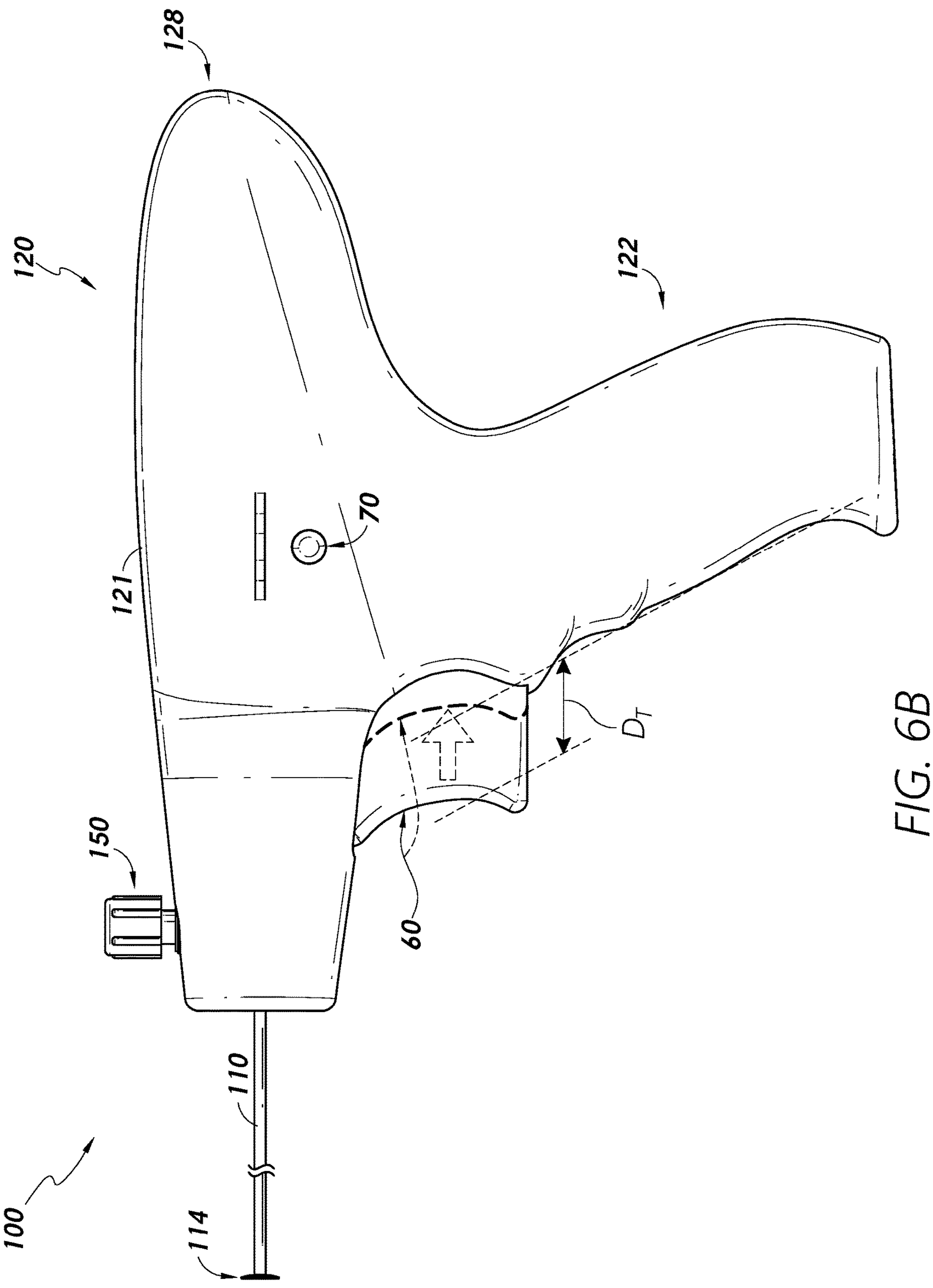
Figures 1B, 7:
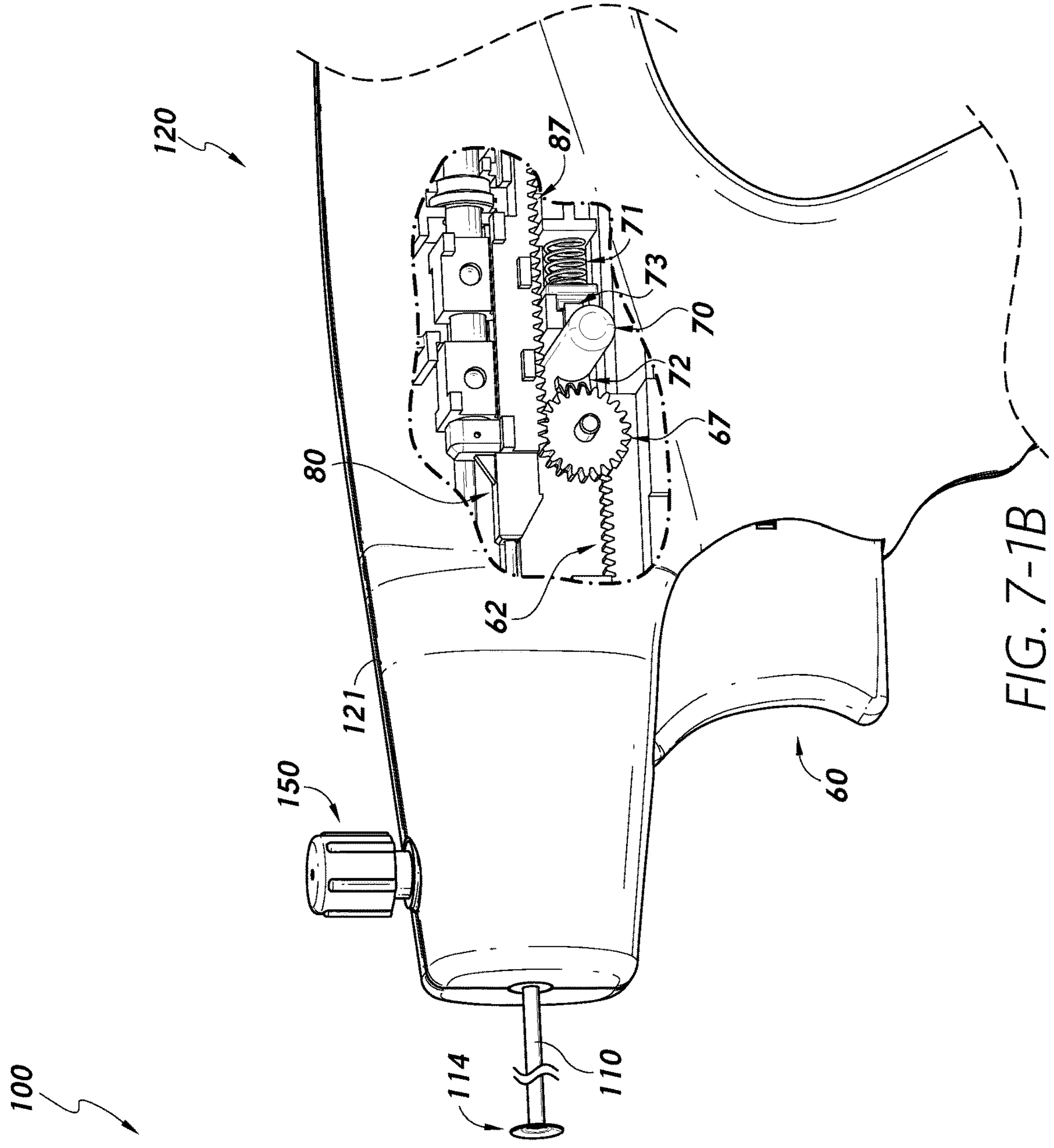
Figures 1A, 7:
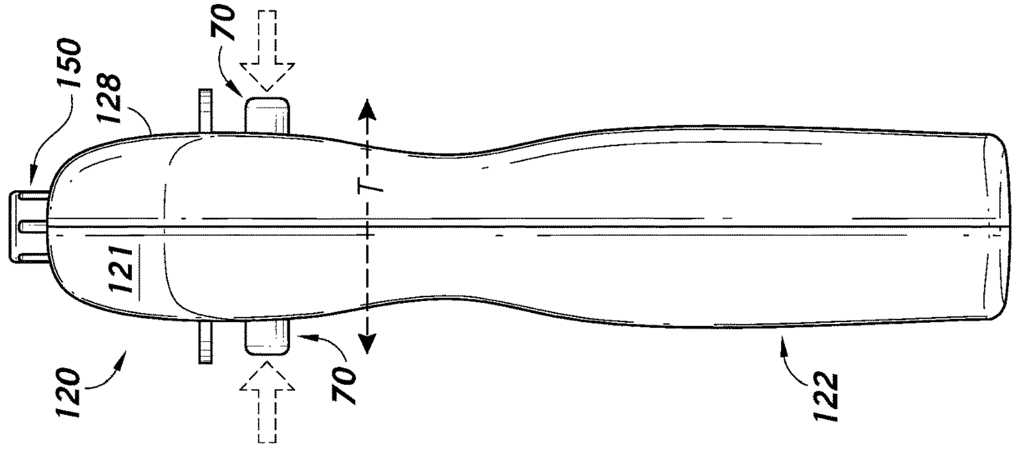
FIGS. 7-1A and 7-2A show a handle of a tissue anchor delivery device with a trigger lock thereof in locked and unlocked configurations, respectively, in accordance with one or more examples.
Figures 2B, 7:
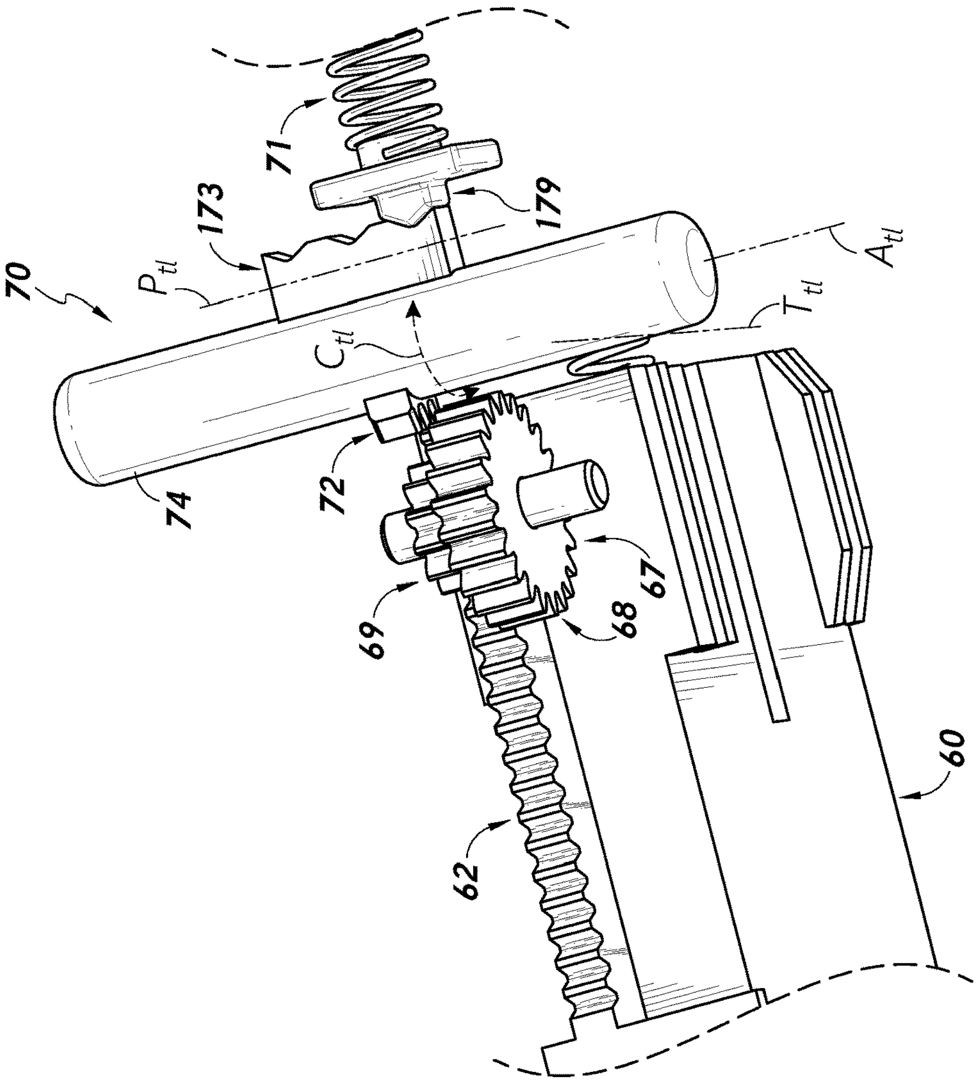
Figures 2A, 7:
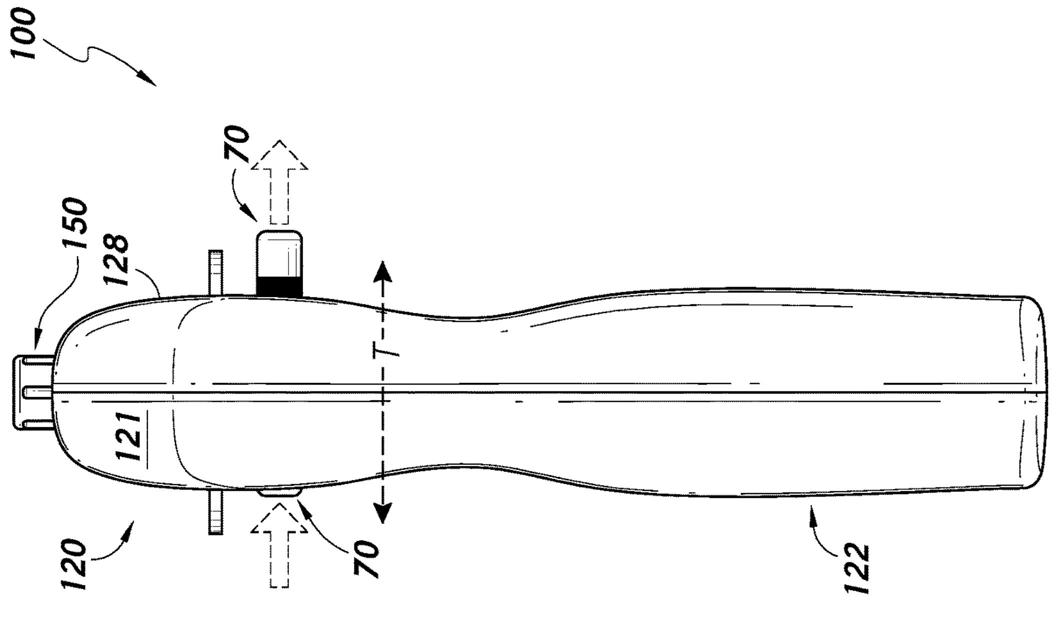
Figure 8A:
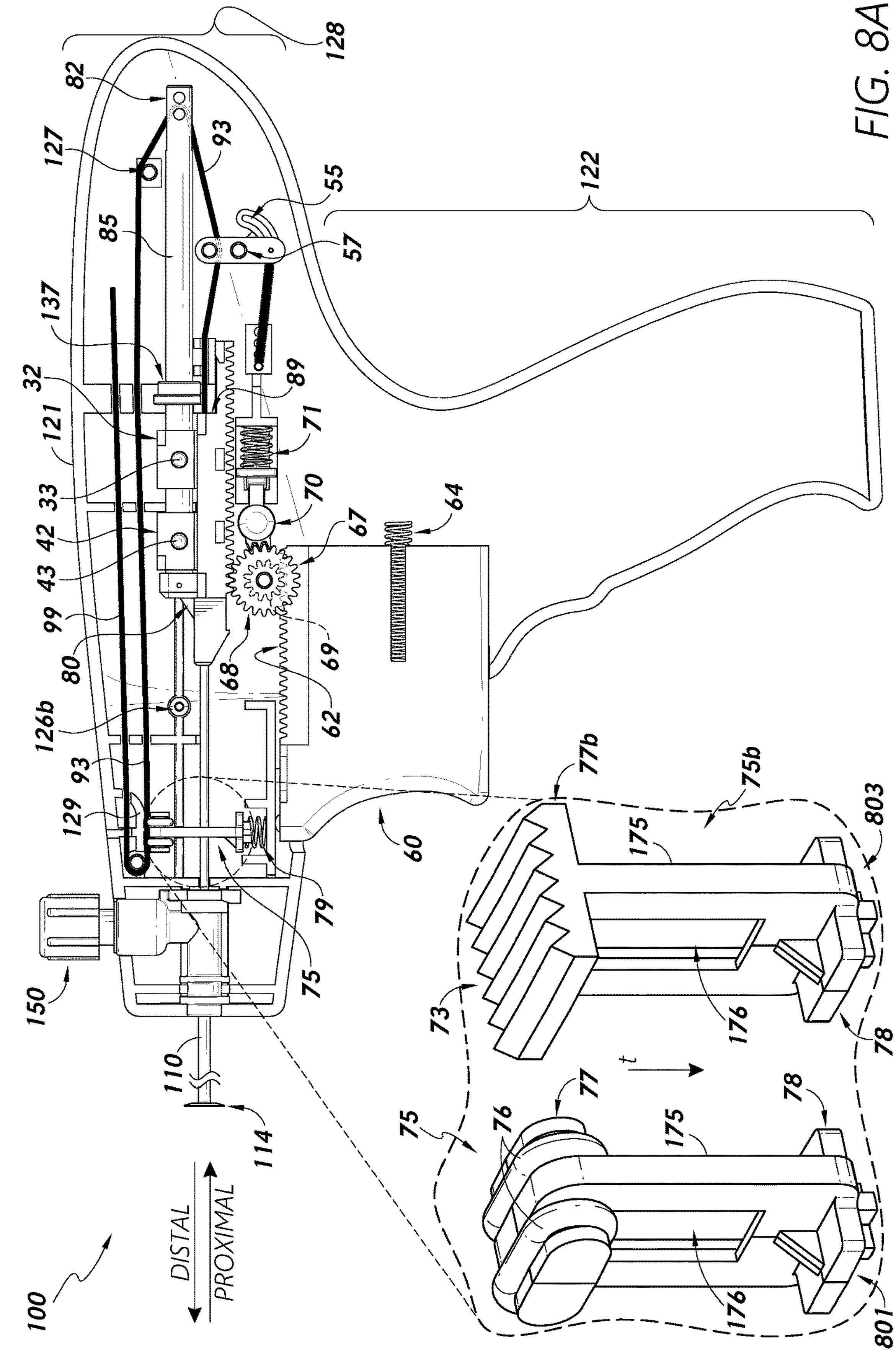
FIGS. 8A and 8B show side cutaway and exploded views, respectively, of a tissue anchor delivery device in accordance with one or more examples.
Figure 8B:
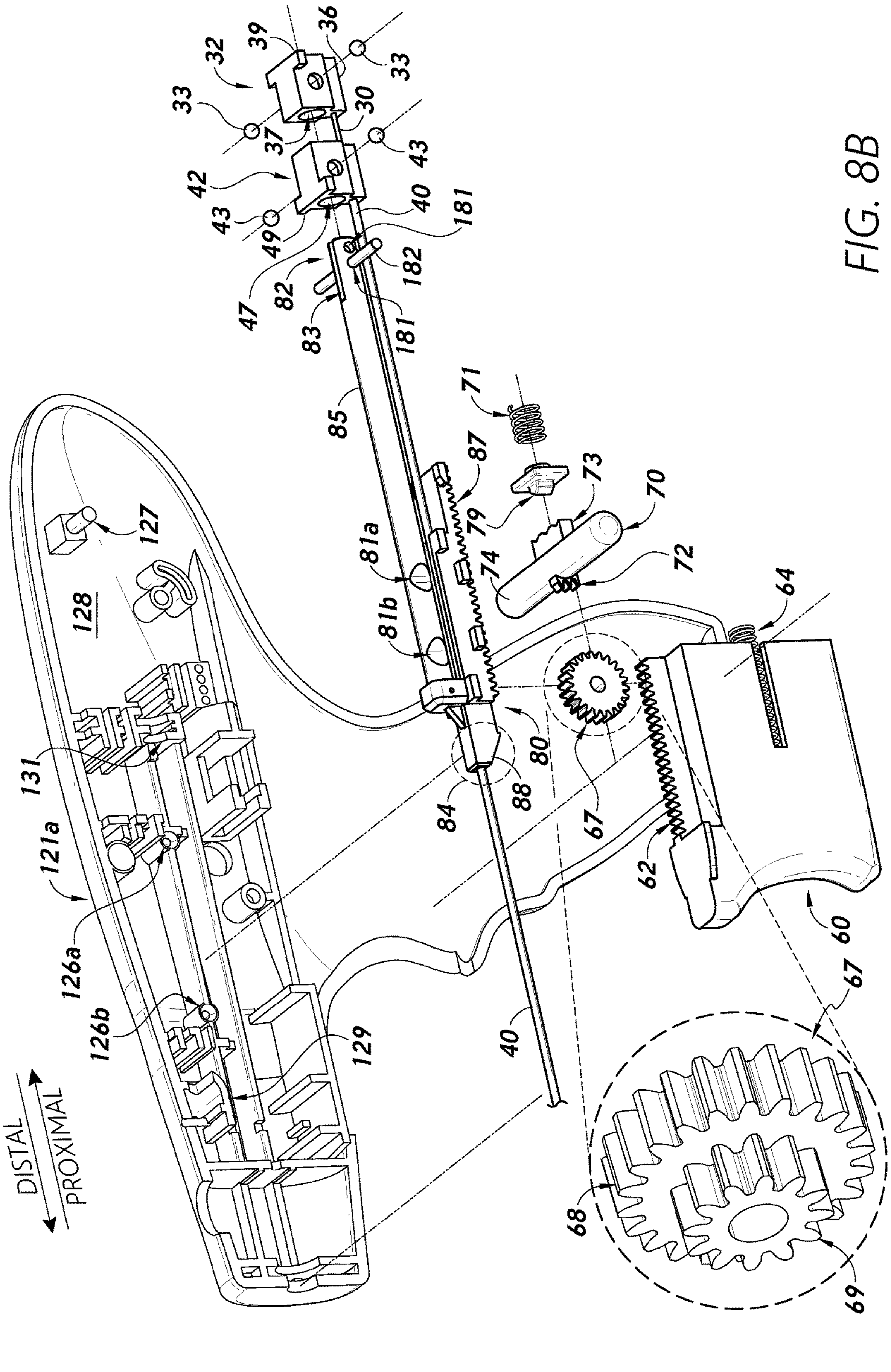

FIGS. 6A and 6B show perspective and side views, respectively, of a tissue anchor delivery device wo comprising a trigger actuator 60 in accordance with one or more examples. FIGS. 7-1A and 7-2A show a handle 120 of a tissue anchor delivery device with a trigger lock 70 thereof in locked and unlocked configurations, respectively, in accordance with one or more examples. FIGS. 7-1B and 7-2B show detailed images of the trigger lock 70 associated with FIGS. 7-1A and 7-2A in locked and unlocked configurations, respectively, in accordance with one or more examples. FIGS. 8A and 8B show cutaway side and exploded views, respectively, of a tissue anchor delivery device 100 in accordance with one or more examples.

The tissue anchor deployment device wo is configured with a trigger-based deployment mechanism configured to actuate certain components of the device 100 to deliver, deploy, and form tissue anchors in a relatively stable and controlled manner. The trigger actuator system may incorporate a dual rack-and-pinion mechanism to translate trigger pull/movement into advancement/translation of one or more internal (e.g., disposed at least partially within the handle 120) and/or external components to deliver and form tissue anchor(s) (e.g., bulky not tissue anchor(s)).

The device/system 100 includes a trigger actuator 60, which may be spring-loaded/biased in some implementations. For example, the device wo may include a spring 64 configured to resist pulling/actuation (e.g., in the proximal direction, to the right with respect to the orientation of FIG. 8A) of the manually-pressable trigger 60, which may provide a safety mechanism for preventing premature or undesirable actuation of the trigger 60 and/or may bias the trigger 60 to return to a non-engaged configuration when not actively being pulled by the user.

The trigger 60 has associated therewith a first rack 62 that is coupled, integrated, and/or otherwise associated with the trigger 60 in a manner such that the rack 62 (referred to herein as a "trigger rack") is translated together with translation of the trigger 60. For example, in some examples, both the trigger 60 and the rack 62 associated therewith may be drawn proximally along a path that is parallel with the axis of the shaft 110 when the trigger 60 is pulled. As shown, the rack 62 may be integrated with an upper edge or portion of the trigger structural form 60 with respect to the upright orientation shown in FIG. 8B. However, it should be understood that trigger rack 62 translation/actuation may be along any path or trajectory in accordance with aspects of the present disclosure. The trigger rack 62 may be positioned and configured to engage with a pinion gear 67. For example, the trigger rack 62 may include a plurality of teeth/cogs designed to mesh/engage with corresponding teeth/cogs of the pinion gear 67.

The device/system 100 further comprises a mechanical carrier component/structure 80, which may likewise include a rack configured to engage with the pinion gear 67. For example, the carrier 80 may include a second rack 87 (referred to herein as a "carrier rack") comprising a plurality of teeth/cogs configured to mesh with teeth/cogs of the pinion gear 67. For example, as illustrated, the carrier rack 87 may be positioned above the pinion 67 and/or trigger rack 62 (with respect to the orientation of FIG. 8A) and may likewise be configured to translate/advance along a path/ trajectory that is parallel with the elongate shaft 110 and/or the translation path of the trigger 60. With the trigger rack 62 and carrier rack 87 positioned on opposite sides of the pinion gear 67, such rack components may advance/translate in substantially opposite directions in response to rotation of the gear 67.

In some implementations, the pinion gear 67 may comprise a compound gear including two separate gear cylinders, one such gear cylinder/portion 69 having a smaller diameter than a second, wider gear cylinder/portion 68. Each gear portion 68, 69 may combine/mesh with a separate one of the racks 62, 87 in two separate gear pairs/pairings. Each gear pair can have a separate gear ratio, wherein a shared axle connects the pairs to each other. In the rack-and-pinion compound gear system/assembly shown, the trigger rack 62 and associated gear portion of the gear 67 serve as the driving gear. The difference in diameter between the wider gear portion 68 and the narrower gear portion 69 provides a gear reduction, which may allow for a relatively short trigger pull distance to equate to a substantial amount of linear translation of the carrier 80.

The gear ratio of the trigger gear cylinder/portion 69 to the carrier gear cylinder/portion 68 may be designed to translate/correlate a travel distance D t of the trigger 60 between a non-engaged in fully-engaged position (see FIG. 6B) into a desired translation distance of the carrier 80 in order to optimize trigger travel and force required to deploy the tissue anchor(s). For example, the compound gear 67 can include a first gear pair including the trigger rack 62 and the narrower gear cylinder/portion 69 of the pinion gear 67, as well as a second gear pair including the carrier rack 87 and the wider gear cylinder/portion 68 of the gear 67. Combining the trigger rack 62 with the narrower gear portion 69 and the carrier rack 87 with the wider gear portion 68 can serve to translate relatively shorter translation of the trigger 60 into a relatively greater/longer translation distance of the carrier 80, which may be desirable to increase ease of use, wherein greater carrier translation and internal component movement is achieved with relatively less pull distance required from the user. However, it should be understood that examples of the present disclosure may be implemented with the trigger rack 62 combined/meshed with the wider gear portion 68 and the carrier rack 87 combined/meshed with the narrower gear portion 69. Furthermore, in some examples, the pinion gear 67 is not a compound gear, but rather the trigger 62 and carrier 87 racks may be combined/meshed with a common gear portion/cylinder, such that the translation distance of the trigger 60 results in a similar translation distance of the carrier 80. References herein to the trigger 60 may refer to the entire trigger group/assembly, or to a blade portion thereof.

The tissue anchor deployment device 100 may further include certain internal and/or external components configured to provide suture management functionality. For example, during advancement of the shaft 110 to the target tissue (e.g., a valve leaflet), it may be necessary or desirable to maintain tension in the suture tails emanating from and/or otherwise associated with a tissue anchor being deployed, while such suture tails are disposed at least partially within the elongate shaft 110 and handle 120 of the device/system 100, in order to avoid the risk of the suture tail(s) becoming tangled, uncoupled, or otherwise migrating or interfering with other components within the delivery system 100 and/or handle 120 during delivery/deployment. Such components may include a suture lock feature 75, which may be disposed at least partially within the handle 120.

With further reference to the suture lock feature 75, it may be desirable to lock/fix the suture tail(s) within/to the delivery system 100 and/or handle 120 in some manner prior to anchor deployment. However, the handle 120 and shaft 110 may need to be able to slide over and off of the suture tail(s) after deployment. Therefore, after deployment of one or more tissue anchors, the associated suture tail(s) may need to be unfixed/unlocked from the delivery system/ handle. In some solutions, locking and/or unlocking of sutures in/to a delivery system can be cumbersome for the surgeon and/or affect the precision of aspects of the procedure. The device/system 100 advantageously can include an anchor deployment actuator (e.g., trigger 60 and/or carrier 80) that is configured to automatically unlock and/or lock internally- and/or externally-routed suture tail(s) at stage(s) of actuation of the actuator 60.

The trigger actuator 60 can be configured to actuate a pusher 40 that pushes a tissue anchor (e.g., knot-type sutureform that comprises loops of suture that are integrated with the suture tail(s)) to deploy the tissue anchor. As shown, the actuator 60 can cooperate with and/or include a rack-and-pinion assembly/actuator configured to rotate the circular gear/pinion 67 that engages the linear gear/rack 87 of the carrier 80 that includes a feature 84/88 that displaces the suture-locking mechanism 75 as the actuator 60 is actuated to unlock the suture tail(s). The actuator 60 can be configured to tension the suture(s) as it moves, to thereby form a knot tissue anchor into a retention form. The actuator 60 can be configured to lock the suture lock mechanism 75 in the unlocked state when the suture tail(s) is/are unlocked. Such locking mechanism 75 can further be configured to lock the actuator 60 in the fully-actuated position after the suture lock 75 has been unlocked. For example, the carrier 80, which is mechanically coupled to the trigger 60, can comprise a notch/lip that restrains a portion of the suture lock once it advances a certain distance over and/or through the suture lock 75.

The suture lock 75 may be configured to trap/hold a proximal portion 93 of the suture tail(s) in a secured position. For example, the suture lock 75 may include a toggle/ plunger feature that is spring-biased with a spring 79 towards a locked position in which a suture contact head 77 of the suture lock 75 is pressed against a surface of the handle 120, such as a surface 129 of the housing of the handle 120, as shown. The head 77 may press against the suture(s) 93 and sandwich the suture(s) 93 between the head 77 and the surface 129 of the handle/housing. The suture contact head 77 may press/pin the suture(s) 93 against the contact surface 129 to thereby prevent movement of the suture(s) 93 due to frictional force and pressure exerted thereon by the suture lock head 77.

The suture lock head 77 may be designed to exert frictional force/pressure on the suture tail(s) 93 in any suitable or desirable manner. For example, in some examples, the lock head 77 may have associated therewith certain resiliently-compressible material 76, wherein the spring 79 pushing on the toggle/mallet 75 compresses the compressible material/members 76 against the suture tail(s) 93 and/or opposing surface 129, thereby holding/retaining the suture tail(s) 93. The compressible member(s) 76 may comprise any type of material, such as rubber or other polymer. In some examples, as shown in FIG. 8A, the head 77 of the locking plunger/mallet 75 may have one or more rubber bands/rings 76 wrapped about portion(s) thereof, as shown in detailed image 801.

In some examples, the suture contact head/portion 77 of the suture lock 75 may not comprise compressible material. For example, the suture-contact head 77*b* may include teeth 73, as shown in alternative detailed image 803 of the suture lock 75*b*, or other similar features designed to increase frictional force between the suture lock 75 and the opposing contact surface 129 to thereby retain the suture tail(s) 93 in the locked position. The suture lock 75 may be maintained in the locked position shown in FIG. 8A until and unless the carrier 80 advances to a position where a nose portion 84 thereof overcomes the biasing force of the spring 79 to displace the plunger/mallet 75 in a direction away from the contact surface 129, thereby releasing the suture tail(s) 93 from the locked compression. Further details relating to the locking and unlocking of the suture lock 75 using the carrier 80 are described below. The structure 175 physically coupling the base portion 78 of the suture lock to the head portion 77 of the suture lock may be referred to as the "body," or "body portion" of the lock 75. In some examples, the body 175 of the lock 75 includes an aperture/channel 176 through which the nose 84 of the carrier 80 can pass when displacing the lock 75 and/or base 78 in the transverse dimension t.

FIG. 8A shows the suture tail(s) 93 routed within the handle 120 through various components and ultimately through/by the suture lock 75. For example, the suture tail(s) 93 may pass through the shaft 110 and/or pusher 40 and may emanate from the pusher/hub 40/42 within the handle housing 121 and may pass through an engagement/routing feature 82 of the drive rod 85, such that the translation of the drive rod may affect the tension in the suture tail(s) 93. In some examples, the suture tail(s) 93 pass through the needle 30 and/or a needle hub 32 associated therewith.

The suture lock 75 may help prevent uncoupling or migration of the suture tail(s) 93 prior to deployment of the tissue anchor, after which it may be desirable to unlock the suture tail(s) 93 to allow for disengagement with the handle 120 and device wo for withdrawing of the device wo from the suture tail(s) 93. As it may be necessary or desirable for the shaft 110 and handle 120 to be withdrawn/slid over and off of the suture tail(s) 93 after deployment of the tissue anchor(s), at least partial automation of the unlocking of the suture tail(s) in connection with particular state(s) of actuation of the trigger 60 can provide safety and/or ease-of-use benefits.

The handle 120 may include a mechanism 70 for locking the trigger actuator 60. For example, such locking may be desirable to prevent premature deployment of needle, pusher, and/or suture-tensioning components/portions of the system 100. For example, when handling the system 100 prior to insertion into the patient and/or advancement to the target implantation site, premature actuation/translation of components of the system 100, which may cause advancement or other manipulation of certain needle, suture, and/or pusher components that are designed to be deployed/actuated at particular intervals, may be damaging and/or otherwise detrimental to the patient and/or device 100. Furthermore, premature trigger actuation may interfere with the ability to complete a procedure using the system 100. The trigger lock 70 serves to reduce the risk of such premature trigger actuation.

The trigger lock 70 may be coupled to the handle 120 and positioned in a manner as to allow for manual manipulation thereof by a user to engage or disengage the locking feature 70. For example, the trigger lock 70 may be positioned such that it is reachable/accessible using a thumb or other digit of the user's hand when the user is holding the handle 120 with one or more fingers wrapped/holding a finger-grip portion 122 of the handle. Therefore, the position of the lock 70 directly above the finger-grip portion 122 and/or trigger 60 may be advantageous with respect to ease-of-use.

The trigger lock 70 may have a peg-type form, as shown, wherein transverse depression/pressing/pulling (e.g., in the direction/dimension T identified in FIGS. 7-1A and 7-2A) of the peg/button portion 74 of the lock 70 from one side of the handle can cause gear engagement teeth/features 72 of the trigger lock 70 to engage/mesh and/or disengage/un-mesh with/from teeth of the pinion gear 67, which is mechanically coupled/meshed with the rack 62 of the trigger actuator 60. Therefore, when the locking teeth 72 are engaged/meshed with the teeth of the gear 67 (e.g., teeth of either cylinder/portion of the compound gear 67), the gear 67 may be unable to rotate, and therefore the teeth 72 may lock the trigger 60 from being pulled/actuated until disengagement of the trigger lock 70 through transverse movement/translation of the trigger lock 70 occurs. When laterally offset from the pinion teeth 68, the locking teeth 72 of the trigger lock 70 may be positioned such that the teeth 72 do not interfere with the gear, and thus the gear 67, and trigger 60, are unlocked and can move. Although FIG. 7-2B shows a transverse displacement of the trigger lock 70 to one direction to unlock the trigger 60, it should be understood that in some implementations, unlocking and/or locking of the trigger lock 70 may involve displacement from either side or in either transverse T direction, or in any other direction. In some implementations, it may be advisable to delay unlocking of the trigger 60 until the shaft 110 and end effector 114 have been advanced through the introducer/sheath (not shown) and into the internal anatomy (e.g., ventricle of the heart) to prevent inadvertent trigger pressing while advancing the delivery/deployment device 100.

The trigger lock may further include a position lock 173, also referred to herein as a state-locking feature, which may comprise one or more recesses, depressions, notches, teeth or the like, which may be laterally-arranged, as shown. The teeth/features of the position/state lock 173 may be configured to engage/mesh with one or more mating recesses, depressions, notches, teeth or the like 179 of the housing/handle, which may be laterally-arranged, as shown. The position lock may be oriented/aligned along or in parallel with a dimension $P_{tl}$ parallel to an axis $A_{tl}$ of the peg 74. The axis $A_{tl}$ of the peg 74 may be considered the axis of the trigger lock 70. Conversely, the locking teeth 72 of the lock 70 may be aligned with a circumferential dimension/line $C_{tl}$ that runs parallel with a circumference of the peg 74 and/or circumferentially about the axis $A_{tl}$ of the peg 74. In some examples, the teeth 72 are aligned/oriented along a tangent line/dimension $T_{tl}$ relative to the circumference/curve of the peg 74. Therefore, the locking teeth 72 and position lock 173 may be oriented in different dimensions/orientations, and may have orthogonal/perpendicular orientation with respect to at least portion(s) of the respective features.

Tension in the suture tail(s) 93 may be managed at least in part by displacement of the drive rod 85. That is, in implementations in which the internally-routed suture tail(s)

93 are engaged with the suture-coupling/routing feature 82 of the drive rod 85, linear translation of the drive rod may pull on the suture tail(s) 93 in a manner as to increase or decrease the tension/slack therein. In some implementations, the suture tail(s) 93 may pass through a lengthwise channel/slit 83 in the proximal portion of the drive rod 85, wherein being positioned/disposed within the channel/slit 83 retains the suture tail(s) 93 in a space relative to the end of the drive rod 85, wherein movement of the drive rod 85 causes movements in the suture tail(s) 93. The suture-coupling feature 82 of the drive rod 85 may comprise one or more transverse pins 182, which may be inserted through one or more transverse apertures 181 of the proximal portion of the drive rod 85. In some implementations, suture tails may be routed between a pair of parallel pins 182 in the drive rod 85. Alternatively, the proximal end of the channel 83 in which the suture tail(s) 93 are routed may be proximally open, wherein a single pin or other surface/structure in the drive rod channel 83 may be provided around which the suture tails may pass/route. Displacement of the drive rod 85 may be utilized to add slack in the suture tail(s) 93 for pushing the tissue anchor suture form off of the needle tip, and/or to subsequently remove slack in the suture tail(s) 93 to allow for tension to be pulled in the suture tails to form a suture knot tissue anchor.

As mentioned, the drive rod 85 may be coupled in some manner to the carrier 80, such that translation of the carrier 80 results in commensurate translation of the drive rod 85. For example, where direct coupling between the drive rod 85 and the carrier 80 is implemented, such as at a distal end of the drive rod 85 as shown in FIGS. 8A and 8B, actuation of the carrier 80 from action of the rack-and-pinion trigger actuator assembly may result in an identical translation/movement vector of the drive rod 85. In at least some configurations, the drive rod 85 may be slidingly-coupled to one or more instrument hubs. For example, the needle 30 may be coupled to and/or otherwise have associated therewith a needle hub structure 32. For example, the needle hub 32 may be physically coupled to the needle 30 and/or otherwise integrated or associated therewith at a proximal end of the needle 30, as shown. In such configuration, movement/translation of the needle hub 32 may result in corresponding movement/translation of the needle 30. Therefore, movement and/or deployment of the needle 30 may be controlled and/or facilitated by movement of the corresponding hub 32.

The plunger 40 may likewise be associated with a plunger hub structure 42, as shown. For example, the plunger hub 42 may be physically coupled to the plunger tube 40 at a proximal end thereof, or at any other portion of the plunger. The plunger hub 42 may be slidingly disposed about the drive rod 85, or otherwise coupled thereto.

The hubs 32, 42 may be slidingly coupled to the drive rod 85 in any suitable or desirable manner. For example, each of the hubs 32, 42 may comprise an aperture, channel, or other coupling feature 37, 47, wherein the drive rod 85 may be positioned within such channel/coupling feature. The hubs 32, 42 are referred to in some contexts herein as instrument "bases," and may be considered as such.

In some implementations, the plunger hub 42 may be positioned about the drive rod 85 at a position that is distal to the position of the needle hub 32. The respective lengths of the pusher 40 and the needle 30 may be selected to accommodate such relative offset positions of the plunger 42 and needle 32 hubs. For example, the needle 30 may advantageously be longer than the plunger tube 40 to allow for deployment/positioning of the tip of the needle 30 beyond the distal end of the plunger 40, which may be desirable for certain stage(s) of a tissue anchor deployment procedure, when the needle hub 32 is positioned proximal of the plunger hub 42.

The hubs 32, 42 may be configured to relatively freely slide along the length of the drive rod 85 unless and until the hubs are positioned relative to the drive rod 85 at certain respective locking positions associated with certain hub-locking features 81 of the drive rod 85. For example, the drive rod 85 may include certain divots or concavities 81, which may be configured to receive therein corresponding convex aspects/features of the hubs 32, 42. Although only one side of the drive rod 85 is shown, it should be understood that the hub-locking features 81 may be present on opposite sides of the rod 85. That is, each of the hub-locking features 81 shown may have a paired, identical or similar feature at the same axial/longitudinal position on the rod 85 on at an opposite circumferential position on the rod 85.

The hubs 32, 42 may each comprise one or more inwardly-projecting convexities/projections that may protrude into the drive rod channels thereof 37, 47, such that when the respective hub slides over a respective one of the hub-locking features 81 of the drive rod 85, the inwardly-projecting convexities/projections may become nested and/or otherwise disposed/secured within such locking feature 81 in a manner (e.g., interference fit) as to resist relative axial/longitudinal movement (with respect to the axis of the drive rod) of the hub relative to the drive rod 85 and/or locking feature 81. For example, each of the hubs 32, 42 may comprise a ball-/sphere-type feature 33, 43, which may be a separate/removable component from the hub 32, 42, or may be integrated therewith in some manner. Some threshold amount of force may be required to dislodge the convex features 33, 43 of the respective hub from respective ones of the hub-locking divots 81 to allow the respective hub to slide/move relative to the drive rod 85.

The hubs 32, 42 may further be slidingly coupled to the carrier 80 in some manner. For example, each of the hubs may include a tongue feature 36, 46, which may project downward from the hub into a lengthwise channel 89 of the carrier 80. Such coupling with the carrier may serve to retain the hubs 32, 42 in a desired orientation relative to the carrier 80 when translating along the drive rod 85. The hubs 32, 42 may further comprise certain other housing-engagement features 39, 49, which may serve to interact or interface with structural aspects of the handle housing 121 to further control the movement and/or positioning of the hubs. For example, such housing engagement features 39, 49 may comprise wings, tabs, or other projecting structural aspects configured to provide interference contact with the housing 121 in certain areas to constrain movement/positioning of the hubs.

The handle 120 may further comprise a drive rod restraining feature 137, in which the drive rod 85 may be able to slide/translate, but which may prevent tilting/off-axis contortion/movement of the drive rod 85, such that the drive rod moves/translates along a predefined axis/path. The housing 121 may further comprise one or more surfaces 131 configured to serve as hub-stopper surfaces to prevent sliding/translation of one or more of the hubs 32, 42 beyond a certain position/distance relative to the housing 121.

When a given hub 32, 42 is locked to the drive rod 85, movement of the carrier 80 may cause corresponding movement/translation of the locked hub, and therefore movement of a coupled/associated instrument (e.g., needle, pusher). Therefore, during certain stages of the tissue anchor deployment process during which one or both of the hubs is locked to the drive rod 85 at the respective hub-locking features/positions 81, trigger actuation, which causes movement of the carrier 80, may further cause movement/control of the associated instruments 30 and/or 40. When either of the hubs 32, 42 is detachably locked/coupled to the drive rod 85, such hub(s) is/are longitudinally fixed to the drive rod 85, such that they cannot slide along the rod 85, whereas in unlocked configurations, sliding along the drive rod 85 may be permitted if the hubs are otherwise held in place during drive rod 85 translation. The drive rod 85 may be a separate component from the carrier 80 that is fixedly coupled to the carrier 80, or the drive rod 85 may be an integrated/unitary form with the carrier 80. In either implementation, translation of the carrier 80 results in commensurate translation of the drive rod 85.

As described above, the hub-locking features 81 of the drive rod 85 and the bar-locking features 33, 43 of the needle 32 and plunger 42 hubs, respectively, collectively serve to lock/fix the relative position of the hubs 32, 42 relative to the drive rod 85. In some implementations, the device wo includes further features configured to lock/fix the positions of the hubs 32, 42 relative to the housing 121. That is, each of the hubs 32, 42 may at any given point be in one of three configurations: (i) a configuration in which the hub is locked to the drive rod 85; (ii) a configuration which the hub is locked to the housing 121 but free to slide relative to the drive rod 85; and/or (iii) a configuration in which the hub is free to slide relative to both the drive rod 85 and the housing 121.

In some implementations, the hub-locking features 126 of the housing 121 of the handle 120 may include certain divots/concavities, as shown, which, similar to the hub-locking features 81 of the drive rod 85, may be configured to receive convexities/projections associated with the respective hubs 32, 42. Such hub-locking features 126 may function as sphere-catches configured to allow for spherical, or semispherical, projections associated with the instrument hubs 32, 42, such as the illustrated spheres 33, 43, to sit in a concavity of the catch features.

The locking features 126 of the housing 121 may be configured to receive therein outwardly-projecting features of the hubs/assemblies 32, 42. In some implementations, the hub assemblies 32, 42 include ball/sphere features 33, 43 which project both inwardly for the purpose of providing a locking mechanism with the drive rod 85, as well as projecting outwardly from the hub body to provide a locking feature/mechanism for engaging with the hub-locking features 126 of the housing 121. When the hubs 32, 42 slide within the housing 121 and into position where the outwardly-projecting catch features 33, 43 (e.g., sphere/ball features) align longitudinally (with respect to the length/axis of the drive rod 85) with one of the hub-locking features 126 of the housing 121, the locking features 33, 43 of the hubs may become engaged with (e.g., nest within) respective ones of the hub-locking features 126 of the housing 121, thereby fixing the relative position of the hub to the housing. In some implementations, one or both of the hubs 32, 42 may be configurable to be locked to both the drive rod 85 and the housing 121 at the same time, though other examples permit only engagement with either a hub-locking feature 81 of the rod 85 or a hub-locking feature 126 of the housing 121 at a given time, but not both.

The description above describes the retention features 33, 43 of the respective hubs 32, 42 projecting outwardly from the hubs and engaging with respective hub-locking features 126 of the handle 120. Although FIG. 8B shows hub-locking features 126 associated with a first side ma (e.g., right side) of the handle housing 121, whereas the visible retention features 33, 43 in, e.g., FIG. 8A, are shown on a side of the hubs 32, 42 that faces away from the side ma of the housing 121, it should be understood that the handle 120, housing 121, and hubs 32, 42 may have certain symmetry. For example, the hubs 32, 42 may include additional retention features similar to the retention features 33, 43 (shown in FIG. 8B) on the non-visible side (e.g., left side) thereof configured to seat/engage with the visible/illustrated features 126*a*, 126*b* of the right side ma of the housing, respectively, and the interior aspect of the left side (not shown in FIG. 8B) of the handle housing 121 may have hub-locking features similar to the features 126 shown, wherein such features are configured to engage with the visible retention features 33, 43 of the hubs 32, 42 shown in FIG. 8A. It should be understood that any description herein of hub-locking features and/or retention features of instrument hubs may refer to either side of the hub, housing 121, drive rod 85, or other component of the handle 120, such as to one of symmetrically-paired features, although only illustrated and visible features of the various drawings may be described for clarity and descriptive purposes.

The tissue anchor sutureform 91, as described above, has one or more suture tails emanating proximally therefrom. At least a portion 93 of such suture tails may be routed internally within the housing 121, such as in a headspace area 128 of the housing 121, which may be above the finger-grip area 122. For example, in some implementations, the suture tail(s) 93 exit from out of the proximal end of the needle 30 and/or pusher 40 into the interior space 128 of the handle housing 121. As referenced above, the suture tail(s) 93 may further be routed through/around a suture-routing feature 82 of the drive rod 85, such as within a slit/channel 83 thereof and/or over/between one or more pin or other routing structural features of the drive rod 85. The slit/channel 83 may provide an aperture bounded on all sides to hold the suture portion routed therethrough in a confined space, wherein the suture(s) can axially slide through such channel/space.

Figure 9:
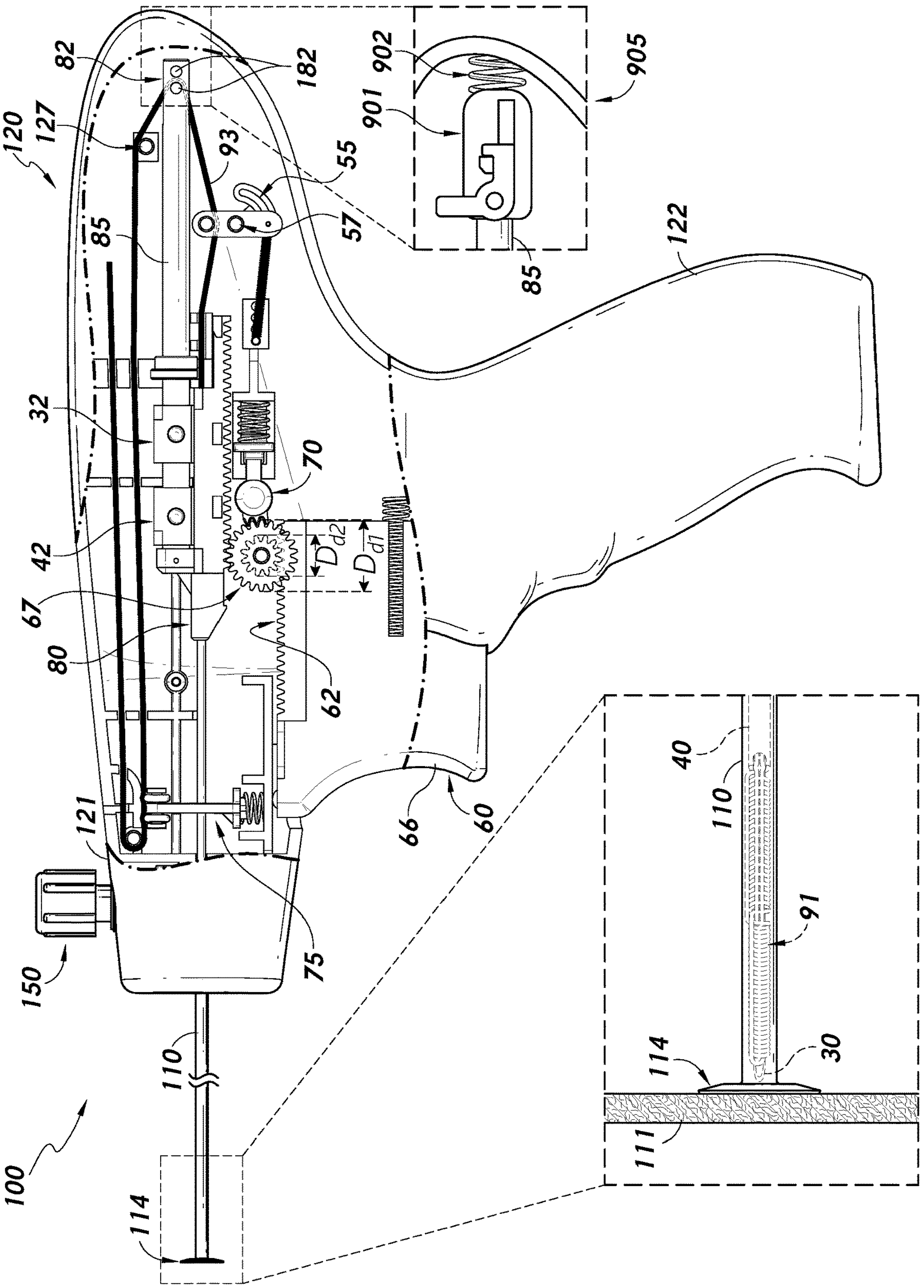
FIG. 9 shows a side cutaway view of a tissue anchor delivery device with a trigger actuator in a non-engaged configuration in accordance with one or more examples.

The routing between the needle/pusher and the drive rod suture-routing feature 82 may generally be in a proximal direction from the base of the needle or pusher, as shown, at least with respect to a non-engaged configuration of the device 100 as shown in FIG. 9 (described in detail below). The suture tail(s) 93 may further be routed from the suture-routing feature 82 of the drive rod 85 distally to the suture lock 75, at which point the suture tail(s) 93 may be secured to the housing 121, at least with respect to certain stages/periods of the tissue anchor deployment process. Additional proximal portions 99 of the suture(s) may extend from the suture lock 75 to free end(s) of the suture tail(s). Such portion 99 may be contained within the space 128 of the housing 121 and may be free and/or at least partially constrained therein.

In some implementations, the device 100 and/or housing 121 includes one or more additional routing components. For example, the housing 121 may include an upper proximal routing feature 127 over/through which the suture tail(s) 93 may be routed between the suture lock 75 and the suture-routing feature 82 of the drive rod 85. Such feature 127 may comprise a pin or other projection or surface over which the suture tail(s) 93 may be positioned/passed in a manner as to restrict transverse movement of the suture tail(s) 93 with respect to the length/axis of the suture(s) in some manner, such as by preventing the suture tail(s) 93 from deflecting/passing to the suture-routing feature 82 of the drive rod 85 within (e.g., below, and/or to the left of, with respect to the illustrated orientation of FIG. 8A) the housing routing feature 127, but rather requires that the suture tail(s) 93 pass over and/or outside of such feature.

The device 100 and/or housing 121 may further include a lower tensioner routing feature 55, which may be spring-biased, or biased in any other suitable or desirable manner (e.g., shape-memory) towards a certain position/configuration, wherein tension in the suture tail(s) 93 greater than a threshold amount may cause pivoting or other movement of the tensioner 55. The tensioner 55 may comprise one or more pins/bars through/over which the suture tail(s) 93 may be routed. In some examples, a pivot pin 57 is included, wherein the tensioner 55 is configured to rotate/pivot about the pin 57 in response to tension in the suture tail(s) 93. The tensioner 55 may serve to take-up slack in the suture tail(s) 93 in stages/periods in which slack is present in the lines 93. For example, when slack is present, the biasing of the tensioner 55 may cause a routing pin or feature against which the suture tail(s) 93 are disposed/routed to move in the direction of the biasing in a manner as to increase the routing path length of the suture tail(s) 93 between the carrier 80 and the drive rod routing feature 82 to thereby reduce the slack in the suture tail(s) 93. As tension increases in the suture tail(s) 93, the biasing may be overcome to reduce the routing path distance and produce a straighter path/configuration of the sutures between the carrier 80 and the routing feature 82 of the rod 85. Taking up the slack in the suture line(s) in certain stages may reduce the risk of entanglement or catching of the slack in the suture tails with other components of the device/handle.

FIG. 9 shows a side cutaway view of a tissue anchor delivery device 100 with a trigger actuator 60 in a non-engaged configuration in accordance with one or more examples. FIGS. 9-12 can be understood with reference to FIGS. 6-8, described in detail above. In an initial configuration, in which the trigger actuator 60 is not pulled/engaged, the needle hub 32 and the pusher hub 42 may be locked to the drive rod 85, wherein the drive rod 85 is positioned in a fully-proximal position, as shown. The suture tail(s) 93 run through the proximal suture-routing feature 82 of the drive rod 85, and therefore the suture tails are relatively tight due to the extension of the proximal portion of the drive rod 85 to the far proximal area of the handle 120. In the image of FIG. 9, the trigger 60 is locked by the trigger lock (e.g., locking pin) 70, the teeth 72 thereof being engaged with teeth of the pinion gear 67. As referenced above, the trigger lock 70 may be unlocked by laterally moving/displacing the trigger lock 70 from engagement with the trigger-meshed gear 67.

As shown in detailed image 905, alternative implementations of the device 100 may include a spring-assisted knot-formation feature 901, which may be positioned in a proximal portion of the head space 128 of the housing 121. The feature 901 may be configured to tension the suture tail(s) 93 with a spring-loaded form through which the suture tail(s) 93 may be routed. Following the necessary travel of the drive rod 85, the spring-loaded tensioner 901 may be released to remove slack in the suture(s) 93 and form the tissue anchor knot 90 by pulling proximally on the suture tail(s) 93. The spring 902 or other biasing member may couple the tensioner 901 to the housing 121.

Figure 10:
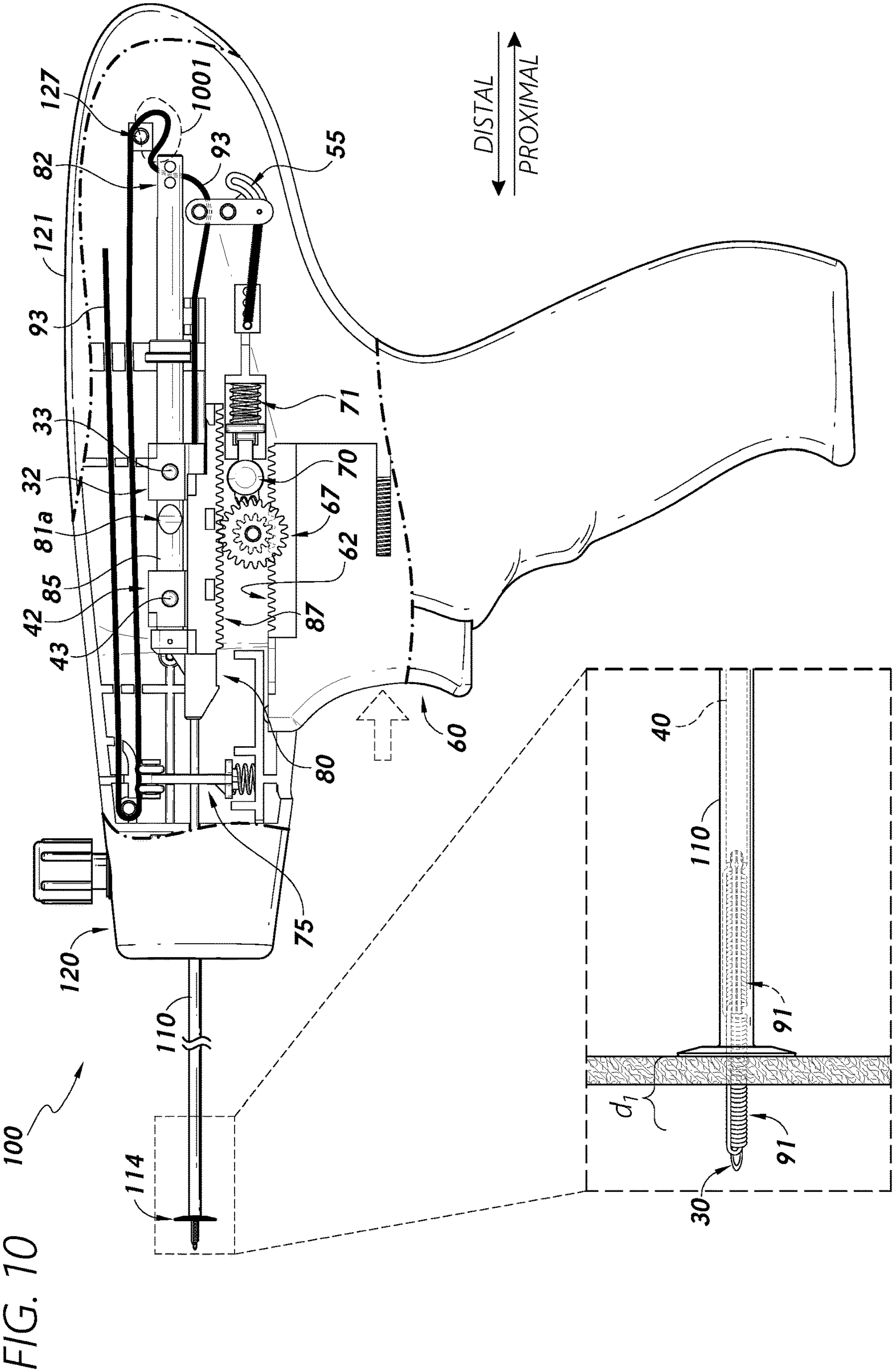
FIG. 10 shows a side cutaway view of a tissue anchor delivery device with a trigger actuator in a partially-engaged configuration in accordance with one or more examples.

FIG. 10 shows a side cutaway view of the tissue anchor delivery device 100 shown in FIG. 9 with the trigger actuator 60 thereof in a partially-engaged configuration in accordance with one or more examples. The system/device 100 is configured to implement displacement-based suture tension management, as described in detail herein. The image of FIG. 10 shows the internal routing of tissue anchor suture tail(s) 93 within the handle 120, wherein the suture tail(s) 93 are coupled, engaged, or otherwise routed through/over the suture-routing feature 82, which may comprise a proximal slit, channel, aperture, or the like, of the drive rod 85. In some examples, the suture-routing feature 82 comprises one or more pins, slits, or other features or surfaces through or over which the suture(s) 93 may be passed.

A pull of the trigger 60 in the proximal direction (or other direction depending on the particular implementation) serves to linearly translate the carrier 80 in a/distal direction. Such translation of movement between the trigger 60 and the carrier 80 may be facilitated by the pinion gear 67, which may be meshed with rack teeth of the trigger 60 and the carrier 80. Generally, actuation of the trigger 60 may cause linear translation of the carrier 80 in a direction/trajectory that is parallel to the motion of the trigger 60, but in an opposite direction relative to the trigger actuation. Movement of the carrier 80, due to a physical coupling thereof with the drive rod 85, may cause a corresponding movement/translation of the drive rod 85. Although referred to herein in certain context as a 'drive rod,' it should be understood that the component 85 may be referred to as a 'pull rod' in some contexts, which may be considered to be descriptive of the movement and/or action of such component in some instances.

FIG. 10 shows the trigger 60 in initial trigger actuation stage(s)/period(s), wherein the initial actuation stage(s) may correspond to any position of the trigger actuator 60 that is less than halfway between the non-engaged trigger position shown in FIG. 9 and the fully-engaged trigger position shown in FIG. 12 and described below. The initial trigger actuation, as shown in FIG. 10, may serve to create slack 1001 in one or more portions of the internally-routed suture tail(s) 93 due to the/distal translation of the drive rod 85, and therefore the suture-routing feature 82 thereof, which may draw a portion of the suture tail(s) 93 in the same direction due to a coupling or routing therewith/therethrough of the suture tail(s) 93. For example, as shown in FIG. 10, a portion 1001 of the suture tail(s) 93 in an area between a routing pin/structure 127 and the suture-routing/coupling feature 82 of the drive rod 85 may become slackened as the drive rod suture-coupling portion 82 is brought from a position proximal of the routing pin/structure 127 (see FIG. 9) to a position closer to the routing pin/structure 127 and/or distal of the routing pin/structure 127 (as shown in FIG. 10), thereby reducing the distance spanning between the routing pin/structure 127 and the distal portion 82 of the drive rod 85. Such slack 1001 may be necessary or desirable to allow for the sutureform tissue anchor 91 disposed in or near a distal portion of the delivery system shaft 110 to be deployed (e.g., pushed off of and/or out of the needle 30). That is, when the suture tail(s) 93 are locked within the housing 121 of the handle 120 by the suture lock 75, some amount of slack may be required in the suture tail(s) 93 between the suture lock 75 and the tissue anchor 91 along the path through which the suture tail(s) 93 are routed in order to allow for the tissue anchor 91 to be pushed off of the needle 30. However, prior to trigger actuation, it may be desirable for the suture tail(s) 93 to be tensioned, such that little or no slack is present in the suture tail(s) 93 between the suture lock 75 and the tissue anchor 90. Therefore, in the non-engaged configuration of FIG. 9, the position of the drive rod 85 may advantageously serve to hold the desired tension in the suture tails 90 in a manner as to reduce or eliminate slack therein, which may reduce the risk of knotting, tangling, or other undesirable state of the suture tail(s) 93. Subsequent trigger actuation as in FIG. 10 introduces the slack low needed for distal displacement of the suture anchor 91 (see Figure n). Therefore, along with other functions, actuation of the trigger 60 serves to transition the suture tail(s) 93 between tensioned and slackened configurations, as desirable or necessary for tissue anchor deployment.

As described above, the needle 30 may be disposed at least partially within a pusher tube 40. For example, the pusher tube 40 may comprise a lumen to allow for insertion therein of the needle 30, which may itself have a lengthwise central lumen in some implementations. The needle 30 is coupled at a base (e.g., proximal end) thereof to the needle hub 32, which may be configured to slide/move within the handle 120 as coupled to the drive rod 85 and/or carrier 80 in some manner (e.g., slidingly coupled). In addition to the needle hub 32, a pusher hub 42 may be coupled to the drive rod 85 and/or carrier 80 in some manner (e.g., slidingly coupled) and configured to slide within the housing 121/128, at least in certain configurations.

With further reference to FIG. 10, as the trigger 60 is pulled, the carrier 80 and drive rod 85 are advanced forward, which in turn advances the needle 32 and pusher 42 hubs forward along with the drive rod 85, as the hubs 32, 42 may initially be locked to the drive rod 85. Such forward movement/driving of the pusher 42 and needle 32 hubs causes the needle 30 and pusher 40 to be advanced within the shaft 110, thereby causing the distal tip of the needle 30 to be deployed/projected from the distal end of the shaft 110. That is, the initial pulling of the trigger 60 may cause the needle 30 to puncture the target tissue in (e.g., heart valve leaflet) by deploying the needle to 30 from the elongate shaft 110. Such actuation may not cause the pusher tube 40 to deploy from the shaft distal end in some implementations due to the relative positioning of the pusher distal end and needle distal end/tip and/or the relative positioning of the respective hubs associated therewith.

The actuation of the trigger 60 in connection with FIG. 10 may cause advancements of the needle 32 and pusher 42 hubs until the needle hub 32 reaches longitudinal alignment with the hub-locking feature 126*a* (see FIG. 8B) of the housing 121, which may lock/secure the hub 32 to the housing 121 with sufficient retention force to overcome the force required to displace the drive rod 85 and hub-locking feature 81*a* thereof from the inwardly-projecting retention feature 33 of the needle hub 32. That is, the retention of the retention feature 33 outwardly projecting/nesting into the locking feature 126*a* of the housing 121 may be sufficient to cause further/distal advancement of the carrier 80 and drive rod 85 to push the hub-locking feature 81*a* of the drive rod 85 past the retention feature 33 of the hub 32, thereby allowing the hub 32 to detach from the fixed longitudinal coupling with the drive rod 85 and slide relative to the drive rod 85. Such locking of the position of the needle hub 32 relative to the housing 121 may serve to limit the deployment/projection distance $d_1$ of the needle past the distal end of the shaft 110. Limiting the distance $d_1$ of the needle projection can be desirable to prevent or reduce the risk of injury to the patient from needle exposure within the patient anatomy (e.g., left atrium). In some implementations, the user may feel tactile/haptic feedback associated with the locking of the needle hub 32 to the housing 121. For example, the seating/nesting of the retention feature 33 in the locking feature 126*a* may involve contacting of the retention feature 33 with the locking feature 126*a* in a manner providing physical and/or audible indication that is perceptible to the user.

When one of the hubs 32, 42 is locked to the drive rod 85 by one of the hub-locking features 81, the hub may be considered to be in a fixed coupling with the drive rod 85. Alternatively, when the hub has been pushed out of fixed coupling/engagement with the drive rod feature(s) 81, such hub may be considered to be in a sliding coupling with the drive rod, wherein the hub can slide longitudinally along the drive rod 85, but may still be coupled/constrained to the drive rod in some manner, such as through the passing of the drive rod 85 through a channel or aperture 37, 47 of the hub.

As the drive rod 85 is advanced in a manner as to decouple from the hub 32, the diameter of the drive rod 85 longitudinally outside of the hub-locking cutout/concavity 81*a* may press against and/or contact the internally-projecting aspect of the retention feature 33, thereby pushing/holding the hub 32 into engagement with the hub-locking feature 126*b* of the handle 120. Once the needle hub 32 has become secured/locked to the housing 121, further pulling/actuation of the trigger 60 can cause further distal/forward advancement of the carrier 80 and still-coupled pusher hub 42, whereas, the needle hub 32 may remain locked in the position illustrated in FIG. 10 during such advancement. That is, with the needle hub 32 (and needle 30) decoupled from the drive rod 85, the pusher hub 42 (and pusher 40) can continue to advance along with the carrier 80, independent of the needle 30.

Figure 11:
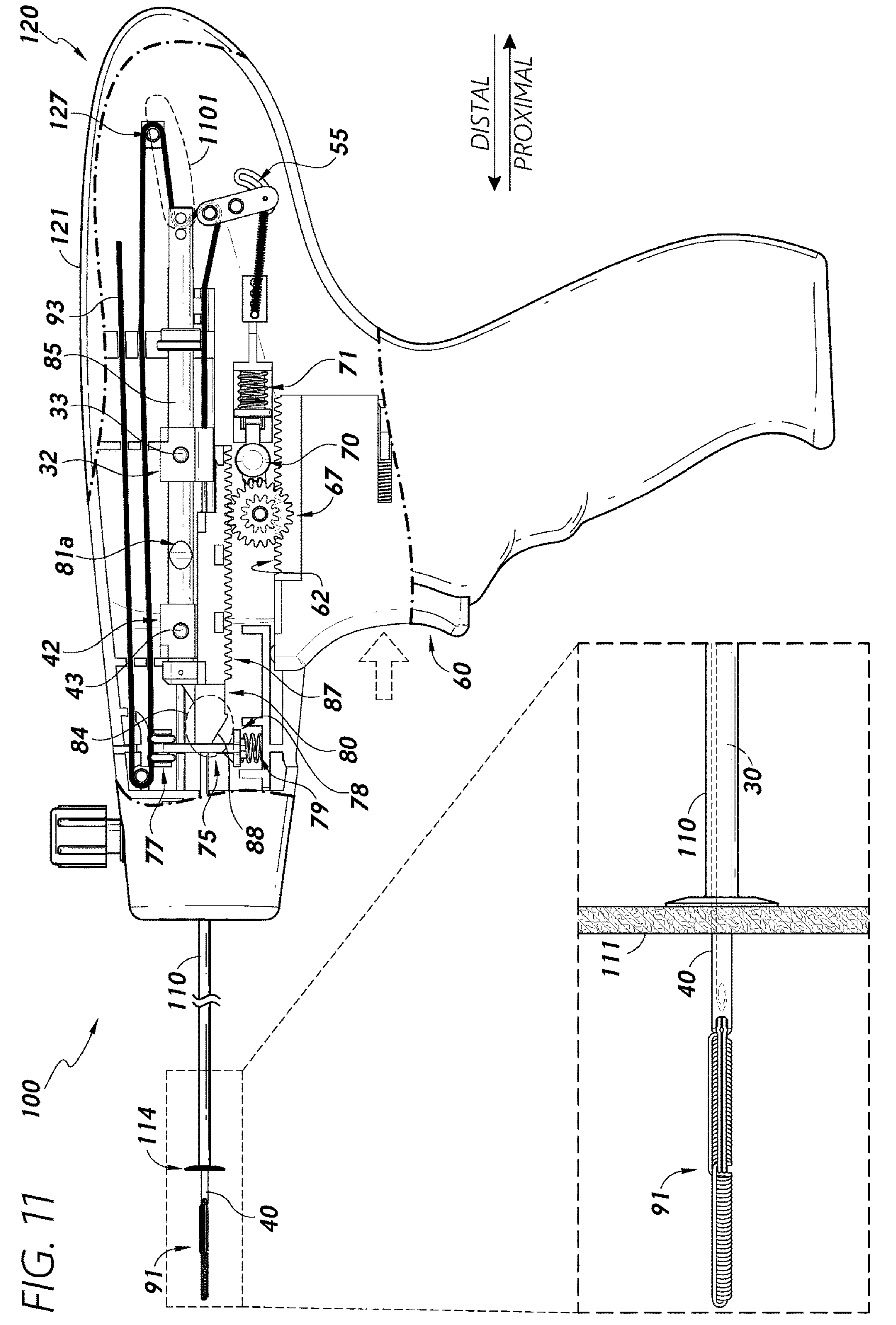
FIG. 11 shows a side cutaway view of a tissue anchor delivery device with a trigger actuator in a partially-engaged configuration in accordance with one or more examples.

FIG. 11 shows a side cutaway view of the tissue anchor delivery device 100 with the trigger actuator 60 in a partially-engaged (e.g., mostly-engaged) configuration in accordance with one or more examples. The configuration of the device 100 shown in FIG. 11 corresponds to a mostly-engaged position of the trigger actuator 60, and corresponding internal mechanical components. For example, "mostly-engaged," as used herein in reference to tissue anchor deployment devices with trigger actuators, may refer to a position of the trigger 60 that is more than halfway between the non-engaged trigger position shown in FIG. 9 and the fully-engaged trigger position shown in FIG. 12. In such position(s), the needle hub 32 may be decoupled from the drive rod 85, whereas the pusher hub 42 may, at least initially, be coupled to the drive rod 85 and therefore continuing to move with the carrier 80 as pulled by the drive rod 85.

Whereas the stage(s) associated with the configuration of FIG. 10 involve introducing slack 1001 into the suture tail(s) 93, subsequent stage(s), as shown in FIG. 11, may involve at least partially removing the slack 1001 from the suture tail(s) 93 within the housing 121. As the trigger 60 is further pulled (e.g., to the right with respect to the illustrated orientation), the carrier 80 is driven further forward/distally, which pulls the drive rod 85 further forward, thereby increasing the routing path of the suture tail(s) 93 and taking out the slack 1001 and tensioning the suture tail(s) 93. For example, the suture-routing feature 82 of the drive rod 85 may pull the suture tail(s) in the area 1101 to the left of the tensioner routing feature 55 to cause the suture tails to double-back in the distal direction, as shown in FIG. 11, thereby creating a more tortuous/long suture path and taking up the slack in the suture tail(s) 93. Because the suture lock 75 fixes the suture tail(s) 93 to the housing 121, increased routing distance between the suture locks 75 and the suture anchor 91 reduces the slack and increases the tension in the suture tail(s) 93 within the housing 121.

As the pusher hub 42 continues to translate distally, whereas the needle hub 32 remains locked/secured to the housing 121, the distance between the pusher hub 42 and the needle hub 32 is increased relative to the stage(s) associated with FIG. 10. Therefore, the relative position of the distal end of the pusher 40 relative to the tip of the needle 30 also changes in a manner such that the pusher tip moves farther distally (e.g., to the left with respect to the illustrated orientation) relative to the needle tip 30. This movement of the pusher 40 relative to the needle 30 can allow for the pusher to push the sutureform 91 off of the needle 30 to thereby allow for deployment of the sutureform 91 to form a bulky knot tissue anchor 90.

When the pusher hub 42 reaches the position shown in FIG. 11, the retention feature 43 thereof may become seated/engaged in the concavity feature 126*b* of the handle 120 (see FIG. 8A), such that the drive rod 85 can be advanced past the coupled engagement with the hub 42 and the hub 42 becomes disengaged from the longitudinally-fixed coupling with the drive rod 85. As the drive rod 85 is advanced in a manner as to decouple from the hub 42, the diameter of the drive rod 85 longitudinally outside of the hub-locking cutout/concavity 81*b* (visible in FIG. 12) may press against and/or contact the internally-projecting aspect of the retention feature 43, thereby pushing/holding the hub 42 into engagement with the hub-locking feature 126*b* of the handle 120. The pusher hub 42 advances with the pulling of the trigger 60 until it reaches the locked position shown in FIG. 11, which represents the projection limit of the pusher 40, shown on the left side of the diagram as extending to and/or past the tip of the needle 30. In such position, the pusher 40 advantageously pushes all of the windings of the knot sutureform 91 off of the needle 30. As described above, in such state(s) of the procedure, the needle 30 may be stationary due to the locking of the needle hub 32 to the housing 121 and the decoupling from the drive rod 85, and therefore the further advancement of the pusher 40 is relative to a stationary needle, thereby allowing for the pusher to push the knot sutureform 91 off of the needle 30.

Figure 12:
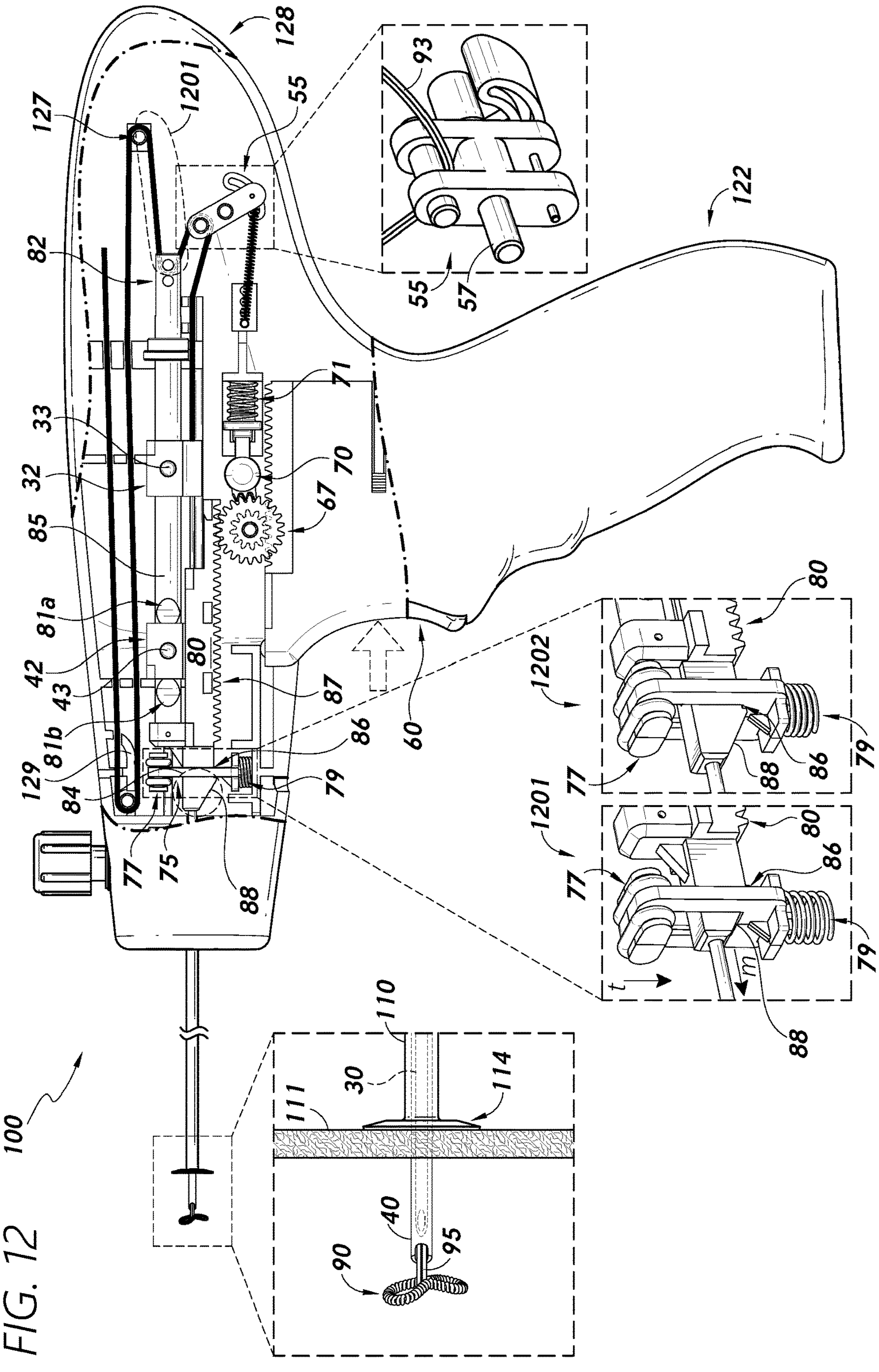
FIG. 12 shows a side cutaway view of a tissue anchor delivery device with a trigger actuator in a fully-engaged configuration in accordance with one or more examples.

FIG. 12 shows a side cutaway view of the tissue anchor delivery device 100 with the trigger actuator 60 in a fully-engaged configuration in accordance with one or more examples. Once the knot windings 91 have been pushed off of the needle 30, the system/device may be in condition to initiate tensioning of the suture tail(s) 93 to form the windings 91 into a formed suture tissue anchor 90, such as a bulky-not type suture anchor (e.g., figure-eight form). The trigger 60, therefore, may be utilized to deploy the suture windings 91 of the tissue anchor from the needle 30 and to transition the longitudinally-arranged sutureform 91 to the retention form 90 to serve as a tissue anchor.

The tightening of the suture tail(s) 93 to form the bulky knot tissue anchor 90 can be achieved by the further advancement of the drive/pull rod 85. For example, once the pusher hub 42 has become locked/fixed in the longitudinal dimension to the housing 121, the carrier 80 and coupled drive rod 85 can continue to move forward in correspondence with further pulling of the trigger 60 in the proximal direction, independent of the pusher 40 and needle 30. The drive rod 85, as described above, has the suture tail(s) 93 routed through/over the suture-routing feature 82 thereof, which may include one or more gaps, slits, pins, ridges, or other routing structure/means. Therefore, the further advancement of the carrier 80 and drive rod 85 further tensions the suture tail(s) 93. For example, the suture-routing feature 82 of the drive rod 85 may be configured to restrain the suture tails on all sides, wherein the suture tail(s) 93 run through a gap/path in the feature 82, such as between two pins or structures within a slit or channel 83 associated with a proximal portion of the rod 85. In some implementations, the suture-routing feature 82 comprises one or more apertures or other channels through which the suture tails are routed in a manner as to restrain them on distal and proximal sides with respect to the illustrated orientation of the device 100. The suture retention on the proximal side/end of the feature 82 and/or bar 85 can allow for advancement of the bar 85 in the/distal direction to pull the suture tail(s) 93 in the forward/distal direction between the routing features 127 and 55, thereby further increasing the length of the routing path between the features 127, 55, which results in increased tension in the suture tail(s) 93 in such area/portion. The suture-routing feature 82 advantageously provides retention from both the proximal and distal sides with respect to the illustrated orientation, which allows for pulling on the suture(s) 93 in both directions of translation of the drive rod 85. The increase in tension in the suture tail(s) 93 caused by the forward translation of the drive rod 85 after decoupling of the pusher hub 42 from the drive rod 85 causes the deployed sutureform 91 to be bunched/pulled together to form a bulky-knot-type tissue anchor 90, as shown.

As referenced above, examples of the present disclosure provide solutions for automatically unlocking and/or locking suture tails in a tissue anchor delivery system. Once the tissue anchor 90 has been deployed and formed into the knot-type tissue anchor, it may be desirable to withdraw the device/system 100 the from the anatomy and/or from off of the suture tail(s) 93 to allow for permanent implantation of the tissue anchor 90 and length of suture tail(s) in the anatomy. As described in detail above, the system/device 100 may comprise a suture lock 75, which may be engaged to lock the suture(s) 93 to the internal structure of the housing 121. However, such locking of the suture(s) 93 to the housing 121 can prevent the decoupling and withdrawal of the device/system 100 from off of the suture tail(s) 93. Therefore, it may be desirable to implement a mechanism for unlocking the suture tail(s) 93 from the housing 121 and/or components therein. Examples of the present disclosure advantageously provide for the automatic unlocking of suture tails lock/fixed in a handle/housing of a tissue anchor deployment device/system. For example, such unlocking may occur in response to the pulling of a trigger actuator to a certain position/configuration, such as a position/configuration at or near a fully-deployed position of the trigger.

As shown in the detailed images of FIG. 12, the carrier 80 may be configured to displace the suture lock 75, such as by effecting transverse displacement of a spring-loaded rocker/tensioner aspect 79 of the suture lock 75 to thereby move/displace the suture lock 75 in the transverse direction t, thereby removing the head portion 77 of the suture lock 75 from pressure contact with the surface 129 of the housing 121. With the head portion 77 withdrawn from the suture-sandwiching configuration between the head 77 and the surface 129, the suture tail(s) 93 may be free to be drawn past the suture lock 75 and head portion 77 thereof. Therefore, in some examples, the carrier 80 may be configured to unlock the suture lock 75 by applying pressure/force in a transverse direction t away from the suture tail(s) 93 to thereby displace the suture lock 75 and free-up the suture tails. When the suture lock 75 is unlocked by the carrier 80, the suture tail(s) may be withdrawn from the handle housing 121 through the tortuous routing of the suture tail(s) 93 within the housing 121 and through the lumen of the needle 30, pusher 40, and/or elongate shaft 110.

The unlocking of the suture lock 75 may be implemented by further advancing the carrier 80 after the pusher hub 42 (and needle hub 32) has been detached/decoupled from the drive rod 85, such that the drive rod 85 advances in the/distal direction substantially free of the hubs 32, 42; although the hubs 32, 42 are no longer fixed longitudinally to the drive rod 85 via the hub-locking features 81, and therefore the hubs can be considered 'decoupled' from the drive rod, the hubs 32, 42 may still be slidingly coupled to the drive rod 85 in a manner such that the hubs can slide longitudinally along at least a portion of the length of the drive rod 85 while being laterally restrained (e.g., in the transverse/radial dimension with respect to the length of the rod 85) by the rod 85 through some slidable coupling therewith (e.g., the rod 85 may pass through a channel/aperture 37, 47 in the hub(s)). After the needle 32 and pusher 42 hubs have decoupled from the drive rod 85, the further distal/forward advancement of the drive rod 85 and carrier 80 may serve one or more additional purposes/functionalities. For example, the further advancement of the drive rod independently of the instrument hubs 32, 42 may serve to further tighten/tension the suture tail(s) 93 by pulling the suture tail(s) 93 in the distal/forward direction between the routing features 127, 55, as shown. In addition, further advancement of the carrier 80 may serve to unlock the suture tail(s) 93 from the suture lock 75.

The unlocking of the suture(s) 93 may be achieved at least partially automatically in connection with the further pulling of the trigger 60. For example, the carrier 80 may include a distal nose/sled 84 including a ramp/inclined-surface 88 that may operate as a cam surface for gradually displacing the base 78 of the suture lock 75 in the transverse direction t. The further advancement of the carrier 80 by pulling the trigger 60 and actuating the rack-and-pinion system/assembly of the device 100 causes the cam/ramp surface 88, which may be associated with a distal-most nose/portion 84 of the carrier 80, to push against the base 78 of the suture lock 75 to a gradually-increasing degree, as shown in detailed image 1201, thereby overcoming the spring bias in the transverse dimension t towards the housing surface 129 to allow the suture lock 75 to move in the transverse dimension t away from the contact surface 129, thereby unlocking the suture tail(s) 93 from the handle/housing 121. That is, full actuation of the trigger 60 deploys and forms the knot and automatically unlocks/unfixes the suture tail(s) 93 from the delivery system/housing 121. The ramp 88 may be inclined/angled with respect to a direction of movement m of the carrier 80, as well as with respect to the transverse direction t of deflection/translation of the suture lock 75, as shown.

In some implementations, the handle 120 provides a mechanism for locking the suture lock 75 in the unlocked configuration shown in FIG. 12, which may be desirable to prevent re-locking of the suture tail(s) 93 after full deployment and formation of the tissue anchor 90 and full engagement of the trigger actuator 60. For example, the carrier 80 may include a notch/lip feature 86, such as on an underside thereof, which may have ridges/lips on one or more sides thereof designed to prevent the carrier 80 from moving/reversing past the base 78 of the suture lock 75 once the base 78 has seated past/within the notch retention feature 86. Such seating of the base 78 in the retention feature 86 may occur once the ramp/cam surface 88 has traversed the base 78 and assumed a position distal to the base 78, as shown in the detail 1202. The state of the suture lock 75 and the carrier 80 may be considered 'unlocked' states, or 'suture-unlocked' states. As the nose 84 of the carrier 80 advances through the aperture 176, transverse t displacement of the base 78 is achieved in a graduated/increasing manner (e.g., to a linearly or non-linearly increasing degree), thereby moving the head 77 away from press-holding the suture(s) 93.

With the base 78 positioned in/past the notch 86, the suture lock 75 is locked in the unlocked configuration, and further the carrier 80 is locked in its present position, the carrier being unable to be retracted/reverse due to the presence of the base 78 of the suture lock 75 protruding into/against the notch retention feature 86, which is pressed/held into the notch 86 by the spring 79. With the carrier 80 locked in place, the trigger 60 may also be locked in the fully engaged/depressed configuration due to the mechanical coupling between the trigger 60 and the carrier 80 via the trigger rack 62, pinion gear 67, and carrier rack 87, as described in detail above.

When the suture lock 75 is in the locked configuration, The spring 79 on the lower side of the suture lock 75 may maintain a constant contact/pressure against the suture tail(s) 93 and contact surface 129 until the carrier 80 moves forward and overcomes the force of the spring 79 to displace the suture lock 75 and unlock the suture tail(s) 93. Once the base 78 of the suture lock 75 seats in/against the undercut/notch 86 at the end of the ramp/cam surface 88 of the carrier 80, the spring 79 may serve to maintain constant pressure to hold the base 78 in the locking feature 86. When the suture lock 75 and base 78 thereof ride down on the ramp/cam surface 88 until the base 78 passes/pops-over the proximal end/lip of the ramp/nose 84 and locks in place in/against the carrier lock/notch 86, the sliding of the base 78 into the notch feature 86 may serve as an indication to the surgeon/user that the suture tail(s) 93 is/are unlocked and it is therefore safe to remove the device 100 from off of the suture tail(s). For example, the spring 79 may produce a movement in the base 78 into the notch 86, such movement having sufficient velocity to cause an audible signal from the contact of the base 78 with the surface of the carrier 80 adjacent the notch/lip 86, which may be perceptible to the user. Furthermore, such contact may provide a tactile/haptic signal manually perceptible in the handle that communicates to the user the successful unlocking of the suture lock 75. For example the seating of the base 78 in/against the notch 86 can create a detent in the user's finger(s) holding the handle and/or trigger 60, such that the user can feel an end-of-travel of the carrier 80, hear a click or other audible signal, and/or feel the click of the suture lock 75 sliding into place and locking the trigger 60.

Figure 13:
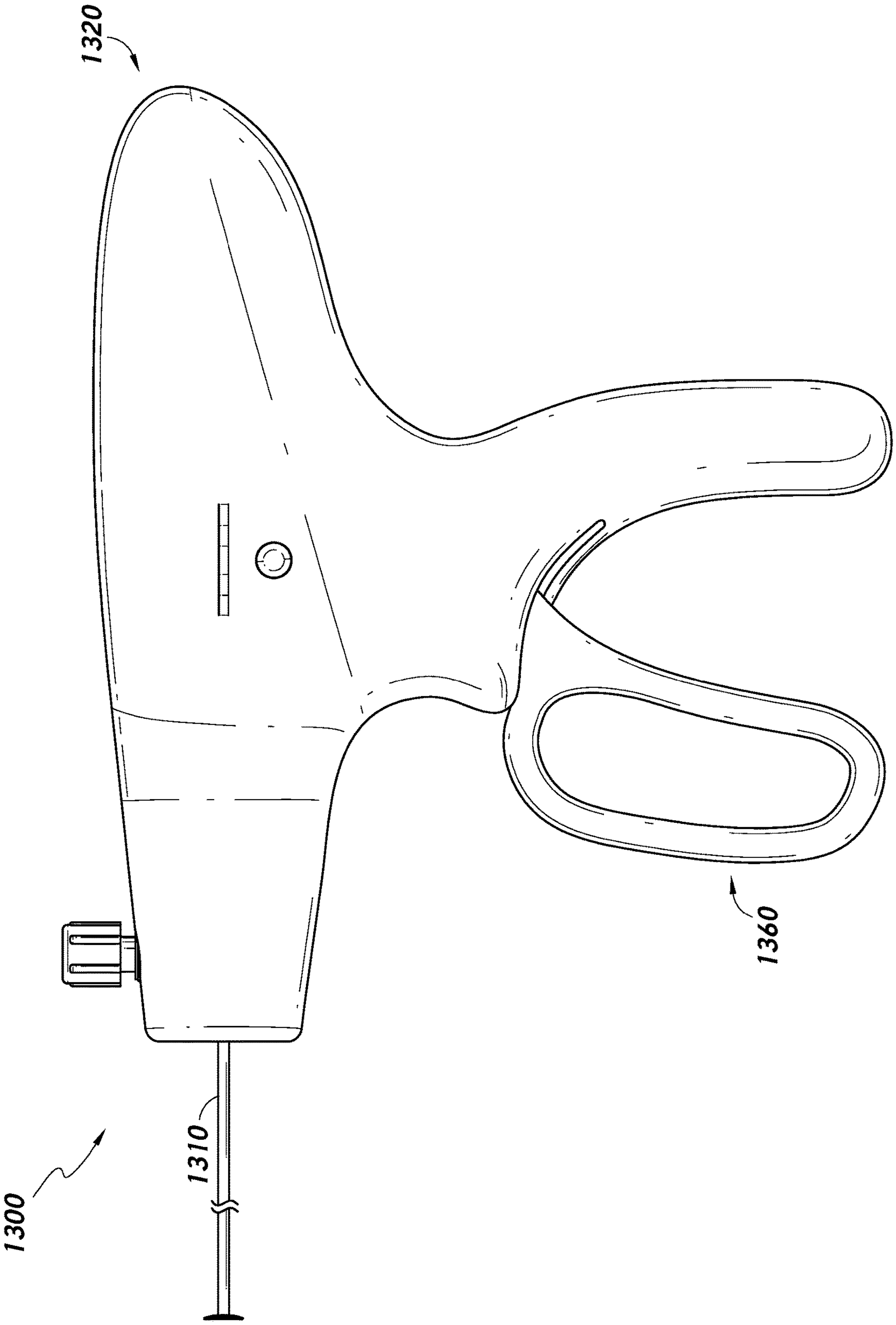
FIG. 13 shows a side view of a trigger-based tissue anchor delivery device in accordance with one or more examples.

FIG. 13 shows a side view of a trigger-based tissue anchor delivery device 1300 in accordance with one or more examples. The device 1300 may include a handle 1320 and elongate shaft 1310, as with other examples of the present disclosure.

The device 1300 may include a lever-type trigger actuator 1360 configured to cause actuation and/or translation of one or more internal components of the device 1300 to implement needle puncture, tissue anchor deployment (e.g., sutureform deployment), and/or tissue anchor formation (e.g., bulky knot tissue anchor formation through suture tail tensioning. That is, the trigger 1360 may be configured to cause actuation of any of the components described above in connection with linearly-translating triggers associated with other examples. For example, the trigger 1360 may be mechanically coupled with a rack-and-pinion mechanism configured to produce linear translation of a carrier, drive rod, pusher hub, and/or needle hub. The trigger 1360 may be configured to rotate about a fulcrum/hinge, which may provide leverage to amplify input pulling force of the user to provide desirable ease-of-use. It should be understood that any of the examples disclosed herein may include linearly-translating or lever-type trigger actuators, regardless of the particular trigger example illustrated or described.

ADDITIONAL EXAMPLES

Provided below is a list of examples, each of which may include aspects of any of the other examples disclosed herein. Furthermore, aspects of any example described above may be implemented in any of the numbered examples provided below.

Example 1: A medical instrument comprising a handle, a suture lock associated with the handle, the suture lock being configured to fix a position of a portion of a suture line relative to a portion of the handle when the suture lock is in a locked position, and a manually-actuatable actuator associated with the handle and configured to cause the suture lock to transition from the locked position to an unlocked position.

Example 2: The medical instrument of any example herein, in particular example 1, further comprising a carrier structure configured to move within the handle, wherein said causing, by the actuator, the suture lock to transition from the locked position to the unlocked position is caused at least in part by said movement of the carrier structure within the handle.

Example 3: The medical instrument of any example herein, in particular example 2, wherein the carrier structure is configured to displace the suture lock to cause the transition to the unlocked configuration.

Example 4: The medical instrument of any example herein, in particular example 2, wherein the suture lock comprises a base portion, and a head portion configured to press against the portion of the suture line to fix the position of the portion of the suture line.

Example 5: The medical instrument of any example herein, in particular example 4, wherein the carrier structure comprises a nose portion configured to displace the base portion of the suture lock to thereby move the head portion of the suture lock away from the portion of the suture line.

Example 6: The medical instrument of any example herein, in particular example 5, wherein the nose portion of the carrier structure includes a ramp configured to displace the base of the suture lock in an increasing degree as the carrier structure moves towards the suture lock.

Example 7: The medical instrument of any example herein, in particular example 6, wherein the carrier structure includes a notch that is proximal of the ramp, wherein the notch is configured to have disposed therein the base portion of the suture lock.

Example 8: The medical instrument of any example herein, in particular example 7, wherein when the base portion of the suture lock is disposed in the notch of the carrier structure, the carrier structure is locked in position.

Example 9: The medical instrument of any example herein, in particular example 7, further comprising a spring configured to bias the suture lock in the locked configuration, wherein when the nose portion of the carrier structure is in contact with the base portion of the suture lock, movement of the carrier structure towards the suture lock overcomes a biasing force of the suture lock, and when the base portion of the suture lock is disposed in the notch of the carrier structure, the spring biases the base portion of the suture lock in the notch of the carrier structure.

Example 10: The medical instrument of any example herein, in particular any of examples 2-9, further comprising a drive rod coupled to the carrier structure, the drive rod including a suture-routing channel configured to have the suture line routed therethrough such that translation of the drive rod changes a tension of the suture line when the suture lock is in the locked configuration.

Example 11: The medical instrument of any example herein, in particular any of examples 2-10, wherein movement of the carrier structure causes movement of at least one of a needle instrument or a pusher instrument associated with the handle.

Example 12: The medical instrument of any example herein, in particular example 11, wherein the suture line emanates from within at least one of the needle instrument or the pusher instrument.

Example 13: The medical instrument of any example herein, in particular example 11, wherein each of the needle instrument and the pusher instrument has a respective proximal hub that is coupled to a drive rod that is coupled to the carrier structure.

Example 14: A method of tensioning a suture, the method comprising providing an instrument comprising a handle having a suture line disposed therein, a portion of the suture line being fixed to a portion of the handle by a suture lock configured in a locked configuration, and actuating a trigger actuator of the handle to cause linear translation of a carrier within the handle until a nose portion of the carrier contacts and displaces the suture lock, thereby transitioning the suture lock from the locked configuration to an unlocked configuration.

Example 15: The method of any example herein, in particular example 14, wherein prior to the nose portion contacting the suture lock, said actuating the trigger causes a first change in tension in the suture line that decreases a tension of the suture line.

Example 16: The method of any example herein, in particular example 15, wherein, subsequent to the first change in tension and prior to the nose portion contacting the suture lock, said actuating the trigger causes a second change in tension in the suture line that increases the tension of the suture line.

Example 17: The method of any example herein, in particular any of examples 14-16, wherein the carrier is coupled to a drive rod including a suture-routing channel through which the suture line is routed, and said linear translation of the carrier causes a change in tension in the suture line by changing a position of the suture-routing channel of the drive rod.

Example 18: The method of any example herein, in particular example 17, wherein the suture-routing channel comprises a longitudinal, proximally-open slit in the drive rod.

Example 19: The method of any example herein, in particular example 18, wherein one or more transverse pins are disposed in the slit to form, at least in part, the suture-routing channel.

Example 20: The method of any example herein, in particular any of examples 14-19, wherein the nose portion of the carrier comprises an inclined surface configured to displace the suture lock in a transverse direction with respect to a direction of movement of the carrier.

Example 21: The method of any example herein, in particular any of examples 14-20, wherein the suture lock comprises a base portion, a head portion having a suture-contact surface, and a body portion coupling the base portion and the head portion.

Example 22: The method of any example herein, in particular example 21, wherein said displacing the suture lock involves advancing the nose portion of the carrier at least partially through an aperture in the body portion of the suture lock.

Example 23: The method of any example herein, in particular example 21, wherein when the suture lock is in the locked configuration, the portion of the suture line is held between the head portion of the suture lock and an opposing contact surface of the handle, and said displacing the suture lock involves moving the head portion of the suture lock away from the opposing contact surface.

Example 24: The method of any example herein, in particular example 21, further comprising locking the trigger actuator at least in part by actuating the trigger actuator to advance the nose portion of the carrier until the base portion of the suture lock engages with a catch of the carrier.

Example 25: The method of any example herein, in particular example 24, wherein the catch of the carrier is positioned proximally adjacent to an inclined surface of the nose portion of the carrier.

Example 26: The method of any example herein, in particular example 24, wherein the catch of the carrier comprises a lip configured to provide interference with the base portion of the suture lock on a distal side thereof when the lip has advanced past the base portion of the suture lock.

Example 27: The method of any example herein, in particular example 24, wherein said displacing the suture lock involves overcoming a spring-biasing of the suture lock that biases the suture lock in the locked configuration.

Example 28: An actuator assembly comprising a manually-pressable trigger actuator including a first rack, a carrier comprising a second rack, a pinion gear configured to be meshed with the first rack and the second rack, a drive rod coupled to the carrier, and a first instrument hub detachably coupled to the drive rod, the first instrument hub being associated with a first instrument.

Example 29: The actuator assembly of any example herein, in particular example 28, wherein the first instrument hub is an elongate needle coupled at a proximal end thereof to the first instrument hub.

Example 30: The actuator assembly of any example herein, in particular example 28, wherein the first instrument hub is detachably coupled to the drive rod via a projection structure configured to nest within a divot formed in the drive rod.

Example 31: The actuator assembly of any example herein, in particular example 28, wherein the first instrument hub is detachably coupled to the drive rod via a concave catch configured to have a projection structure of the drive rod seated therein.

Example 32: The actuator assembly of any example herein, in particular any of examples 28-31, further comprising a second instrument hub detachably coupled to the drive rod, the second instrument hub being associated with a second instrument.

Example 33: The actuator assembly of any example herein, in particular example 32, wherein the drive rod passes through apertures in the first and second instrument hubs.

Example 34: The actuator assembly of any example herein, in particular example 32 or example 33, wherein the first instrument hub comprises an elongate needle, and the second instrument hub comprises an elongate pusher tube, the needle being disposed at least partially within the pusher tube.

Example 35: The actuator assembly of any example herein, in particular example 34, wherein the first instrument hub is coupled to the drive rod proximal of the second instrument hub.

Example 36: The actuator assembly of any example herein, in particular any of examples 28-35, wherein the first instrument hub comprises a tongue projection that is configured to slide within a longitudinal channel of the carrier.

Example 37: The actuator assembly of any example herein, in particular any of examples 28-36, wherein the first instrument hub comprises a projection configured to seat in a concave catch of a housing in which the actuator assembly is at least partially disposed.

Example 38: The actuator assembly of any example herein, in particular example 37, wherein, when the projection of the first instrument hub is seated in the concave catch of the housing and the first instrument hub is coupled to the drive rod, further advancement of the carrier caused by actuation of the trigger actuator causes the first instrument hub to detach from longitudinal fixation with the drive rod.

Example 39: The actuator assembly of any examples 28-38, further comprising a trigger lock configured to selectively engage and disengage with the pinion gear through lateral displacement of the trigger lock.

Example 40: The actuator assembly of any example herein, in particular example 39, wherein the trigger lock is manually depressible to cause said lateral displacement.

Example 41: The actuator assembly of any example herein, in particular any of examples 28-40, wherein the trigger actuator is a linearly-translating actuator.

Example 42: The actuator assembly of any example herein, in particular any of examples 28-40, wherein the trigger actuator is a lever actuator configured to rotate about a fulcrum.

Example 43: A medical device comprising a handle, an elongate shaft, a needle assembly including an elongate needle disposed at least partially within the elongate shaft and a needle hub disposed at least partially within the handle, and a trigger associated with the handle, the trigger being configured such that actuation of the trigger causes linear translation of the needle within the elongate shaft.

Example 44: The medical device of any example herein, in particular example 43, wherein the handle comprises a finger-grip portion and head portion, the trigger is configured to translate at least partially within the finger-grip portion of the handle, and the needle hub of the needle assembly is configured to translate at least partially within the head portion of the handle in response to the actuation of the trigger.

Example 45: The medical device of any example herein, in particular example 43, further comprising a carrier structure comprising a first linear gear, and a circular gear configured to engage with the first linear gear, wherein the trigger comprises a second linear gear configured to engage with the circular gear.

Example 46: The medical device of any example herein, in particular example 45, wherein the circular gear is a compound gear comprising a first circular gear portion having a first diameter, and a second circular gear portion having a second diameter, the first diameter being greater than the second diameter.

Example 47: The medical device of any example herein, in particular example 46, wherein the first linear gear is configured to engage with teeth of the first circular gear portion, and the second linear gear is configured to engage with teeth of the second circular gear portion.

Example 48: The medical device of any example herein, in particular any of examples 45-47, further comprising a trigger lock that projects from a side of the handle, the trigger lock comprising one or more teeth configured to engage with teeth of the circular gear to rotationally lock the circular gear, thereby preventing actuation of the trigger.

Example 49: The medical device of any example herein, in particular example 48, wherein the trigger lock is configured to be laterally translated to move between locked and locked positions.

Example 50: The medical device of any example herein, in particular example 49, wherein the trigger lock comprises a state-locking feature comprising a one or more laterally-arranged teeth configured to be engaged with one or more laterally-arranged teeth of the handle, wherein the one or more teeth of the handle are spring biased towards the one or more teeth of the state-locking feature.

Example 51: The medical device of any example herein, in particular example 50, wherein the one or more laterally-arranged teeth of the state-locking feature of the trigger lock are arranged in parallel with an axis of the trigger lock.

Example 52: The medical device of any example herein, in particular any of examples 43-51, further comprising a pusher assembly including an elongate pusher tube disposed at least partially within the elongate shaft and a pusher hub disposed at least partially within the handle, wherein actuation of the trigger causes linear translation of the pusher tube within the elongate shaft.

Example 53: The medical device of any example herein, in particular example 52, wherein said actuation of the trigger causes a first linear translation of the pusher tube that is associated with commensurate translation of the needle, and a second linear translation subsequent to the first linear translation that is independent of the needle.

Example 54: The medical device of any example herein, in particular example 52, further comprising a carrier structure, wherein said actuation of the trigger causes linear translation of the carrier structure.

Example 55: The medical device of any example herein, in particular example 54, further comprising a drive rod fixedly coupled to the carrier structure such that said linear translation of the carrier structure causes linear translation of the drive rod.

Example 56: The medical device of any example herein, in particular example 55, wherein the needle hub and the pusher hub are detachably coupled to the drive rod in a manner as to longitudinally fix the needle hub and the pusher hub to respective longitudinal portions of the drive rod.

Example 57: The medical device of any example herein, in particular example 56, wherein the handle comprises a catch configured to engage with a catch of the needle hub, and when the catch of the needle hub is engaged with the catch of the handle, further linear translation of the drive rod results in detachment of the needle hub from longitudinal fixation with the drive rod.

Example 58: The medical device of any example herein, in particular example 54, further comprising a suture lock configured to secure a suture line to the handle, the suture line being disposed partially within the elongate shaft and partially within the handle.

Example 59: The medical device of any example herein, in particular example 58, wherein the carrier structure is configured to unlock the suture lock when translated to an unlock position.

Example 60: A method of deploying a tissue anchor, the method comprising providing a tissue anchor delivery device comprising an elongate shaft, a handle, a manually-pullable trigger, and a suture line running through at least a portion of the elongate shaft and the handle, the suture line having associated therewith a tissue anchor, and pulling the trigger to cause the tissue anchor to be deployed from a distal end of the elongate shaft.

Example 61: The method of any example herein, in particular example 60, wherein the tissue anchor delivery device further comprises a carrier mechanically coupled to the trigger such that actuation of the trigger causes linear actuation of the carrier, a needle instrument coupled to the carrier in a manner such that the needle instrument can be transitioned between a fixed needle coupling with the carrier in which linear translation of the carrier causes linear translation of the needle instrument and a sliding needle coupling with the carrier in which linear translation of the carrier does not cause linear translation of the needle instrument, and a pusher instrument coupled to the carrier in a manner such that the pusher instrument can be transitioned between a fixed pusher coupling with the carrier in which linear translation of the carrier causes linear translation of the pusher instrument and a sliding pusher coupling with the carrier in which linear translation of the carrier does not cause linear translation of the pusher instrument.

Example 62: The method of any example herein, in particular example 61, wherein said pulling the trigger comprises pulling the trigger a first distance, wherein said pulling the trigger the first distance causes the carrier to advance a first distance with the needle instrument in the fixed needle coupling with the carrier and the pusher instrument in the fixed pusher coupling with the carrier, thereby causing the needle instrument and the pusher instrument to advance within the elongate shaft until a distal tip of the needle instrument projects from a distal end of the elongate shaft.

Example 63: The method of any example herein, in particular example 62, wherein said advancing the carrier the first distance causes a tension in the suture line to decrease.

Example 64: The method of any example herein, in particular example 62, wherein said pulling the trigger further comprises pulling the trigger a second distance after said pulling the trigger the first distance, wherein said pulling the trigger the second distance causes the carrier to advance a second distance with the needle instrument in the sliding needle coupling with the carrier and the pusher instrument in the fixed pusher coupling with the carrier, thereby causing the pusher instrument to advance within the elongate shaft until a distal end of the pusher instrument projects from the distal end of the elongate shaft.

Example 65: The method of any example herein, in particular example 64, wherein said advancing of the carrier the second distance causes the distal end of the pusher instrument to distally pass the distal tip of the needle instrument, thereby deploying the tissue anchor from off of the needle.

Example 66: The method of any example herein, in particular example 64, wherein said pulling the trigger further comprises pulling the trigger a third distance after said pulling the trigger the second distance, wherein said pulling the trigger the third distance advances the carrier a third distance with the needle instrument in the sliding needle coupling with the carrier and the pusher instrument in the sliding pusher coupling with the carrier, such that the carrier advances the third distance independently of the needle instrument and the pusher instrument.

Example 67: The method of any example herein, in particular example 66, wherein said advancing the carrier the third distance causes a tension in the suture line to increase, and the increase in tension in the suture line causes the tissue anchor to transition to a retention form.

Example 68: The method of any example herein, in particular example 66, wherein said advancing the carrier the third distance causes the carrier to mechanically unlock a suture lock of the tissue anchor delivery device.

Example 69: The method of any example herein, in particular example 68, wherein said mechanically unlocking the suture lock involves a nose portion of the carrier displacing at least a portion of the suture lock.

Example 70: The method of any example herein, in particular example 68, further comprising, after said unlocking of the suture lock, withdrawing the tissue anchor delivery device from the suture line.

Example 71: The method of any example herein, in particular example 68, wherein said pulling the trigger the third distance causes the trigger to lock.

Example 72: The method of any example herein, in particular any of examples 61-71, wherein the needle instrument and the pusher instrument are coupled to the carrier via a drive rod that is fixed to the carrier.

Example 73: The method of any example herein, in particular example 72, wherein the suture line is routed through a channel formed in the drive rod, such that linear translation of the drive rod pulls on a portion of the suture line, thereby causing a change in tension in the suture line.

Example 74: The method of any example herein, in particular any of examples 60-73, further comprising, prior to said pulling the trigger, depressing a trigger lock that projects from a side of the handle to thereby unlock the trigger.

Depending on the example, certain acts, events, or functions of any of the processes or algorithms described herein can be performed in a different sequence, may be added, merged, or left out altogether. Thus, in certain examples, not all described acts or events are necessary for the practice of the processes.

Conditional language used herein, such as, among others, “can,” “could,” “might,” “may,” “e.g.,” and the like, unless specifically stated otherwise, or otherwise understood within the context as used, is intended in its ordinary sense and is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms “comprising,” “including,” “having,” and the like are synonymous, are used in their ordinary sense, and are used inclusively, in an open-ended fashion, and do not exclude additional elements, features, acts, operations, and so forth. Also, the term “or” is used in its inclusive sense (and not in its exclusive sense) so that when used, for example, to connect a list of elements, the term “or” means one, some, or all of the elements in the list. Conjunctive language such as the phrase “at least one of X, Y and Z,” unless specifically stated otherwise, is understood with the context as used in general to convey that an item, term, element, etc. may be either X, Y or Z. Thus, such conjunctive language is not generally intended to imply that certain examples require at least one of X, at least one of Y and at least one of Z to each be present.

It should be appreciated that in the above description of examples, various features are sometimes grouped together in a single example, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular example herein can be applied to or used with any other example(s). Further, no component, feature, step, or group of components, features, or steps are necessary or indispensable for each example. Thus, it is intended that the scope of the disclosure and appended claims should not be limited by the particular examples described above, but should be determined only by a fair reading of the claims that follow.

It should be understood that certain ordinal terms (e.g., “first” or “second”) may be provided for ease of reference and do not necessarily imply physical characteristics or ordering. Therefore, as used herein, an ordinal term (e.g., “first,” “second,” “third,” etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles (“a” and “an”) may indicate “one or more” rather than “one.” Further, an operation performed “based on” a condition or event may also be performed based on one or more other conditions or events not explicitly recited.

Unless otherwise defined, all terms (including technical and scientific terms) used herein have the same meaning as commonly understood by one of ordinary skill in the art to which example examples belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms “outer,” “inner,” “upper,” “lower,” “below,” “above,” “vertical,” “horizontal,” and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned “below” or “beneath” another device may be placed “above” another device. Accordingly, the illustrative term “below” may include both the lower and upper positions. The device may also be oriented in the other direction, and thus the spatially relative terms may be interpreted differently depending on the orientations.

Unless otherwise expressly stated, comparative and/or quantitative terms, such as “less,” “more,” “greater,” and the like, are intended to encompass the concepts of equality. For example, “less” can mean not only “less” in the strictest mathematical sense, but also, “less than or equal to”.

What is claimed is:

1. A medical instrument comprising:

a handle;

an elongate shaft;

a needle assembly including an elongate needle disposed at least partially within the elongate shaft and a needle hub disposed at least partially within the handle;

a carrier structure comprising a first linear gear;

a circular gear configured to engage with the first linear gear; and a trigger associated with the handle, the trigger being configured such that actuation of the trigger causes linear translation of the needle within the elongate shaft, the trigger comprising a second linear gear configured to engage with the circular gear.

2. The medical instrument of claim 1, wherein:
the handle comprises a finger-grip portion and head portion;
the trigger is configured to translate at least partially within the finger-grip portion of the handle; and
the needle hub of the needle assembly is configured to translate at least partially within the head portion of the handle in response to the actuation of the trigger.

3. The medical instrument of claim 1, wherein the circular gear is a compound gear comprising:
a first circular gear portion having a first diameter; and
a second circular gear portion having a second diameter, the first diameter being greater than the second diameter.

4. The medical instrument of claim 3, wherein:
the first linear gear is configured to engage with teeth of the first circular gear portion; and
the second linear gear is configured to engage with teeth of the second circular gear portion.

5. The medical instrument of claim 1, further comprising a trigger lock that projects from a side of the handle, the trigger lock comprising one or more teeth configured to engage with teeth of the circular gear to rotationally lock the circular gear, thereby preventing actuation of the trigger.

6. The medical instrument of claim 5, wherein the trigger lock is configured to be laterally translated to move between locked and locked positions.

7. The medical instrument of claim 6, wherein the trigger lock comprises a state-locking feature comprising a one or more laterally-arranged teeth configured to be engaged with one or more laterally-arranged teeth of the handle, wherein the one or more teeth of the handle are spring biased towards the one or more teeth of the state-locking feature.

8. The medical instrument of claim 7, wherein the one or more laterally-arranged teeth of the state-locking feature of the trigger lock are arranged in parallel with an axis of the trigger lock.

9. The medical instrument of claim 1, further comprising a pusher assembly including an elongate pusher tube disposed at least partially within the elongate shaft and a pusher hub disposed at least partially within the handle, wherein said actuation of the trigger causes linear translation of the pusher tube within the elongate shaft.

10. The medical instrument of claim 9, wherein said actuation of the trigger causes:
a first linear translation of the pusher tube that is associated with commensurate translation of the needle; and
a second linear translation of the pusher tube subsequent to the first linear translation that is independent of the needle.

11. The medical instrument of claim 1, wherein said actuation of the trigger causes linear translation of the carrier structure.

12. The medical instrument of claim 11, further comprising a drive rod fixedly coupled to the carrier structure such that said linear translation of the carrier structure causes linear translation of the drive rod.

13. The medical instrument of claim 12, wherein the needle hub is detachably coupled to the drive rod in a manner as to longitudinally fix the needle hub to a longitudinal portion of the drive rod.

14. The medical instrument of claim 13, wherein:
the handle comprises a catch configured to engage with a catch of the needle hub; and
when the catch of the needle hub is engaged with the catch of the handle, further linear translation of the drive rod results in detachment of the needle hub from longitudinal fixation with the drive rod.

15. The medical instrument of claim 1, further comprising a suture lock configured to secure a suture line to the handle, the suture line being disposed partially within the elongate shaft and partially within the handle.

16. A medical instrument comprising:
a handle;
an elongate shaft;
a needle assembly including an elongate needle disposed at least partially within the elongate shaft and a needle hub disposed at least partially within the handle;
a pusher assembly including an elongate pusher tube disposed at least partially within the elongate shaft and a pusher hub disposed at least partially within the handle; and
a trigger associated with the handle, the trigger being configured such that actuation of the trigger causes linear translation of the needle within the elongate shaft and linear translation of the pusher tube within the elongate shaft.

17. The medical instrument of claim 16, wherein said actuation of the trigger causes:
a first linear translation of the pusher tube that is associated with commensurate translation of the needle; and
a second linear translation of the pusher tube subsequent to the first linear translation that is independent of the needle.

18. The medical instrument of claim 16, further comprising:
a carrier structure, wherein said actuation of the trigger causes linear translation of the carrier structure; and
a drive rod fixedly coupled to the carrier structure such that said linear translation of the carrier structure causes linear translation of the drive rod;
wherein:
the needle hub and the pusher hub are detachably coupled to the drive rod in a manner as to longitudinally fix the needle hub and the pusher hub to respective longitudinal portions of the drive rod;
the handle comprises a catch configured to engage with a catch of the needle hub; and
when the catch of the needle hub is engaged with the catch of the handle, further linear translation of the drive rod results in detachment of the needle hub from longitudinal fixation with the drive rod.

19. The medical instrument of claim 16, further comprising a suture lock configured to secure a suture line to the handle, the suture line being disposed partially within the elongate shaft and partially within the handle.

* * * * *